United States Patent
Ohya et al.

(10) Patent No.: US 9,396,831 B2
(45) Date of Patent: Jul. 19, 2016

(54) POLYMER COMPOUND AND ELECTRONIC DEVICE USING THE SAME

(75) Inventors: Kenichiro Ohya, Tsukuba (JP); Ken Yoshimura, Tsukuba (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 225 days.

(21) Appl. No.: 14/118,972

(22) PCT Filed: Jun. 1, 2012

(86) PCT No.: PCT/JP2012/064736
§ 371 (c)(1),
(2), (4) Date: Nov. 20, 2013

(87) PCT Pub. No.: WO2012/169605
PCT Pub. Date: Dec. 13, 2012

(65) Prior Publication Data
US 2014/0084217 A1 Mar. 27, 2014

(30) Foreign Application Priority Data
Jun. 10, 2011 (JP) ................................. 2011-129914

(51) Int. Cl.
*H01B 1/12* (2006.01)
*C07D 493/22* (2006.01)
*C07D 495/22* (2006.01)
(Continued)

(52) U.S. Cl.
CPC .............. *H01B 1/127* (2013.01); *C07D 493/22* (2013.01); *C07D 495/22* (2013.01); *C07D 497/22* (2013.01); *C07D 498/22* (2013.01); *C07D 513/22* (2013.01); *C07D 515/22* (2013.01); *C07D 517/22* (2013.01); *C08G 61/122* (2013.01); *C08G 61/123* (2013.01); *C08G 61/126* (2013.01); *H01B 1/128* (2013.01); *H01L 51/0036* (2013.01); *C08G 2261/124* (2013.01); *C08G 2261/146* (2013.01); *C08G 2261/1412* (2013.01); *C08G 2261/3246* (2013.01); *C08G 2261/344* (2013.01); *C08G 2261/411* (2013.01); *C08G 2261/91* (2013.01); *C08G 2261/92* (2013.01); *C08G 2261/95* (2013.01); *C08L 65/00* (2013.01); *H01L 51/0043* (2013.01); *H01L 51/4253* (2013.01); *Y02E 10/549* (2013.01)

(58) Field of Classification Search
CPC .... H01B 1/127; H01B 1/128; H01L 51/0035; H01L 51/0036; C07D 493/22; C07D 495/22; C07D 497/22; C07D 498/22; C07D 513/22; C07D 515/22; C07D 517/22; C08G 61/122–61/126
See application file for complete search history.

(56) References Cited

U.S. PATENT DOCUMENTS

2005/0203257 A1* 9/2005 Uchida .................... G02B 1/04
525/437
2009/0305410 A1* 12/2009 Mao ........................ C09B 11/08
435/375
(Continued)

FOREIGN PATENT DOCUMENTS

DE WO 2011067192 A2 * 6/2011 ........... C08G 61/126
JP 2013235944 A * 11/2013
(Continued)

OTHER PUBLICATIONS

International Search Report of PCT/JP2012/064736 dated Sep. 11, 2012.

*Primary Examiner* — Mark Kopec
*Assistant Examiner* — Matthew R Diaz
(74) *Attorney, Agent, or Firm* — Sughrue Mion, PLLC

(57) ABSTRACT

A polymer compound comprising a constituent unit represented by the formula (1), the formula (2), the formula (3) or the formula (4) can be utilized for producing an organic film solar battery showing high open end voltage:

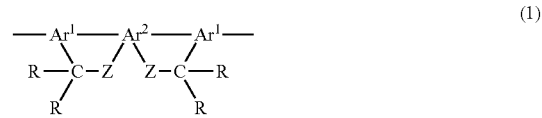

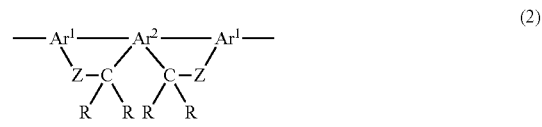

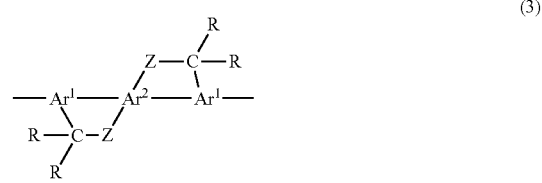

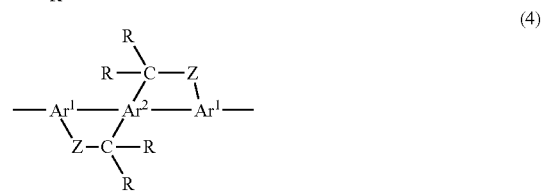

(in the formulae (1) to (4), $Ar^1$ represents a tri-valent aromatic carbocyclic group or a tri-valent aromatic heterocyclic group. $Ar^2$ represents a tetra-valent aromatic carbocyclic group or a tetra-valent aromatic heterocyclic group. Z represents —O—, —S—, —C(C=O)—, —S(=O)—, —SO$_2$—, —Si(R)$_2$—, —N(R)—, —B(R)—, —P(R)— or —P(=O)(R)—. R represents a hydrogen atom, a halogen atom or a mono-valent group.).

9 Claims, No Drawings

(51) Int. Cl.
  *C07D 497/22* (2006.01)
  *C07D 498/22* (2006.01)
  *C07D 513/22* (2006.01)
  *C07D 515/22* (2006.01)
  *C07D 517/22* (2006.01)
  *C08G 61/12* (2006.01)
  *H01L 51/00* (2006.01)
  *H01L 51/42* (2006.01)
  *C08L 65/00* (2006.01)

(56) References Cited

U.S. PATENT DOCUMENTS

2009/0309488 A1* 12/2009 Kato .................... C07D 487/04
                                                        313/504
2011/0101325 A1    5/2011 Uetani et al.

2012/0205593 A1  8/2012  Ohya et al.
2012/0205596 A1  8/2012  Yoshimura et al.
2012/0205641 A1  8/2012  Yoshimura et al.
2012/0205644 A1  8/2012  Yoshimura et al.
2012/0217448 A1  8/2012  Yoshimura et al.
2013/0214249 A1  8/2013  Pan et al.

FOREIGN PATENT DOCUMENTS

| WO | 2007/011739 A2 | 1/2007 |
| WO | 2010/001984 A1 | 1/2010 |
| WO | 2011/052702 A1 | 5/2011 |
| WO | 2011/052711 A1 | 5/2011 |
| WO | 2011/052712 A1 | 5/2011 |
| WO | 2011052710 A1  | 5/2011 |
| WO | 2012/013272 A1 | 2/2012 |

* cited by examiner

POLYMER COMPOUND AND ELECTRONIC DEVICE USING THE SAME

CROSS REFERENCE TO RELATED APPLICATIONS

This is a National Stage of International Application No. PCT/JP2012/064736 filed Jun. 1, 2012, claiming priority based on Japanese Patent Application No. 2011-129914 filed Jun. 10, 2011, the contents of all of which are incorporated herein by reference in their entirety.

TECHNICAL FIELD

The present invention relates to a polymer compound having a specific structure and an electronic device using the same.

BACKGROUND ART

Recently, reduction of $CO_2$ released into atmospheric air is required for prevention of global warming. For this reason, adoption of a solar system using a pn junction type silicon solar battery as one embodiment of electronic devices is proposed. However, monocrystalline silicon, polycrystalline silicon and amorphous silicon as materials of a silicon solar battery need high temperature and high-vacuum processes in production thereof.

In contrast, in the case of an organic film solar battery having an organic layer containing a polymer compound, high temperature and high-vacuum processes used in a process of producing a silicon solar battery can be omitted and only a coating process is used to generate a possibility of cheap production, thus, such an organic film solar battery attracts attention in recent years. As the polymer compound used in an organic film solar battery, a polymer compound composed of a repeating unit (A) and a repeating unit (B) has been suggested (WO2007/011739).

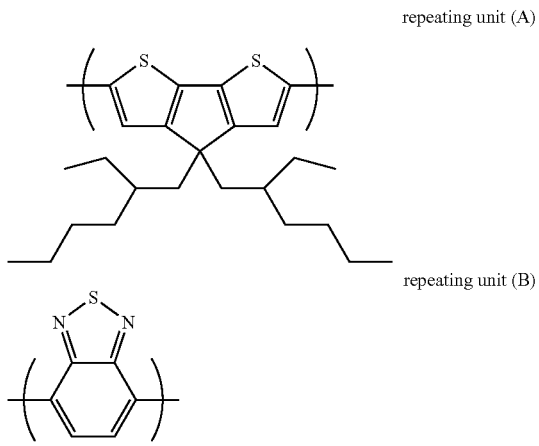

repeating unit (A)

repeating unit (B)

In the organic film solar battery having an organic layer containing this polymer compound, however, the open end voltage is not necessarily sufficiently high.

The present invention provides a polymer compound capable of attaining production of an organic film solar battery having sufficiently high open end voltage.

SUMMARY OF THE INVENTION

The present invention is as described below.

[1] A polymer compound comprising a constituent unit represented by the formula (1), the formula (2), the formula (3) or the formula (4):

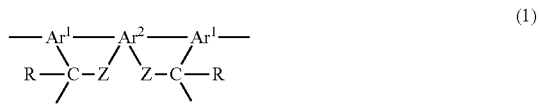
(1)

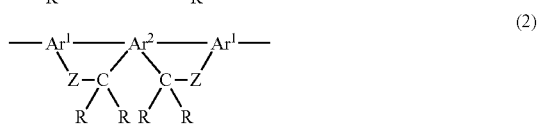
(2)

(3)

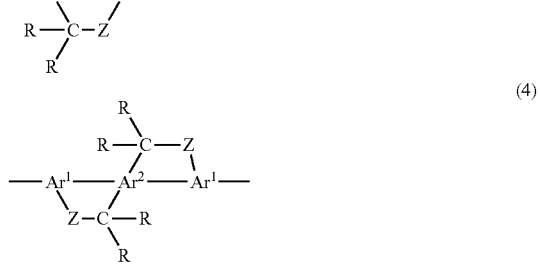
(4)

(in the formulae (1) to (4), $Ar^1$ represents a tri-valent aromatic carbocyclic group or a tri-valent aromatic heterocyclic group. $Ar^2$ represents a tetra-valent aromatic carbocyclic group or a tetra-valent aromatic heterocyclic group. Z represents —O—, —S—, —C(C=O)—, —S(=O)—, —SO$_2$—, —Si(R)$_2$—, —N(R)—, —B(R)—, —P(R)— or —P(=O)(R)—. R represents a hydrogen atom, a halogen atom or a mono-valent group. Two $Ar^1$s may be the same or mutually different. Two Zs may be the same or mutually different. A plurality of Rs may be the same or mutually different.).

[2] The polymer compound according to [1], wherein the constituent unit represented by the formula (1), the formula (2), the formula (3) or the formula (4) is a constituent unit represented by the formula (5), the formula (6), the formula (7) or the formula (8):

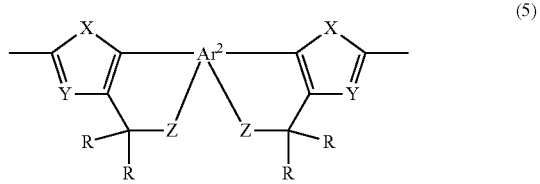
(5)

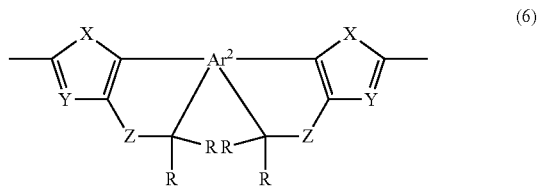
(6)

(7)

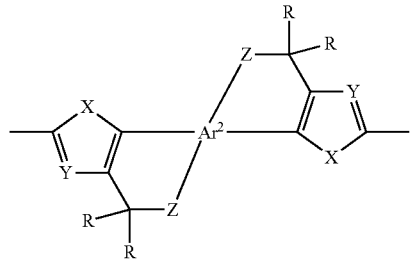

(8)

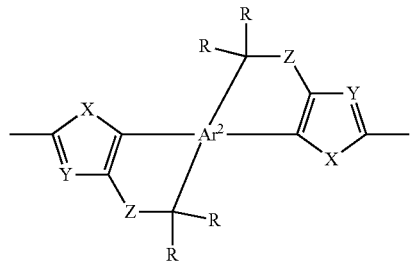

(in the formulae (5) to (8), X represents a sulfur atom, an oxygen atom, a selenium atom, —NH— or —N(R)—. $Ar^2$, Z and R represent the same meaning as described above. Y represents a nitrogen atom or =CH—. Two Xs may be the same or mutually different. Two Ys may be the same or mutually different.).

[3] The polymer compound according to [1], wherein the constituent unit represented by the formula (1), the formula (2), the formula (3) or the formula (4) is a constituent unit represented by the formula (9), the formula (10), the formula (11) or the formula (12):

(9)

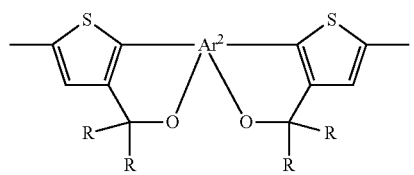

(10)

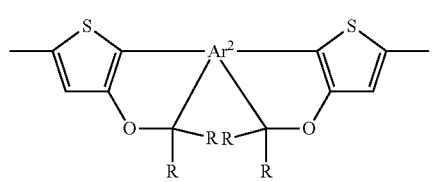

(11)

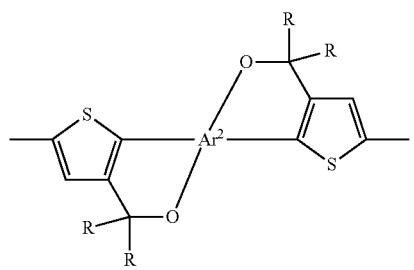

(12)

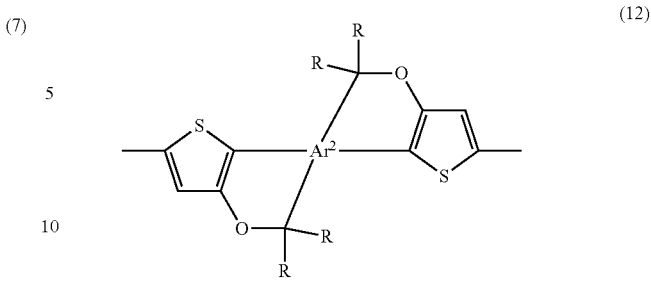

(in the formulae (9) to (12), $Ar^2$ and R represent the same meaning as described above.).

[4] The polymer compound according to any one of [1] to [3], having a polystyrene-equivalent number-average molecular weight of 3000 or more.

[5] A film comprising the polymer compound according to any one of [1] to [4].

[6] A composition comprising the polymer compound according to any one of [1] to [4] and an electron accepting compound.

[7] The composition according to [6], wherein the electron accepting compound is a fullerene derivative.

[8] A film comprising the composition according to [6] or [7].

[9] An electronic device using the film according to [5] or [8].

[10] A compound represented by the formula (13):

(13)

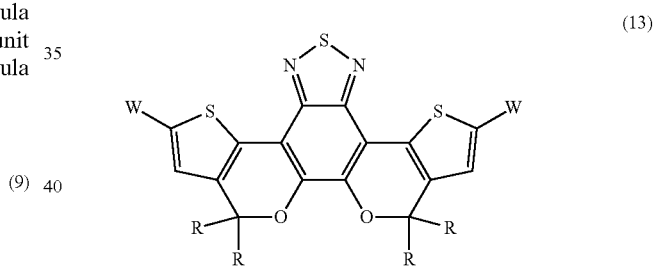

(wherein R represents a hydrogen atom, a halogen atom or a mono-valent group. W represents a hydrogen atom, a halogen atom, a borate residue, a dihydroxyboryl group, a formyl group, a vinyl group or a substituted stannyl group. Four Rs may be the same or mutually different. Two Ws may be the same or mutually different.).

[11] A compound represented by the formula (14):

(14)

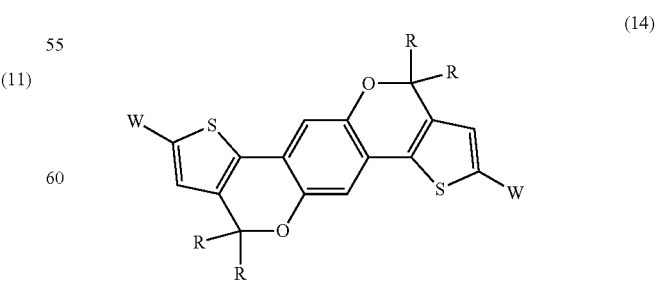

(wherein R represents a hydrogen atom, a halogen atom or a mono-valent group. W represents a hydrogen atom, a halogen atom, a borate residue, a dihydroxyboryl group, a formyl group, a vinyl group or a substituted stannyl group. Four Rs may be the same or mutually different. Two Ws may be the same or mutually different.).

MODES FOR CARRYING OUT THE INVENTION

The present invention will be illustrated in detail below.

The polymer compound of the present invention comprises a constituent unit represented by the formula (1), the formula (2), the formula (3) or the formula (4).

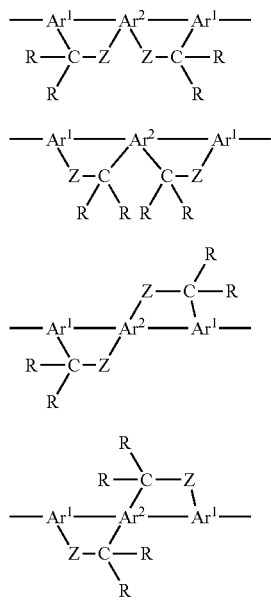

In the formulae (1) to (4), Z represents —O—, —S—, —C(C═O)—, —S(═O)—, —SO$_2$—, —Si(R)$_2$—, —N(R)—, —B(R)—, —P(R)— or —P(═O)(R)—. In light of easiness of production of monomers as raw materials of the polymer compound of the present invention, Z represents preferably —O— or —S—, more preferably —O—.

In the formulae (1) to (4), R represents a hydrogen atom, a halogen atom (fluorine atom, chlorine atom, bromine atom and iodine atom) or a mono-valent group. The mono-valent group includes, for example, an optionally substituted alkyl group, an optionally substituted alkoxy group, an optionally substituted alkylthio group, an optionally substituted aryl group, an optionally substituted aryloxy group, an optionally substituted arylthio group, an optionally substituted arylalkyl group, an optionally substituted arylalkoxy group, an optionally substituted arylalkylthio group, an optionally substituted acyl group, an optionally substituted acyloxy group, an amide group, an imide group, an amino group, a substituted amino group, a substituted silyl group, a substituted silyloxy group, a substituted silylthio group, a substituted silylamino group, a heterocyclic group, a heterocyclic oxy group, a heterocyclic thio group, an arylalkenyl group, an arylalkynyl group, a carboxyl group and a cyano group. A plurality of Rs may be the same or mutually different.

The alkyl group may be linear or branched, or may also be cyclic. The alkyl group has a number of carbon atoms of usually 1 to 30. The substituent optionally carried on the alkyl group includes, for example, a halogen atom. Specific examples of the alkyl group include linear alkyl groups such as a methyl group, an ethyl group, a propyl group, an isopropyl group, a butyl group, an isobutyl group, a sec-butyl group, a tert-butyl group, a pentyl group, an isopentyl group, a 2-methylbutyl group, a 1-methylbutyl group, a hexyl group, an isohexyl group, a 3-methylpentyl group, a 2-methylpentyl group, a 1-methylpentyl group, a heptyl group, an octyl group, an isooctyl group, a 2-ethylhexyl group, a 3,7-dimethyloctyl group, a nonyl group, a decyl group, an undecyl group, a dodecyl group, a tetradecyl group, a hexadecyl group, an octadecyl group, an eicosyl group and the like, and cycloalkyl groups such as a cyclopentyl group, a cyclohexyl group, an adamantyl group and the like.

The alkyl portion of the alkoxy group may be linear or branched, or may also be cyclic. The substituent optionally carried on the alkoxy group includes, for example, a halogen atom. The alkoxy group has a number of carbon atoms of usually 1 to 20. Specific examples of the optionally substituted alkoxy group include a methoxy group, an ethoxy group, a propoxy group, an isopropoxy group, a butoxy group, an isobutoxy group, a tert-butoxy group, a pentyloxy group, a hexyloxy group, a cyclohexyloxy group, a heptyloxy group, an octyloxy group, a 2-ethylhexyloxy group, a nonyloxy group, a decyloxy group, a 3,7-dimethyloctyloxy group, a lauryloxy group, a trifluoromethoxy group, a pentafluoroethoxy group, a perfiluorobutoxy group, a perfluorohexyloxy group, a perfluorooctyloxy group, a methoxymethyloxy group and a 2-methoxyethyloxy group.

The alkyl portion of the alkylthio group may be linear or branched, or may also be cyclic. The substituent optionally carried on the alkylthio group includes, for example, a halogen atom. The alkylthio group has a number of carbon atoms of usually 1 to 20. Specific examples of the optionally substituted alkylthio group include a methylthio group, an ethylthio group, a propylthio group, an isopropylthio group, a butylthio group, an isobutylthio group, a tert-butylthio group, a pentylthio group, a hexylthio group, a cyclohexylthio group, a heptylthio group, an octylthio group, a 2-ethylhexylthio group, a nonylthio group, a decylthio group, a 3,7-dimethyloctylthio group, a laurylthio group and a trifluoromethylthio group.

The aryl group is an atomic group obtained by removing one hydrogen atom on an aromatic ring from an aromatic hydrocarbon and has a number of carbon atoms of usually 6 to 60. The substituent optionally carried on the aryl group includes, for example, a halogen atom, an optionally substituted alkyl group, an optionally substituted alkoxy group and an optionally substituted alkylthio group. The definition and specific examples of the optionally substituted alkyl group, the optionally substituted alkoxy group and the optionally substituted alkylthio group are the same as the definition and specific examples of the optionally substituted alkyl group, the optionally substituted alkoxy group and the optionally substituted alkylthio group represented by R. Specific examples of the optionally substituted aryl group include a phenyl group, C1 to C12 alkoxyphenyl groups (The C1 to C12 alkyl denotes an alkyl having 1 to 12 carbon atoms. The C1 to C12 alkyl is preferably a C1 to C8 alkyl, more preferably a C1 to C6 alkyl. The C1 to C8 alkyl denotes an alkyl having 1 to 8 carbon atoms, and the C1 to C6 alkyl denotes an alkyl having 1 to 6 carbon atoms. Specific examples of the C1 to C12 alkyl, the C1 to C8 alkyl and the C1 to C6 alkyl include those explained and exemplified for the above-described alkyl group. The same shall apply hereinafter.), C1 to C12 alkylphenyl groups, a 1-naphthyl group, a 2-naphthyl group and a pentafluorophenyl group.

The aryloxy group has a number of carbon atoms of usually 6 to 60. The substituent optionally carried on the aryloxy group includes, for example, a halogen atom, an optionally substituted alkyl group, an optionally substituted alkoxy group and an optionally substituted alkylthio group. The definition and specific examples of the optionally substituted alkyl group, the optionally substituted alkoxy group and the optionally substituted alkylthio group are the same as the definition and specific examples of the optionally substituted alkyl group, the optionally substituted alkoxy group and the optionally substituted alkylthio group represented by R. Specific examples of the optionally substituted aryloxy group include a phenoxy group, C1 to C12 alkoxyphenoxy groups, C1 to C12 alkylphenoxy groups, a 1-naphthyloxy group, a 2-naphthyloxy group and a pentafluorophenyloxy group.

The arylthio group has a number of carbon atoms of usually 6 to 60. The substituent optionally carried on the arylthio group includes, for example, a halogen atom, an optionally substituted alkyl group, an optionally substituted alkoxy group and an optionally substituted alkylthio group. The definition and specific examples of the optionally substituted alkyl group, the optionally substituted alkoxy group and the optionally substituted alkylthio group are the same as the definition and specific examples of the optionally substituted alkyl group, the optionally substituted alkoxy group and the optionally substituted alkylthio group represented by R. Specific examples of the optionally substituted arylthio group include a phenylthio group, C1 to C12 alkyloxyphenylthio groups, C1 to C12 alkylphenylthio groups, a 1-naphthylthio group, a 2-naphthylthio group and a pentafluorophenylthio group.

The arylalkyl group has a number of carbon atoms of usually 7 to 60. The substituent optionally carried on the arylalkyl group includes, for example, a halogen atom, an optionally substituted alkyl group, an optionally substituted alkoxy group and an optionally substituted alkylthio group. The definition and specific examples of the optionally substituted alkyl group, the optionally substituted alkoxy group and the optionally substituted alkylthio group are the same as the definition and specific examples of the optionally substituted alkyl group, the optionally substituted alkoxy group and the optionally substituted alkylthio group represented by R. The alkyl portion may have a substituent such as a halogen atom and the like. Specific examples of the optionally substituted arylalkyl group include phenyl C1 to C12 alkyl groups, C1 to C12 alkoxyphenyl C1 to C12 alkyl groups, C1 to C12 alkylphenyl C1 to C12 alkyl groups, 1-naphthyl-C1 to C12 alkyl groups and 2-naphthl-C1 to C12 alkyl groups.

The arylalkoxy group has a number of carbon atoms of usually 7 to 60. The substituent optionally carried on the arylalkoxy group includes, for example, a halogen atom, an optionally substituted alkyl group, an optionally substituted alkoxy group and an optionally substituted alkylthio group. The definition and specific examples of the optionally substituted alkyl group, the optionally substituted alkoxy group and the optionally substituted alkylthio group are the same as the definition and specific examples of the optionally substituted alkyl group, the optionally substituted alkoxy group and the optionally substituted alkylthio group represented by R. The alkoxy portion may have a substituent such as a halogen atom and the like. Specific examples of the optionally substituted arylalkoxy group include phenyl C1 to C12 alkoxy groups, C1 to C12 alkoxyphenyl C1 to C12 alkoxy groups, C1 to C12 alkylphenyl C1 to C12 alkoxy groups, 1-naphthyl-C1 to C12 alkoxy groups and 2-naphthyl-C1 to C12 alkoxy groups.

The arylalkylthio group has a number of carbon atoms of usually 7 to 60. The substituent optionally carried on the arylalkylthio group includes, for example, a halogen atom, an optionally substituted alkyl group, an optionally substituted alkoxy group and an optionally substituted alkylthio group. The definition and specific examples of the optionally substituted alkyl group, the optionally substituted alkoxy group and the optionally substituted alkylthio group are the same as the definition and specific examples of the optionally substituted alkyl group, the optionally substituted alkoxy group and the optionally substituted alkylthio group represented by R. The alkylthio portion may have a substituent such as a halogen atom and the like. Specific examples of the optionally substituted arylalkylthio group include phenyl C1 to C12 alkylthio groups, C1 to C12 alkoxyphenyl C1 to C12 alkylthio groups, C1 to C12 alkylphenyl C1 to C12 alkylthio groups, 1-naphthyl-C1 to C12 alkylthio groups and 2-naphthyl-C1 to C12 alkylthio groups.

The acyl group is usually a hydrocarbylcarbonyl group having 2 to 20 carbon atoms. The substituent optionally carried on the acyl group includes, for example, a halogen atom. Specific examples of the optionally substituted acyl group include an acetyl group, a propionyl group, a butyryl group, an isobutyryl group, a pivaloyl group, a benzoyl group, a trifluoroacetyl group and a pentafluorobenzoyl group.

The acyloxy group has a number of carbon atoms of usually 2 to 20. The substituent optionally carried on the acyloxy group includes, for example, a halogen atom. Specific examples of the optionally substituted acyloxy group include an acetoxy group, a propionyloxy group, a butyryloxy group, an isobutyryloxy group, a pivaloyloxy group, a benzoyloxy group, a trifluoroacetyloxy group and a pentafluorobenzoyloxy group.

The amide group is typically an optionally substituted hydrocarbylcarbonylamino group and has a number of carbon atoms of usually 1 to 20. The substituent includes, for example, a halogen atom. Specific examples of the amide group include a formamide group, an acetamide group, a propioamide group, a butyroamide group, a benzamide group, a trifluoroacetamide group and a pentafluorobenzamide group.

The imide group is typically a diacylamino group, and the acyl portion may have a substituent. The substituent includes, for example, a halogen atom. Specific examples of the imide group include a succinimide group, a phthalimide group, a diformamide group, a diacetylamino group, a dipropionylamino group, a dibutyroylamino group, a dibenzoylamino group, a bistrifluoroacetylamino group and a bispentafluorobenzoylamino group.

The substituted amino group has a number of carbon atoms of usually 1 to 40. The substituent carried on the substituted amino group includes, for example, an optionally substituted alkyl group and aryl group. The definition and specific examples of the optionally substituted alkyl group and aryl group are the same as the definition and specific examples of the optionally substituted alkyl group and aryl group represented by R. Specific examples of the substituted amino group include a methylamino group, a dimethylamino group, an ethylamino group, a diethylamino group, a propylamino group, a dipropylamino group, an isopropylamino group, a diisopropylamino group, a butylamino group, an isobutylamino group, a tert-butylamino group, a pentylamino group, a hexylamino group, a cyclohexylamino group, a heptylamino group, an octylamino group, a 2-ethylhexylamino group, a nonylamino group, a decylamino group, a 3,7-dimethyloctylamino group, a laurylamino group, a cyclopentylamino group, a dicyclopentylamino group, a cyclohexylamino group, a dicyclohexylamino group, a pyrrolidyl group, a piperidyl group, a ditrifluoromethylamino group, a phenylamino group, a diphenylamino group, C1 to C12 alkoxyphenylamino groups, di(C1 to C12 alkoxyphenyl)

amino groups, di(C1 to C12 alkylphenyl)amino groups, a 1-naphthylamino group, a 2-naphthylamino group, a pentafluorophenylamino group, a pyridylamino group, a pyridazinylamino group, a pyrimidylamino group, a pyrazylamino group, a triazylamino group, phenyl C1 to C12 alkylamino groups, C1 to C12 alkoxyphenyl C1 to C12 alkylamino groups, C1 to C12 alkylphenyl C1 to C12 alkylamino groups, di(C1 to C12 alkoxyphenyl C1 to C12 alkyl)amino groups, di(C1 to C12 alkylphenyl C1 to C12 alkyl)amino groups, 1-naphthyl-C1 to C12 alkylamino groups and 2-naphthyl-C1 to C12 alkylamino groups.

The substituent carried on the substituted silyl group includes, for example, an optionally substituted alkyl group and aryl group. The definition and specific examples of the optionally substituted alkyl group and aryl group are the same as the definition and specific examples of the optionally substituted alkyl group and aryl group represented by R. Specific examples of the substituted silyl group include a trimethylsilyl group, a triethylsilyl group, a tripropylsilyl group, a triisopropylsilyl group, a tert-butyldimethylsilyl group, a triphenylsilyl group, a tri-p-xylylsilyl group, a tribenzylsilyl group, a diphenylmethylsilyl group, a tert-butyldiphenylsilyl group and a dimethylphenylsilyl group.

The substituent carried on the substituted silyloxy group includes, for example, an optionally substituted alkyl group and aryl group. The definition and specific examples of the optionally substituted alkyl group and aryl group are the same as the definition and specific examples of the optionally substituted alkyl group and aryl group represented by R. Specific examples of the substituted silyloxy group include a trimethylsilyloxy group, a triethylsilyloxy group, a tripropylsilyloxy group, a triisopropylsilyloxy group, a tert-butyldimethylsilyloxy group, a triphenylsilyloxy group, a tri-p-xylylsilyloxy group, a tribenzylsilyloxy group, a diphenylmethylsilyloxy group, a tert-butyldiphenylsilyloxy group and a dimethylphenylsilyloxy group.

The substituent carried on the substituted silylthio group includes, for example, an optionally substituted alkyl group and aryl group. The definition and specific examples of the optionally substituted alkyl group and aryl group are the same as the definition and specific examples of the optionally substituted alkyl group and aryl group represented by R. Specific examples of the substituted silylthio group include a trimethylsilylthio group, a triethylsilylthio group, a tripropylsilylthio group, a triisopropylsilylthio group, a tert-butyldimethylsilylthio group, a triphenylsilylthio group, a tri-p-xylylsilylthio group, a tribenzylsilylthio group, a diphenylmethylsilylthio group, a tert-butyldiphenylsilylthio group and a dimethylphenylsilylthio group.

The substituent carried on the substituted silylamino group includes, for example, an optionally substituted alkyl group and aryl group. The definition and specific examples of the optionally substituted alkyl group and aryl group are the same as the definition and specific examples of the optionally substituted alkyl group and aryl group represented by R. Specific examples of the substituted silylamino group include a trimethylsilylamino group, a triethylsilylamino group, a tripropylsilylamino group, a triisopropylsilylamino group, a tert-butyldimethylsilylamino group, a triphenylsilylamino group, a tri-p-xylylsilylamino group, a tribenzylsilylamino group, a diphenylmethylsilylamino group, a tert-butyldiphenylsilylamino group, a dimethylphenylsilylamino group, a di(trimethylsilyl)amino group, a di(triethylsilyl)amino group, a di(tripropylsilyl)amino group, a di(triisopropylsilyl)amino group, a di(tert-butyldimethylsilyl)amino group, a di(triphenylsilyl)amino group, a di(tri-p-xylylsilyl)amino group, a di(tribenzylsilyl)amino group, a di(diphenylmethylsilyl) amino group, a di(tert-butyldiphenylsilyl)amino group and a di(dimethylphenylsilyl)amino group.

The heterocyclic group is an atomic group obtained by removing one hydrogen atom on a hetero ring from an optionally substituted heterocyclic compound. The heterocyclic compound includes, for example, furan, thiophene, pyrrole, pyrroline, pyrrolidine, oxazole, isooxazole, thiazole, isothiazole, imidazole, imidazoline, imidazolidine, pyrazole, pyrazoline, pyrazolidine, furazan, triazole, thiadiazole, oxadiazole, tetrazole, pyran, pyridine, piperidine, thiopyran, pyridazine, pyrimidine, pyrazine, piperazine, morpholine, triazine, benzofuran, isobenzofuran, benzothiophene, indole, isoindole, indolizine, indoline, isoindoline, chromene, chromane, isochromane, benzopyran, quinoline, isoquinoline, quinolizine, benzoimidazole, benzothiazole, indazole, naphthyridine, quinoxaline, quinazoline, quinazolidine, cinnoline, phthalazine, purine, pteridine, carbazole, xanthene, phenanthridine, acridine, β-carboline, perimidine, phenanthroline, thianthrene, phenoxathiin, phenoxazine, phenothiazine and phenazine. The substituent optionally carried on the heterocyclic compound includes, for example, a halogen atom, an optionally substituted alkyl group, an optionally substituted alkoxy group and an optionally substituted alkylthio group. The definition and specific examples of the optionally substituted alkyl group, the optionally substituted alkoxy group and substituted and the optionally substituted alkylthio group are the same as the definition and specific examples of the optionally substituted alkyl group, the optionally substituted alkoxy group and the optionally substituted alkylthio group represented by R. As the heterocyclic group, aromatic heterocyclic groups are preferable.

The heterocyclic oxy group includes groups represented by the formula (A-1) obtained by linking an oxygen atom to the above-described heterocyclic group.

The heterocyclic thio group includes groups represented by the formula (A-2) obtained by linking a sulfur atom to the above-described heterocyclic group.

$$Ar^3\text{—}O\text{—} \quad (A\text{-}1)$$

$$Ar^3\text{—}S\text{—} \quad (A\text{-}2)$$

(in the formula (A-1) and the formula (A-2), $Ar^3$ represents a heterocyclic group.)

Specific examples of the heterocyclic oxy group include a thienyloxy group, C1 to C12 alkylthienyloxy groups, a pyrrolyloxy group, a furyloxy group, a pyridyloxy group, C1 to C12 alkylpyridyloxy groups, an imidazolyloxy group, a pyrazolyloxy group, a triazolyloxy group, an oxazolyloxy group, a thiazoleoxy group and a thiadiazoleoxy group.

Specific examples of the heterocyclic thio group include a thienylmercapto group, C1 to C12 alkylthienylmercapto groups, a pyrrolylmercapto group, a furylmercapto group, a pyridylmercapto group, C1 to C12 alkylpyridylmercapto groups, an imidazolylmercapto group, a pyrazolylmercapto group, a triazolylmercapto group, an oxazolylmercapto group, a thiazolemercapto group and a thiadiazolemercapto group.

The arylalkenyl group usually has a number of carbon atoms of 8 to 20. Specific examples of the arylalkenyl group include a styryl group.

The arylalkynyl group usually has a number of carbon atoms of 8 to 20. Specific examples of the arylalkynyl group include a phenylacetylenyl group.

From the standpoint of enhancing the solubility of the polymer compound of the present invention in a solvent, preferable as R are alkyl groups having 6 or more carbon atoms, alkoxy groups having 6 or more carbon atoms, alkylthio groups having 6 or more carbon atoms, aryl groups, aryloxy groups, arylthio groups, arylalkyl groups, arylalkyloxy groups, arylalkylthio groups, acyl groups having 6 or more carbon atoms and acyloxy groups having 6 or more carbon atoms, more preferable are alkyl groups having 6 or more carbon atoms, alkoxy groups having 6 or more carbon atoms, aryl groups and aryloxy groups, particularly preferable are alkyl groups having 6 or more carbon atoms.

The alkyl group having 6 or more carbon atoms as a preferable embodiment of R includes linear alkyl groups such as a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an icosyl group, a triacontyl group, a tetracontyl group, a pentacontyl group and the like, and branched alkyl groups such as a 1,1,3,3-tetramethylbutyl group, a 1-methylheptyl group, a 2-ethylhexyl group, a 3,7-dimethyloctyl group, a 1-propylpentyl group, a 2-hexyldecyl group, a 2-heptylundecyl group, a 2-octyldodecyl group, a 3,7,11-trimethyldodecyl group, a 3,7,11,15-tetramethylhexadecyl group, a 3,5,5-trimethylhexyl group and the like.

The optionally substituted aryl group as a preferable embodiment of R is appropriately selected in view of the solubility of the polymer compound of the present invention in a solvent and the like, and preferable are phenyl groups substituted by an alkyl group. The substitution position of an alkyl group is preferably a para-position. The phenyl group having a substituted alkyl group at the para position includes preferably a p-hexylphenyl group, a p-heptylphenyl group, a p-octylphenyl group, a p-nonylphenyl group, a p-decylphenyl group, a p-undecylphenyl group, a p-dodecylphenyl group, a p-tridecylphenyl group, a p-tetradecylphenyl group, a p-pentadecylphenyl group, a p-hexadecylphenyl group, a p-2-ethylhexylphenyl group, a p-3,7-dimethyloctylphenyl group, a p-1-propylpentylphenyl group and a p-2-hexyldecylphenyl group, more preferably a p-hexylphenyl group, a p-heptylphenyl group, a p-octylphenyl group, a p-dodecylphenyl group, a p-pentadecylphenyl group, a p-hexadecylphenyl group, a p-2-ethylhexylphenyl group, a p-3,7-dimethyloctylphenyl group and a p-2-hexyldecylphenyl group, particularly preferably a p-dodecylphenyl group, a p-pentadecylphenyl group, a p-2-ethylhexylphenyl group and a p-3,7-dimethyloctylphenyl group.

The tri-valent aromatic heterocyclic group represented by Ar¹ denotes an atomic group remaining after removing three hydrogen atoms on an aromatic ring from an optionally substituted aromatic heterocyclic compound. The tri-valent aromatic heterocyclic group has a number of carbon atoms of usually 2 to 60, preferably 4 to 60, more preferably 4 to 20.

The substituent optionally carried on the heterocyclic compound having aromaticity includes, for example, a halogen atom and a mono-valent group. The definition and specific examples of the mono-valent group are the same as the definition and specific examples of the mono-valent group represented by R.

The tri-valent aromatic heterocyclic group includes, for example, groups represented by the formulae (201) to (301).

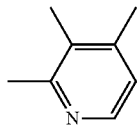

(201)

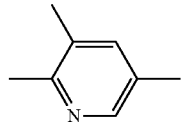

(202)

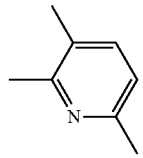

(203)

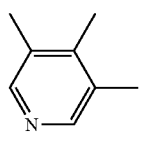

(204)

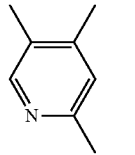

(205)

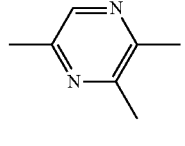

(206)

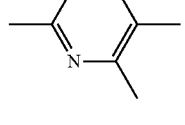

(207)

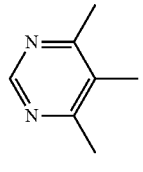

(208)

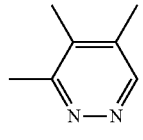

(209)

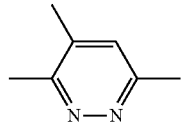

(210)

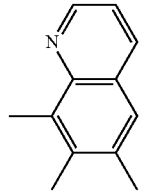

(211)

(212) 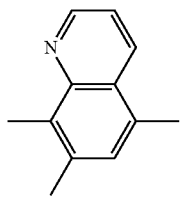
(213) 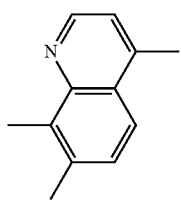
(214) 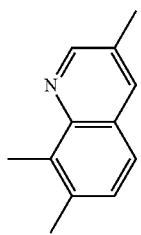
(215) 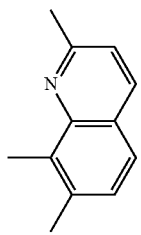
(216) 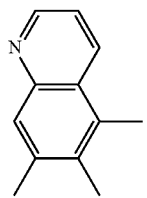
(217) 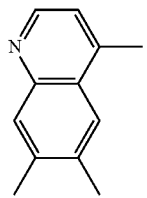
(218) 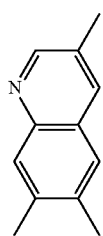
(219) 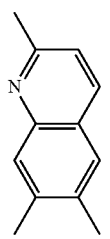
(220) 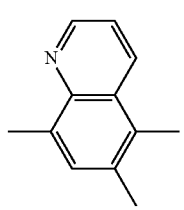
(221) 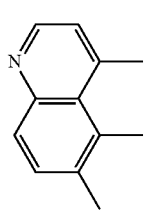
(222) 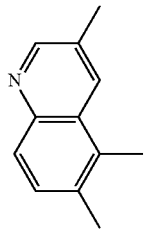
(223) 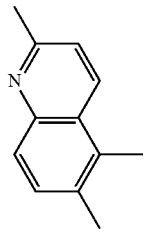
(224) 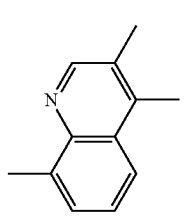
(225) 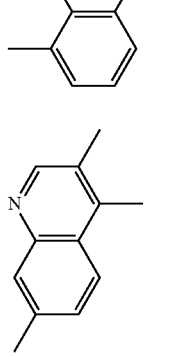

(226) 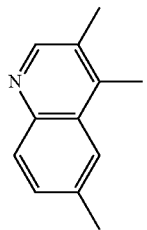
(227) 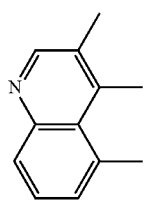
(228) 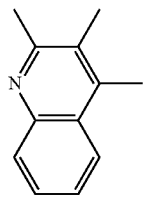
(229) 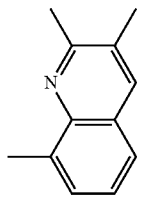
(230) 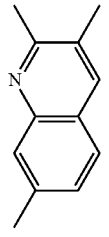
(231) 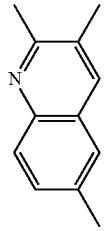
(232) 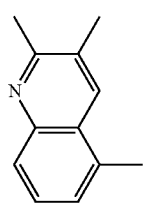
(233) 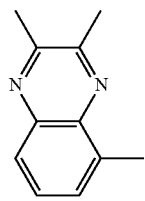
(234) 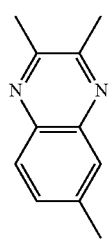
(235) 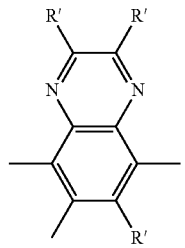
(236) 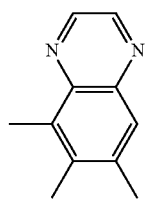
(237) 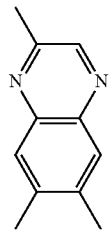
(238) 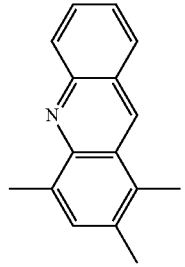

-continued
(239) 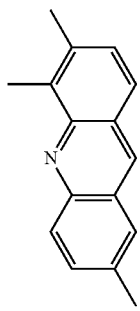
(240) 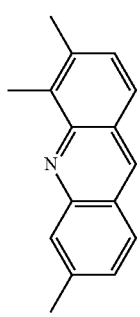
(241) 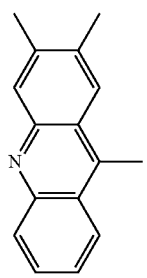
(242) 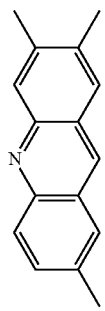
(243) 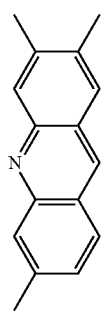
(244) 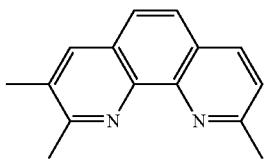
(245) 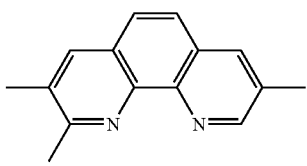
(246) 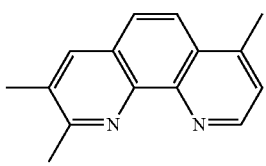
(247) 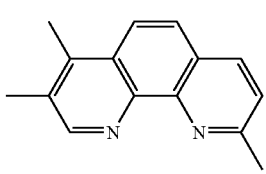
(248) 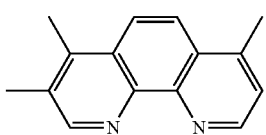
(249) 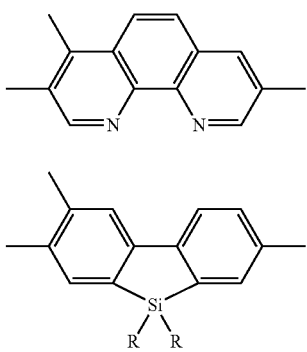
(250) 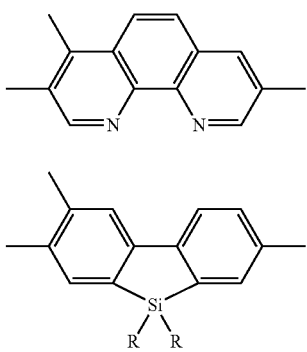
(251) 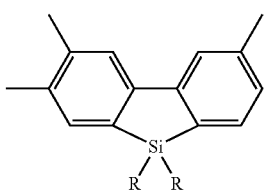
(252) 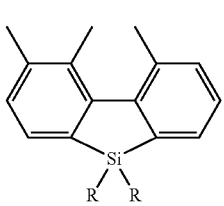

(253) 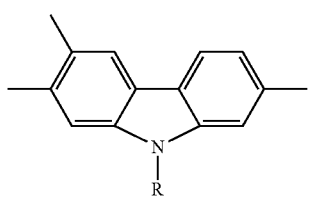
(254) 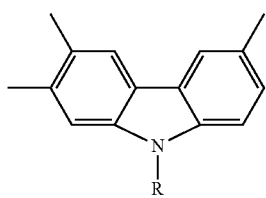
(255) 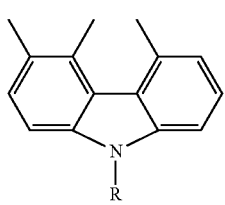
(256) 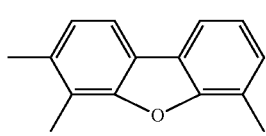
(257) 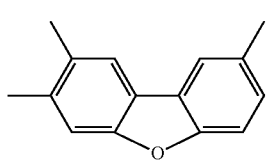
(258) 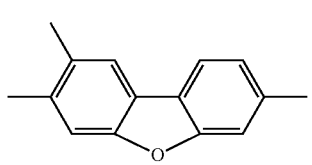
(259) 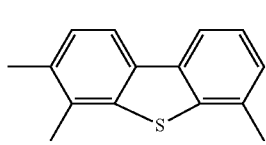
(260) 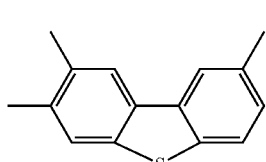
(261) 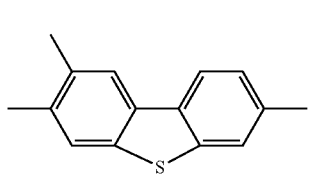
(262) 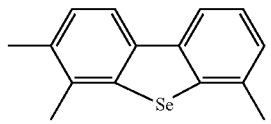
(263) 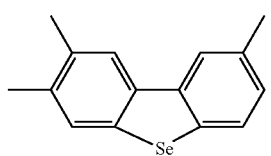
(264) 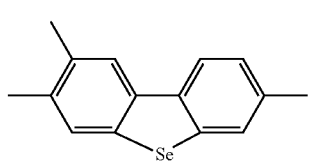
(265) 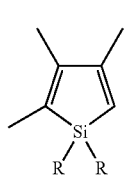
(266) 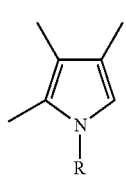
(267) 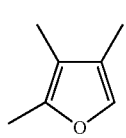
(268) 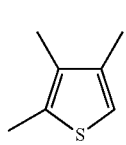
(269) 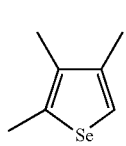
(270) 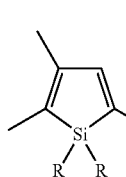
(271) 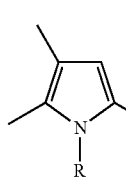

(272) 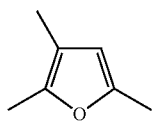
(273) 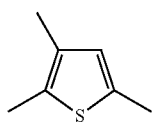
(274) 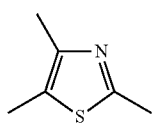
(275) 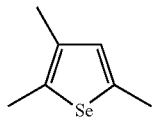
(276) 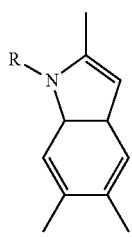
(277) 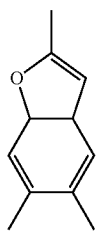
(278) 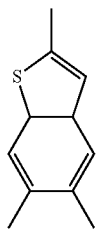
(279) 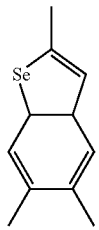
(280) 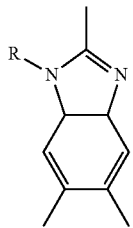
(281) 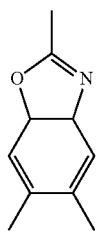
(282) 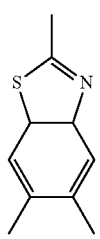
(283) 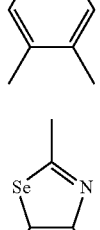
(284) 
(285) 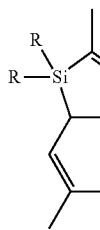
(286) 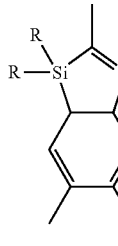

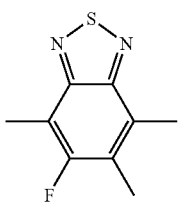 (287)
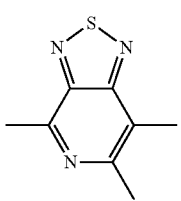 (288)
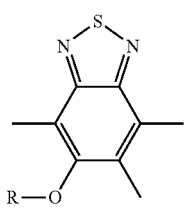 (289)
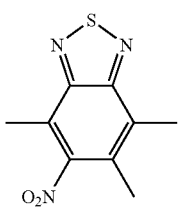 (290)
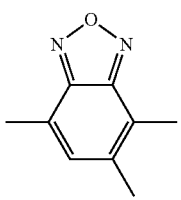 (291)
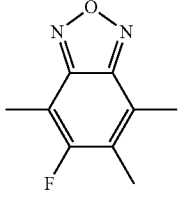 (292)
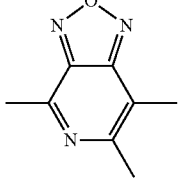 (293)
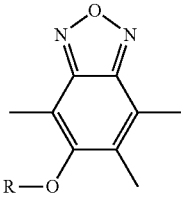 (294)
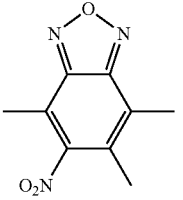 (295)
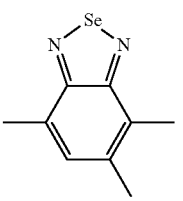 (296)
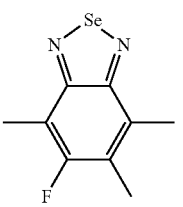 (297)
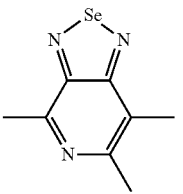 (298)
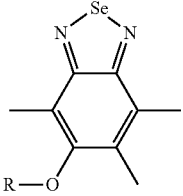 (299)
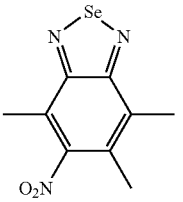 (300)
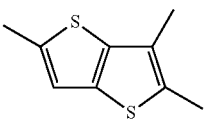 (301)

(wherein R represents the same meaning as described above.)

The tri-valent aromatic carbocyclic group represented by $Ar^1$ denotes an atomic group remaining after removing three hydrogen atoms on an aromatic ring from an optionally substituted aromatic hydrocarbon. The tri-valent aromatic carbocyclic group has a number of carbon atoms of usually 6 to 60, preferably 6 to 20.

The aromatic hydrocarbon includes also compounds containing a benzene ring, compounds containing a condensed ring, compounds containing a structure in which independent two or more benzene rings or condensed rings are linked directly, and compounds in which independent two or more benzene rings or condensed rings are linked via a group such as a vinylene group and the like.

The substituent optionally carried on the aromatic hydrocarbon includes, for example, a halogen atom and a mono-valent group. The definition and specific examples of the mono-valent group are the same as the definition and specific examples of the mono-valent group represented by R.

The tri-valent aromatic carbocyclic group includes, for example, groups represented by the formulae (302) to (311).

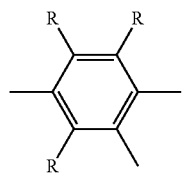
(302)

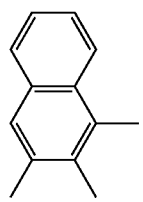
(303)

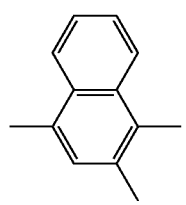
(304)

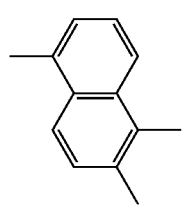
(305)

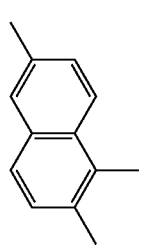
(306)

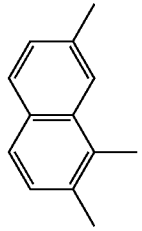
(307)

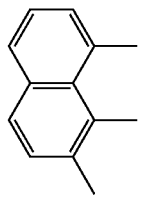
(308)

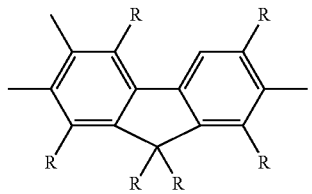
(309)

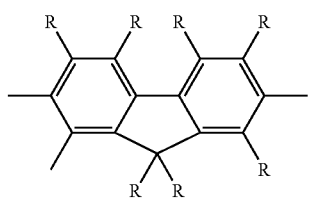
(310)

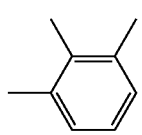
(311)

(wherein R represents the same meaning as described above.)

Among groups represented by the formulae (201) to (311), preferable from the standpoint of easiness of synthesis of monomers used as raw materials of the polymer compound of the present invention are groups represented by the formula (202), the formula (205), the formula (206), the formula (207), the formula (210), the formula (212), the formula (220), the formula (235), the formula (238), the formula (270), the formula (271), the formula (272), the formula (273), the formula (274), the formula (275), the formula (286), the formula (287), the formula (288), the formula (291), the formula (292), the formula (293), the formula (296), the formula (301) and the formula (302), more preferable are groups represented by the formula (235), the formula (271), the formula (272), the formula (273), the formula (274), the formula (286), the formula (291), the formula (296), the formula (301) and the formula (302), further preferable are groups represented by the formula (271), the formula (272), the formula (273), the formula (274) and the formula (311), particularly preferable is a group represented by the formula (273).

The tetra-valent aromatic heterocyclic group represented by $Ar^2$ denotes an atomic group remaining after removing four hydrogen atoms on an aromatic ring from an optionally substituted heterocyclic compound having aromaticity. The tetra-valent aromatic heterocyclic group has a number of carbon atoms of usually 2 to 60, preferably 4 to 60, more preferably 4 to 20.

The substituent optionally carried on the heterocyclic compound having aromaticity includes, for example, a halogen atom and a mono-valent group. The definition and specific examples of the mono-valent group are the same as the definition and specific examples of the mono-valent group represented by R.

The tetra-valent aromatic heterocyclic group includes, for example, groups represented by the formulae (401) to (447).

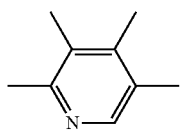
(401)

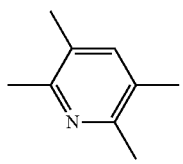
(402)

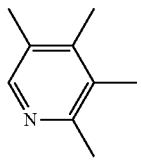
(403)

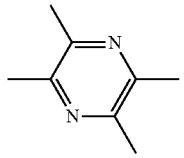
(404)

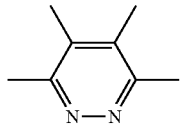
(405)

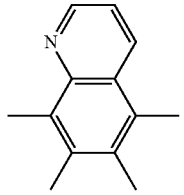
(406)

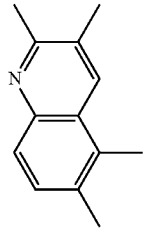
(407)

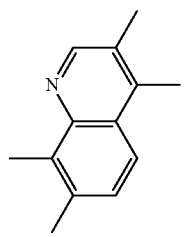
(408)

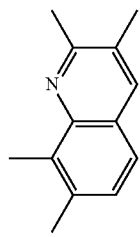
(409)

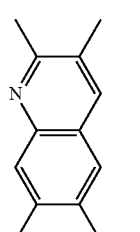
(410)

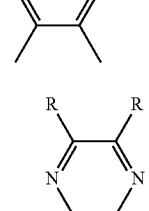
(411)

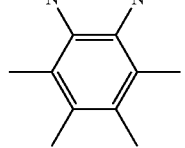
(412)

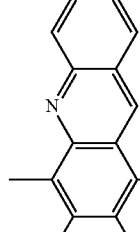
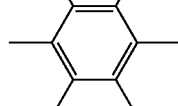
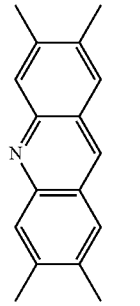
(413)

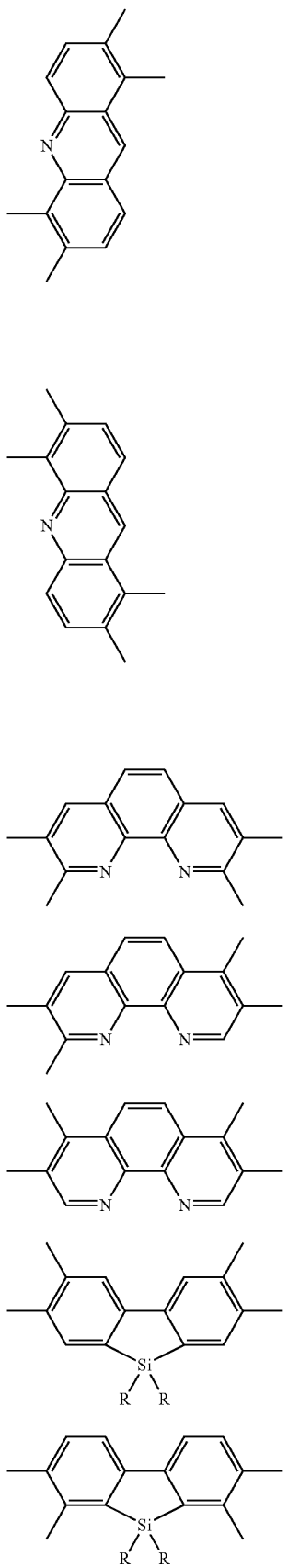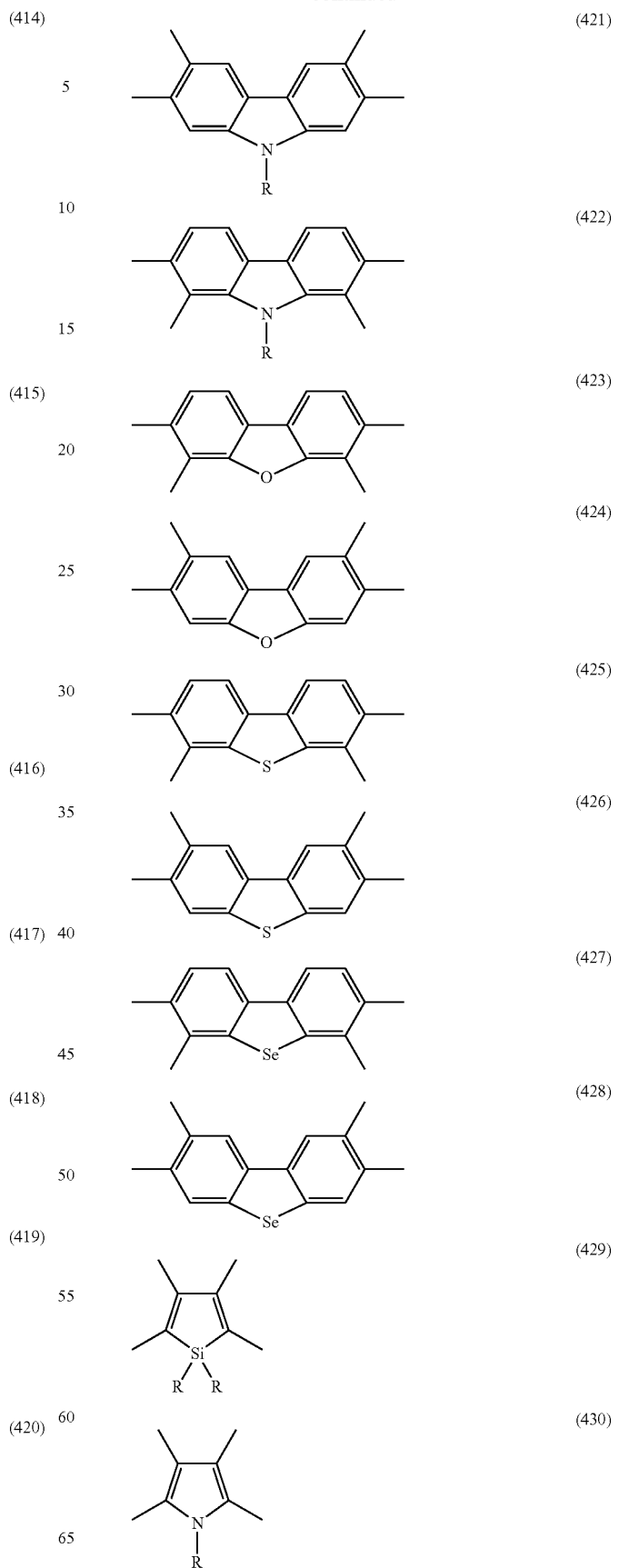

(431) 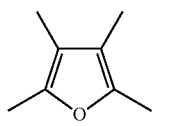
(432) 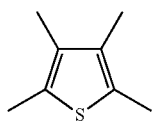
(433) 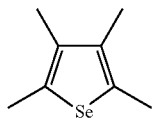
(434) 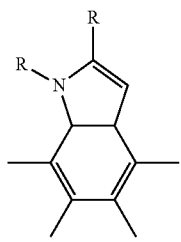
(435) 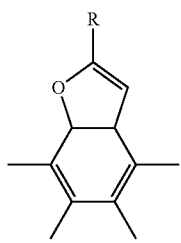
(436) 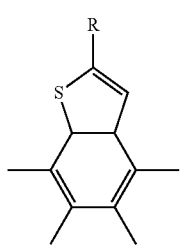
(437) 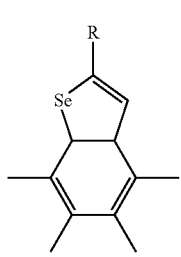
(438) 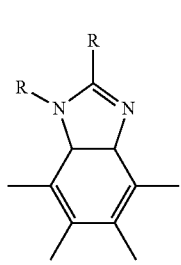
(439) 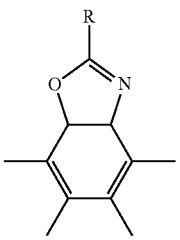
(440) 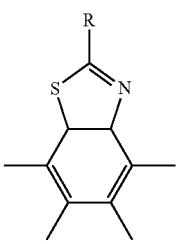
(441) 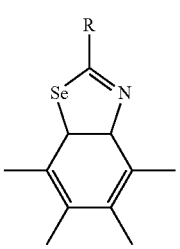
(442) 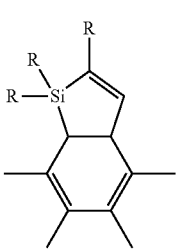
(443) 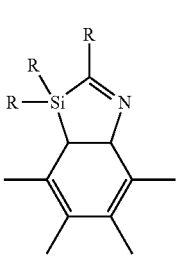
(444) 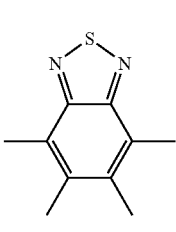
(445) 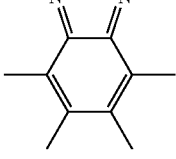

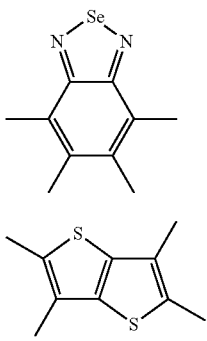

(446)

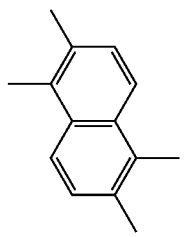

(451)

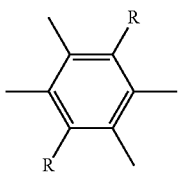

(447)

(wherein R represents the same meaning as described above.)

The tetra-valent aromatic carbocyclic group represented by Ar² denotes an atomic group remaining after removing four hydrogen atoms on an aromatic ring from an optionally substituted aromatic hydrocarbon. The tetra-valent aromatic carbocyclic group has a number of carbon atoms of usually 6 to 60, more preferably 6 to 20.

The substituent optionally carried on the aromatic hydrocarbon includes, for example, a halogen atom and a mono-valent group. The definition and specific examples of the mono-valent group are the same as the definition and specific examples of the mono-valent group represented by R.

The tetra-valent aromatic carbocyclic group includes, for example, groups represented by the formulae (448) to (454).

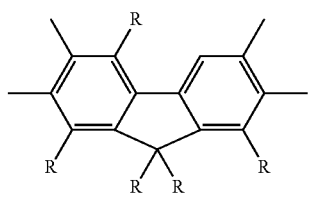

(452)

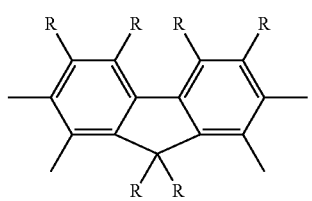

(453)

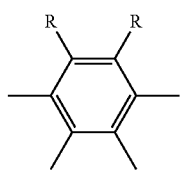

(454)

(448)

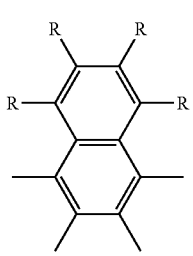

(449)

(450)

(wherein R represents the same meaning as described above.)

Among groups represented by the formulae (401) to (454), preferable from the standpoint of enhancing the photoelectric conversion efficiency of an organic film solar battery containing the polymer compound of the present invention are groups represented by the formula (401), the formula (402), the formula (404), the formula (405), the formula (406), the formula (411), the formula (412), the formula (430), the formula (431), the formula (432), the formula (433), the formula (444), the formula (445), the formula (446), the formula (447), the formula (448) and the formula (454), more preferable are groups represented by the formula (411), the formula (430), the formula (431), the formula (432), the formula (444), the formula (445), the formula (447) and the formula (448), further preferable are groups represented by the formula (411), the formula (432), the formula (444), the formula (447) and the formula (448), particularly preferable are groups represented by the formula (444) and the formula (448).

The constituent unit represented by the formulae (1) to (4) includes, for example, constituent units represented by the formulae (501) to (646).

(501) 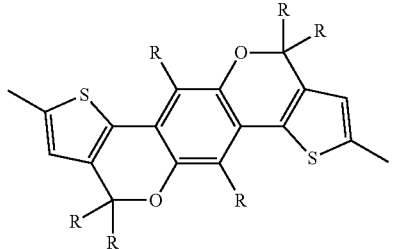
(502) 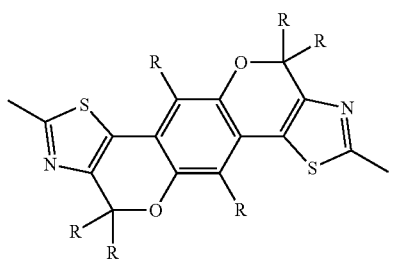
(503) 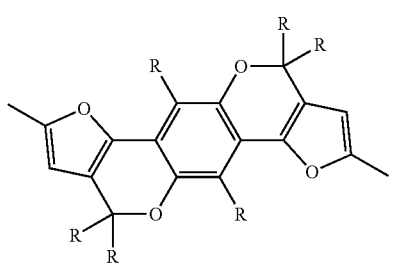
(504) 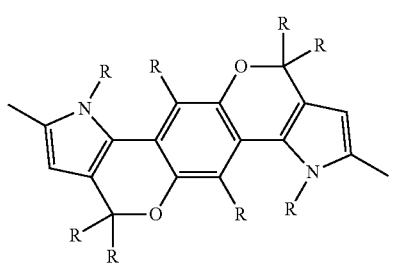
(505) 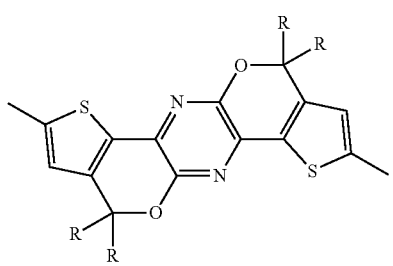
(506) 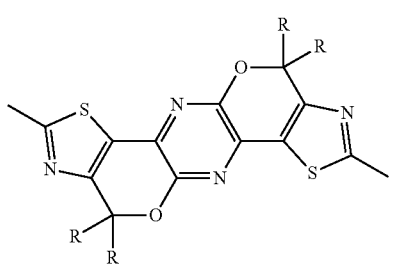
(507) 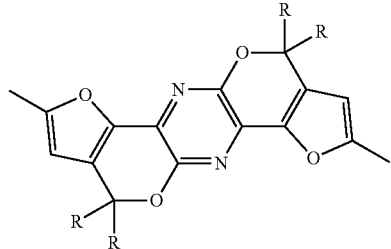
(508) 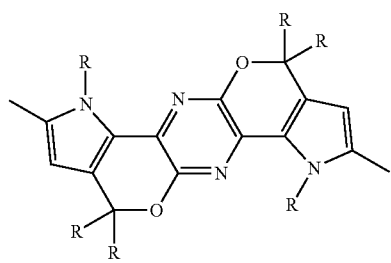
(509) 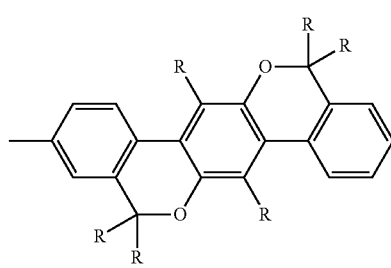
(510) 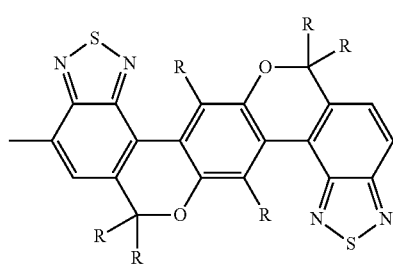
(511) 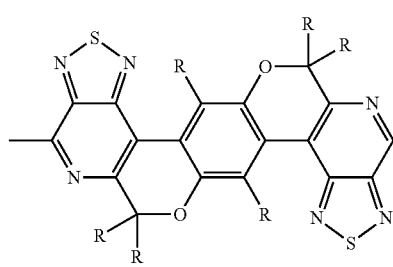
(512) 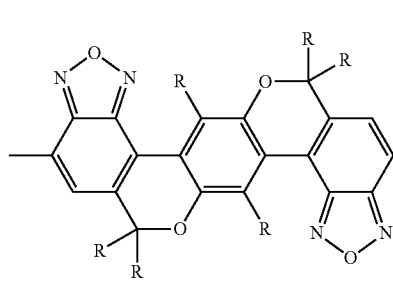

(513) 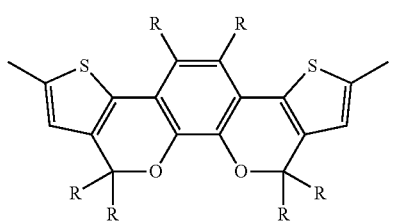
(514) 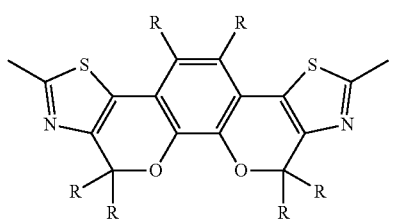
(515) 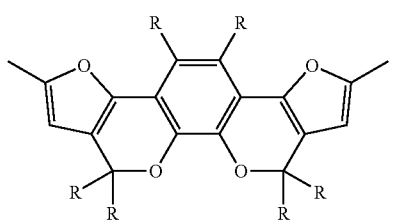
(516) 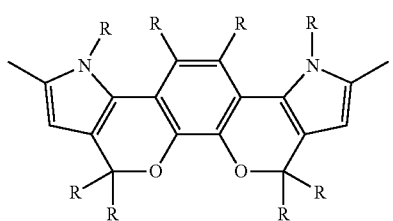
(517) 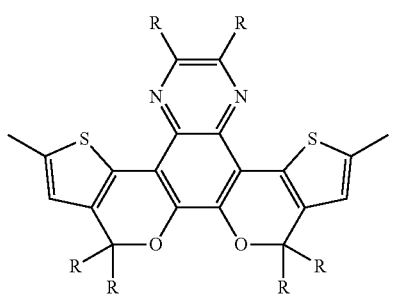
(518) 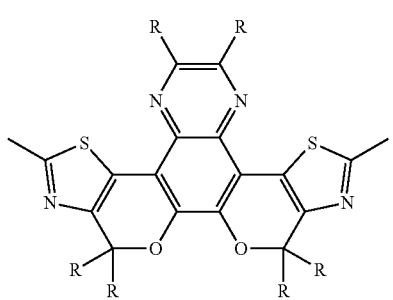
(519) 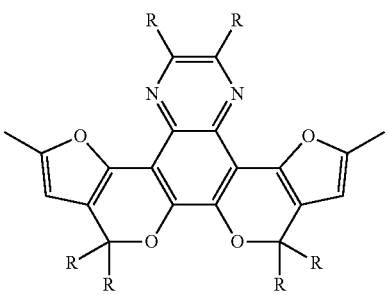
(520) 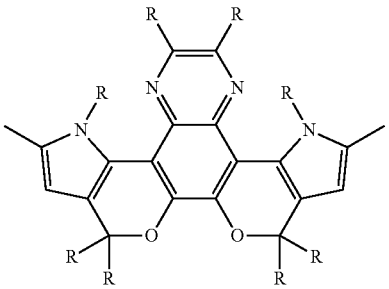
(521) 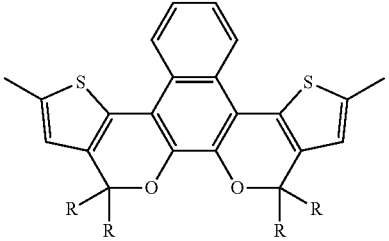
(522) 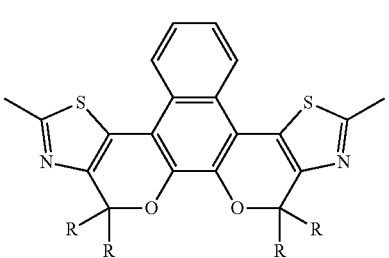
(523) 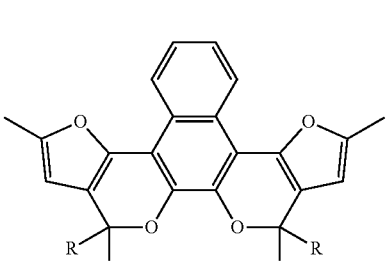
(524) 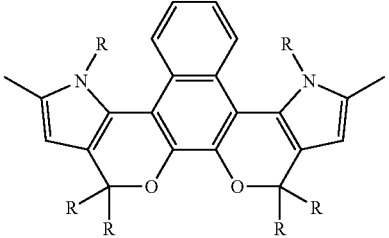

(525)
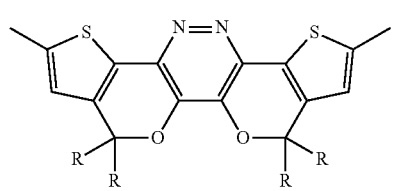
(526)
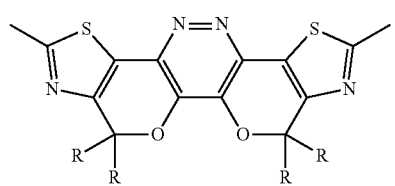
(527)
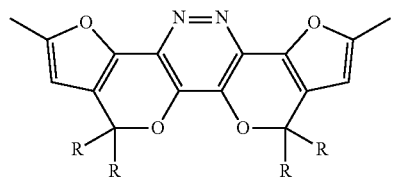
(528)
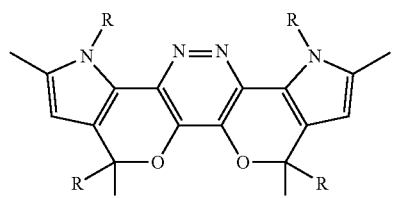
(529)
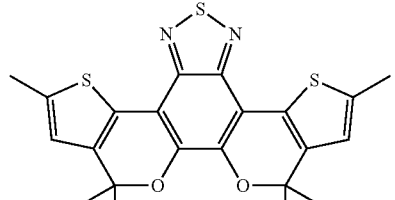
(530)
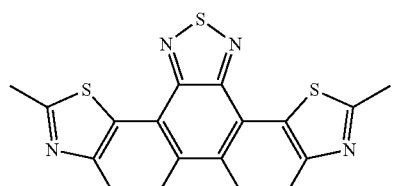
(531)
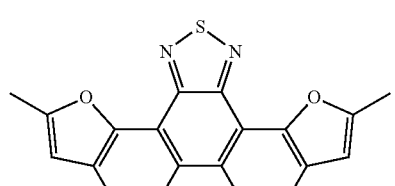
(532)
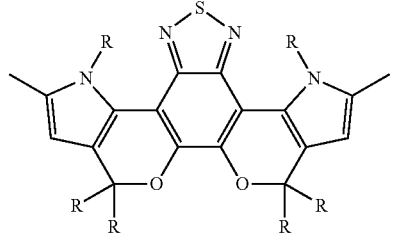
(533)
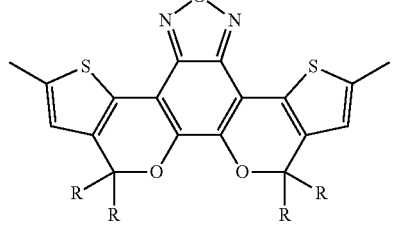
(534)
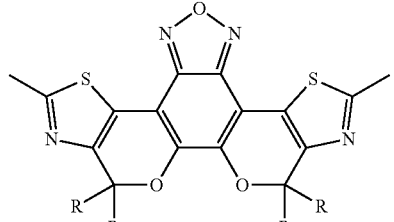
(535)
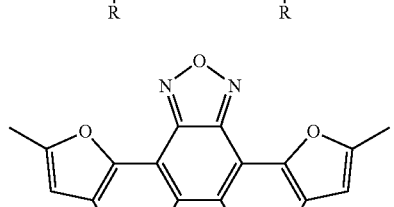
(536)
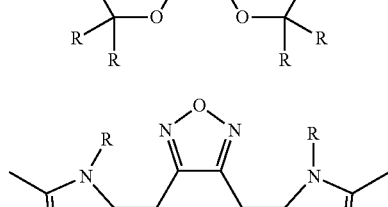
(537)
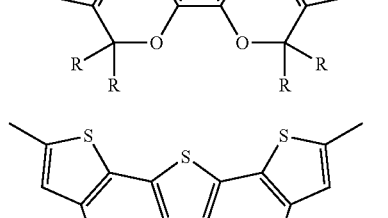
(538)
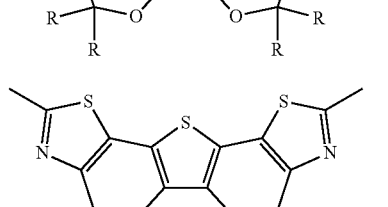

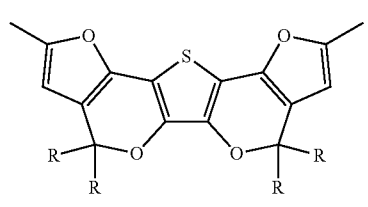 (539)
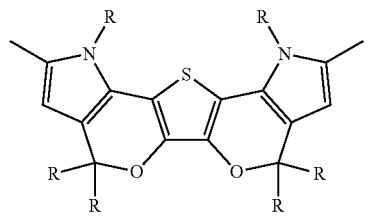 (540)
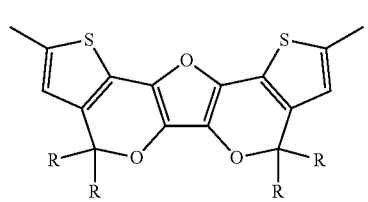 (541)
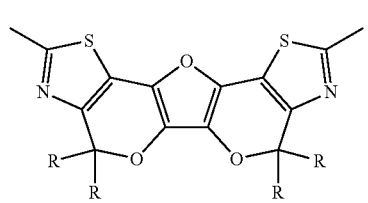 (542)
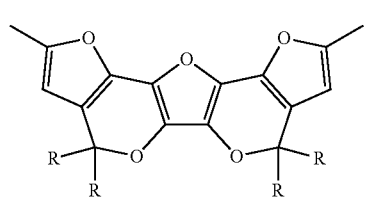 (543)
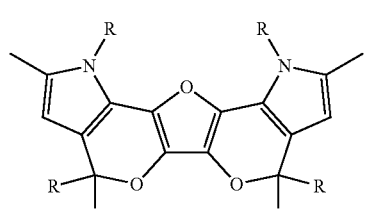 (544)
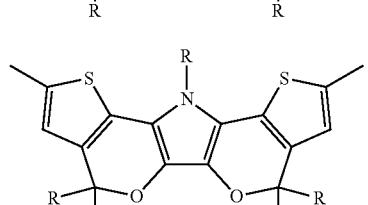 (545)
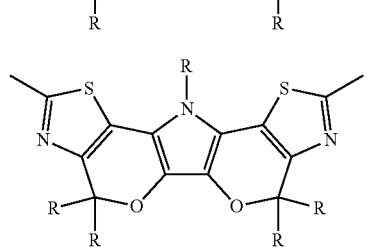 (546)
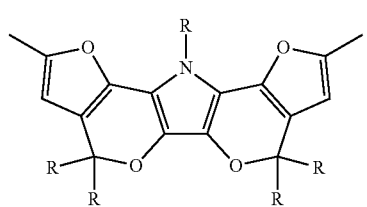 (547)
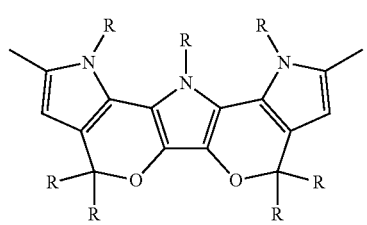 (548)
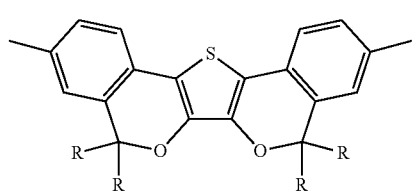 (549)
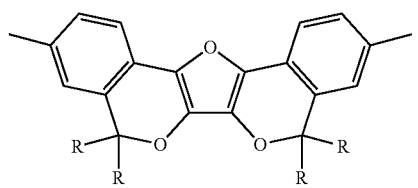 (550)
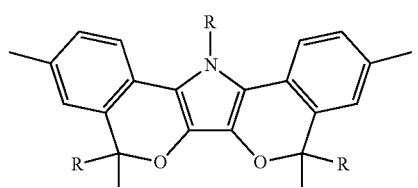 (551)
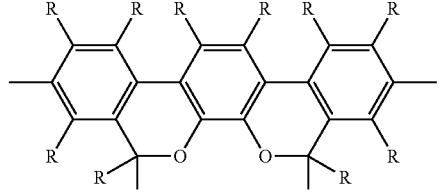 (552)
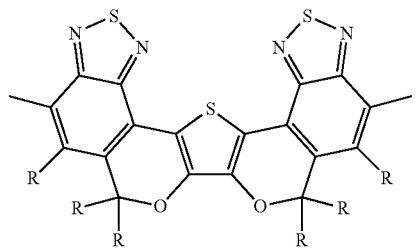 (553)

(554) 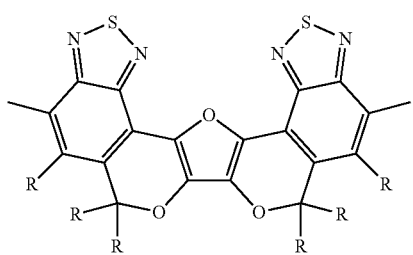
(555) 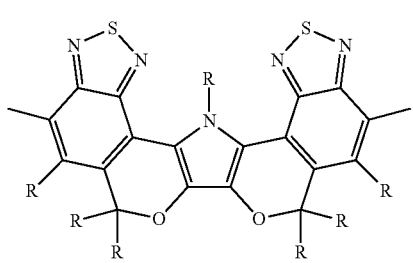
(556) 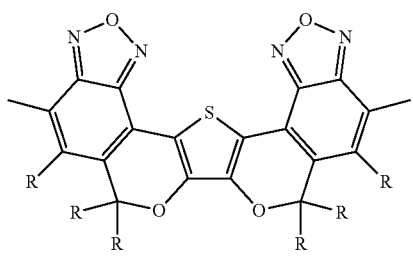
(557) 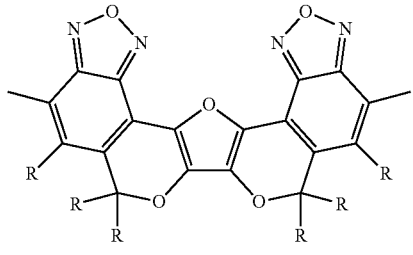
(558) 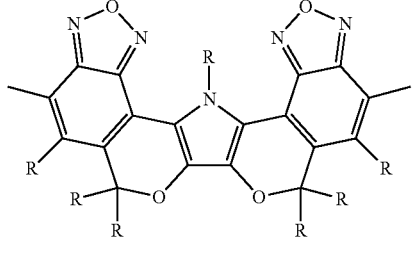
(559) 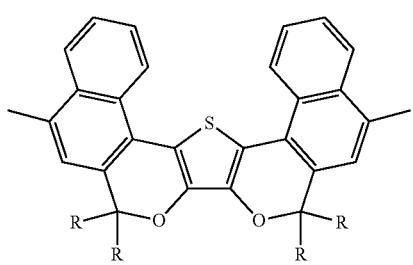
(560) 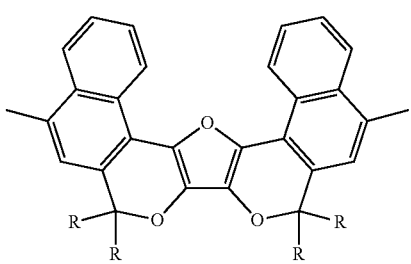
(561) 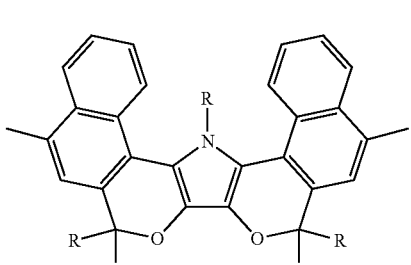
(562) 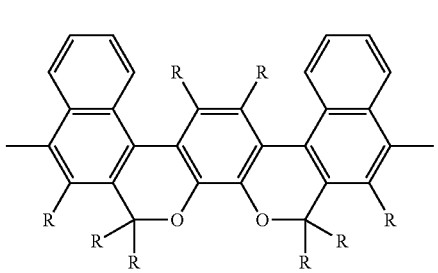
(563) 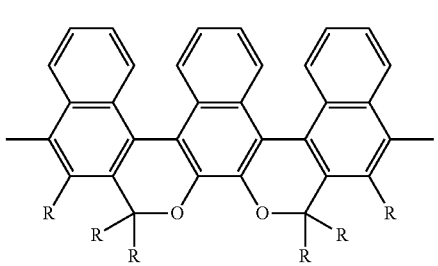
(564) 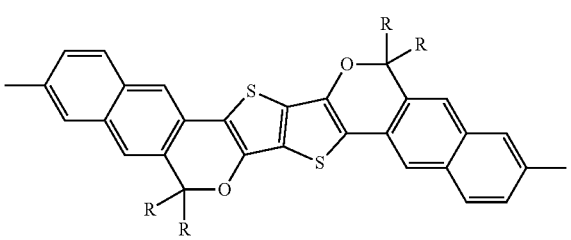
(565) 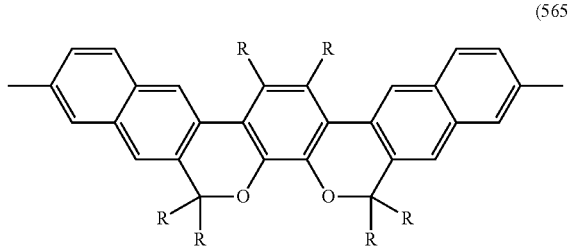

(566)
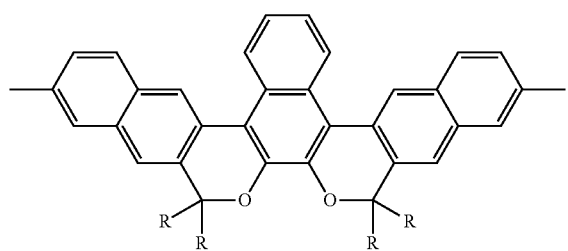
(567)
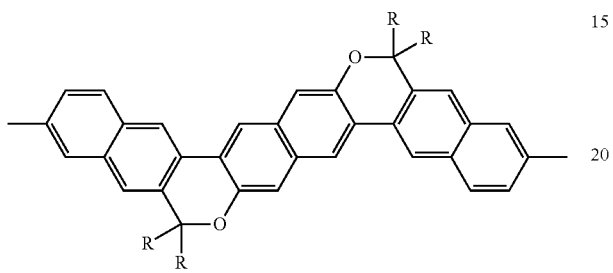
(568)
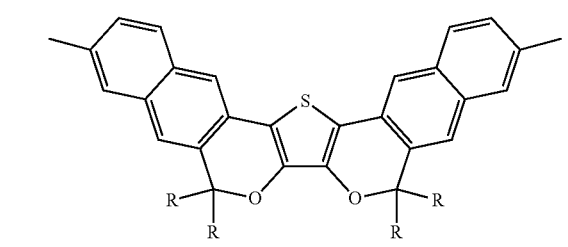
(569)
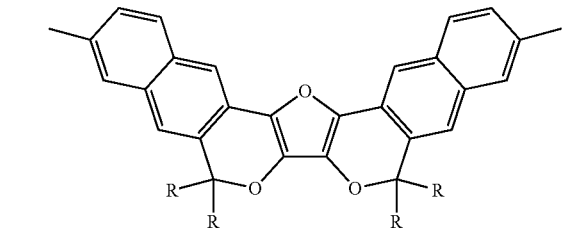
(570)
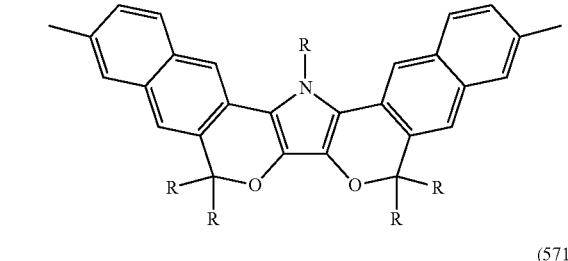
(571)
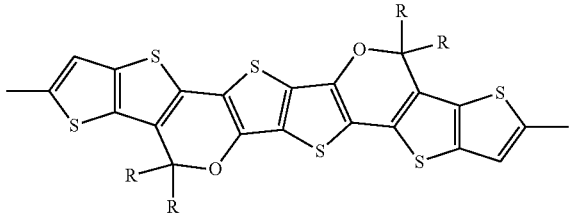
(572)
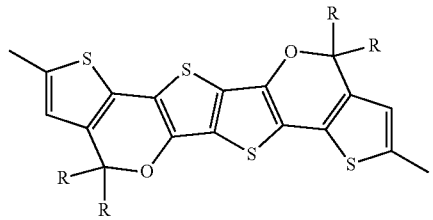
(573)
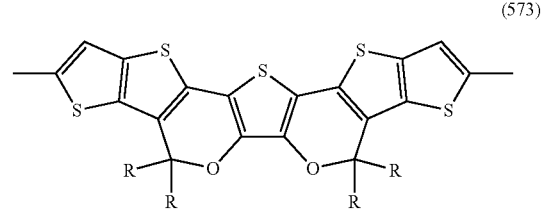
(574)
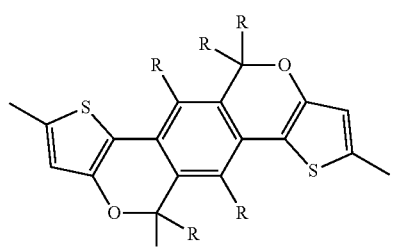
(575)
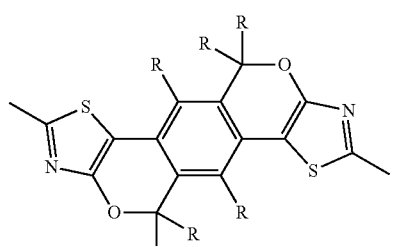
(576)
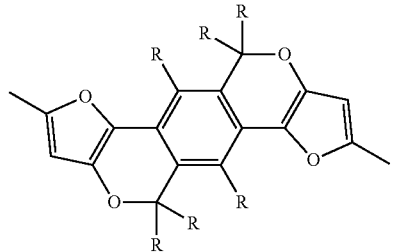
(577)
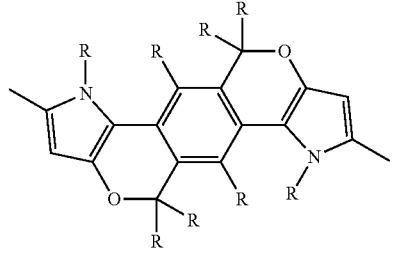

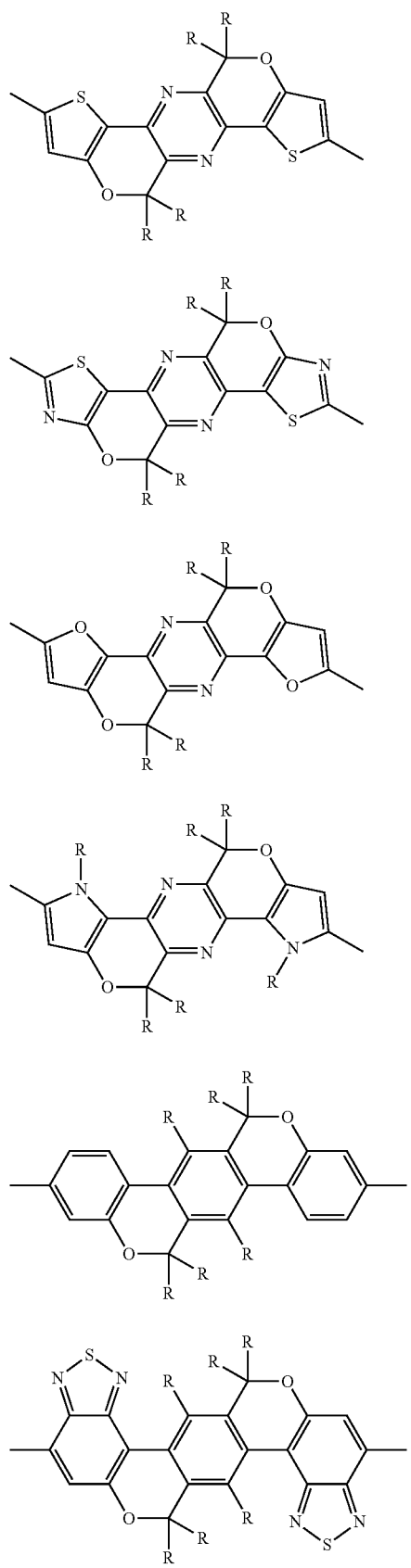
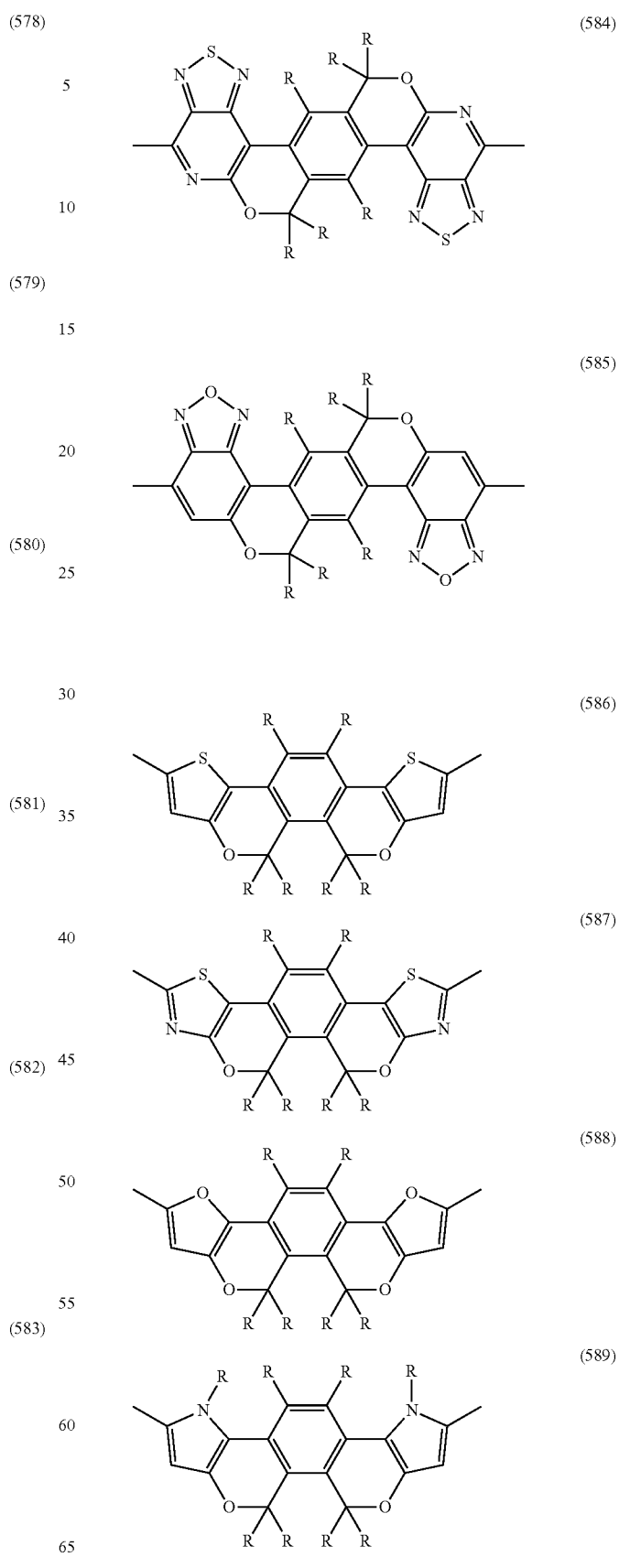

-continued
(590)
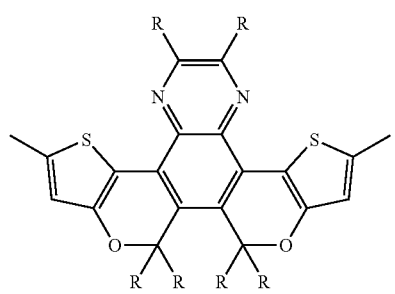
(591)
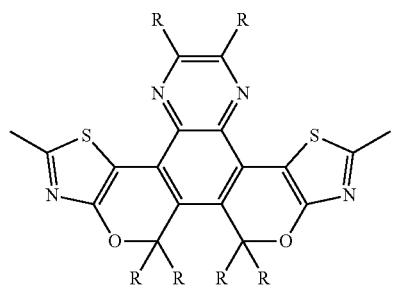
(592)
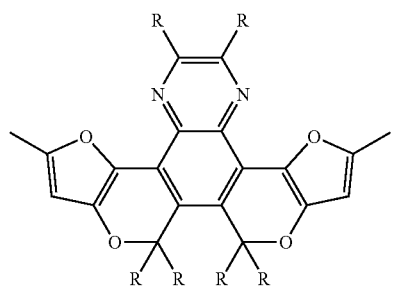
(593)
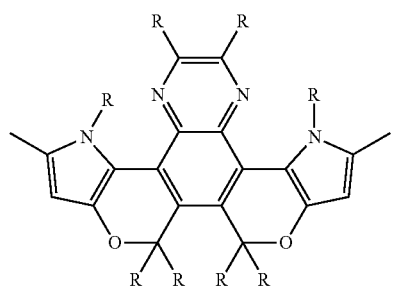
(594)
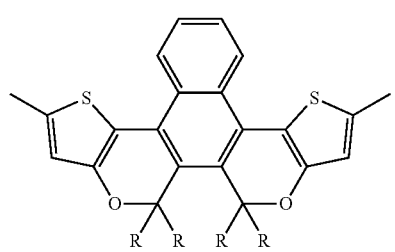
(595)
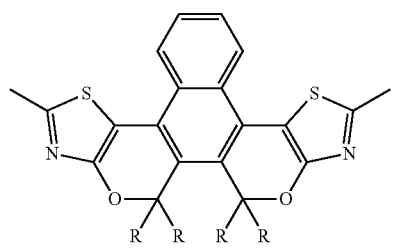
-continued
(596)
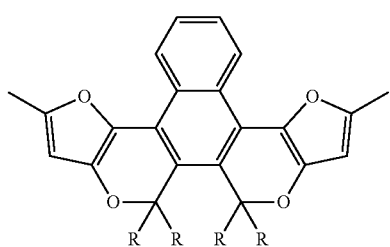
(597)
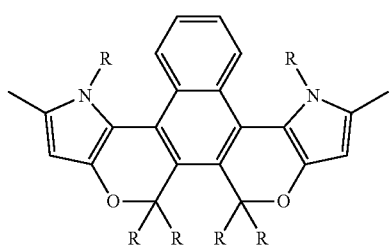
(598)
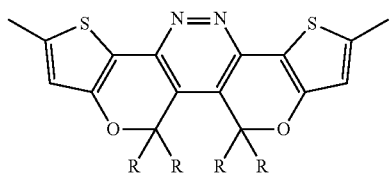
(599)
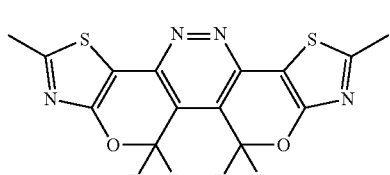
(600)
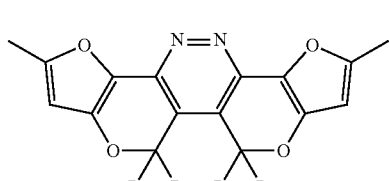
(601)
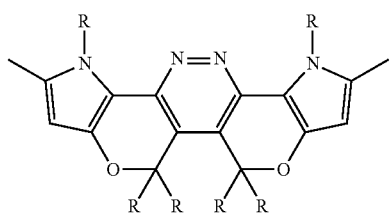
(602)
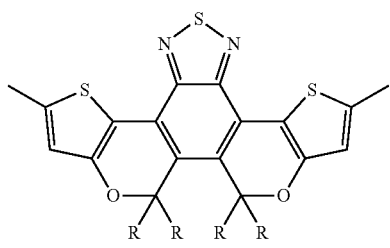

(603) 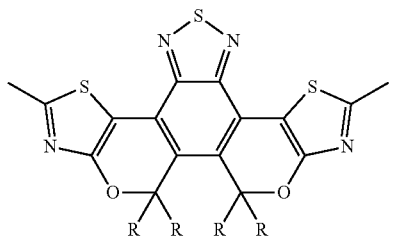
(604) 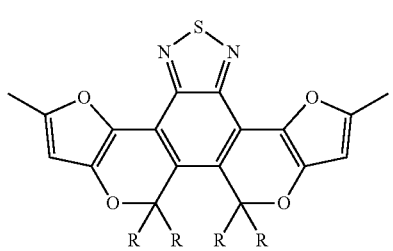
(605) 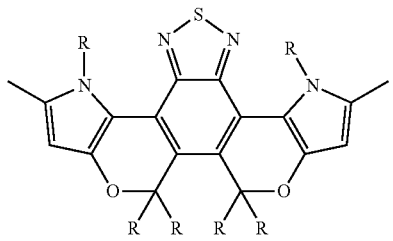
(606) 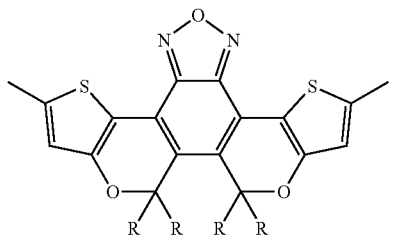
(607) 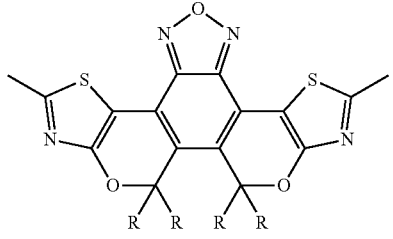
(608) 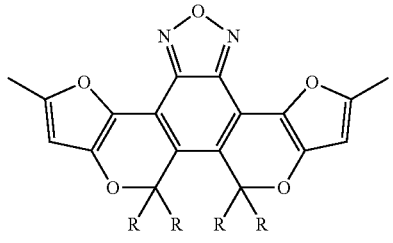
(609) 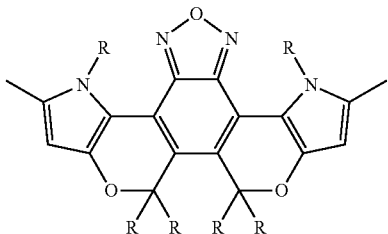
(610) 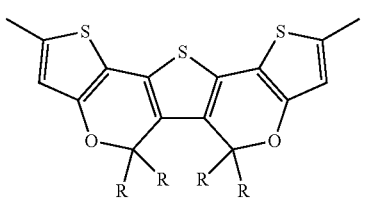
(611) 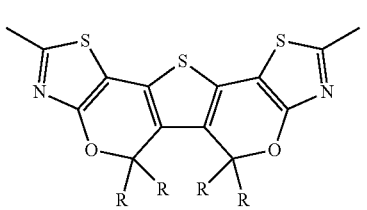
(612) 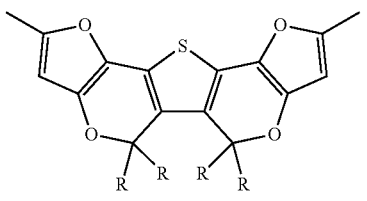
(613) 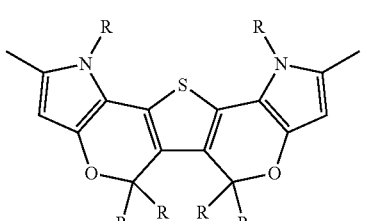
(614) 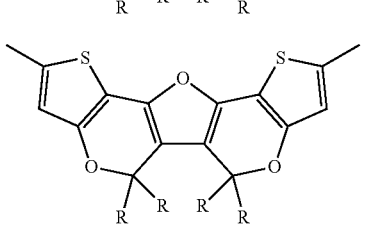
(615) 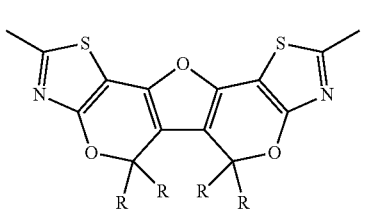

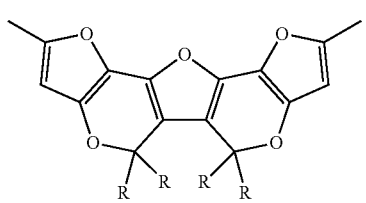
(616)
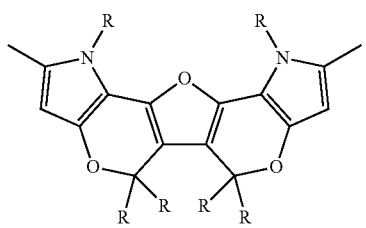
(617)
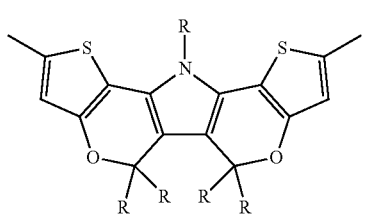
(618)
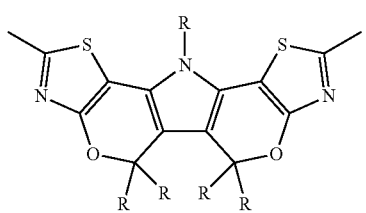
(619)
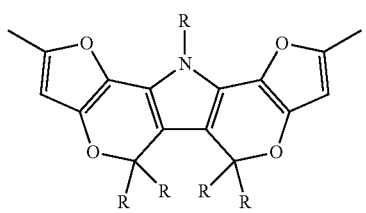
(620)
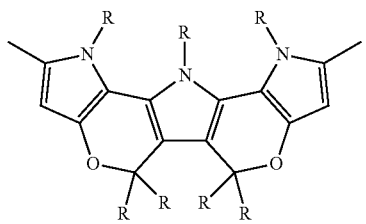
(621)
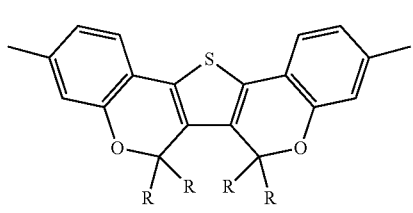
(622)
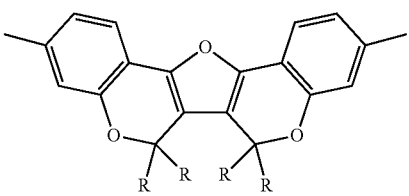
(623)
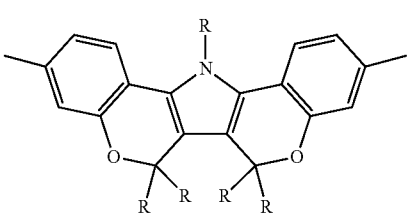
(624)
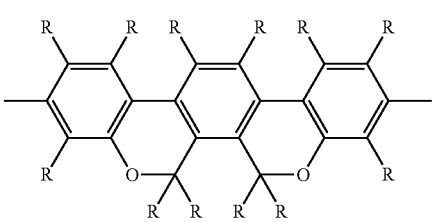
(625)
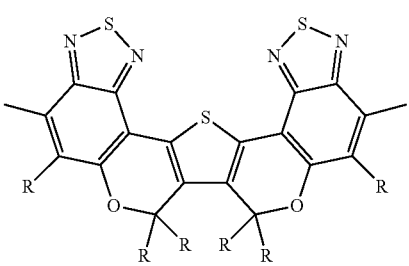
(626)
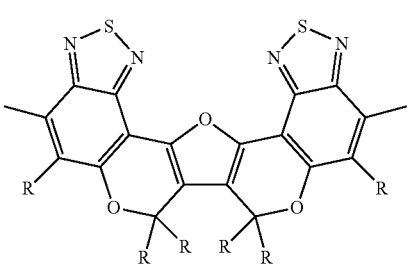
(627)
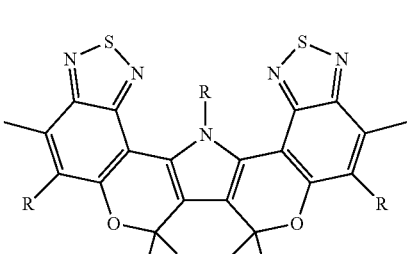
(628)

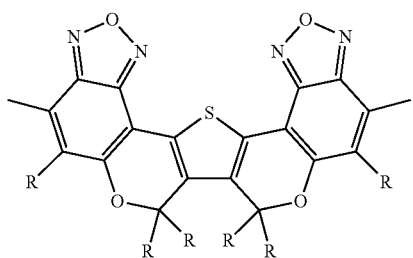
(629)
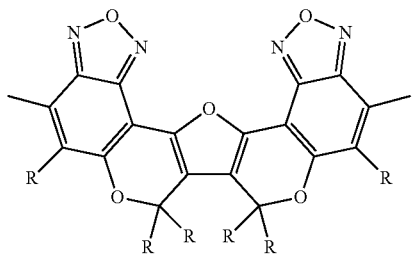
(630)
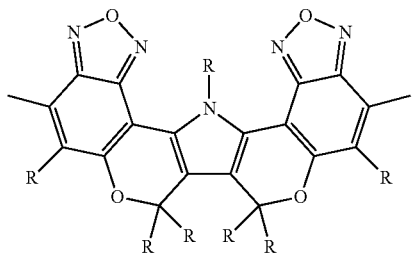
(631)
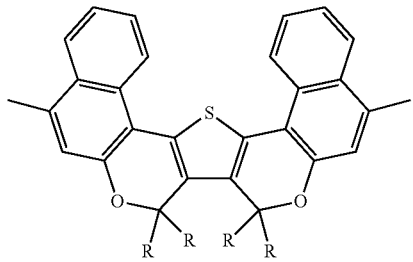
(632)
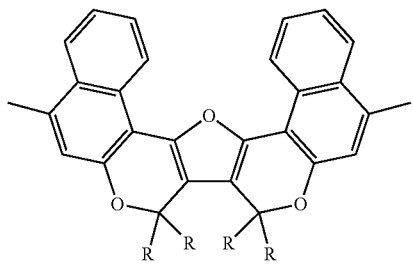
(633)
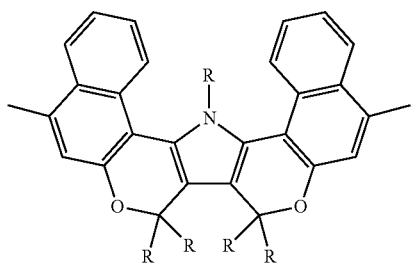
(634)
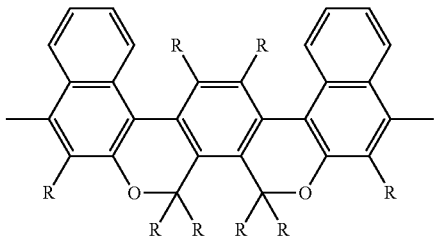
(635)
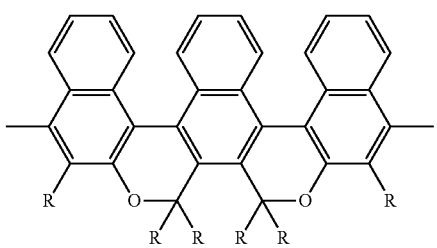
(636)
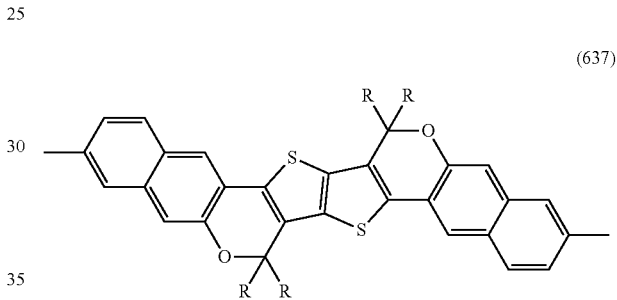
(637)
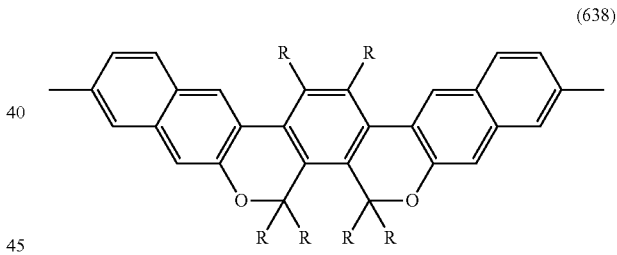
(638)
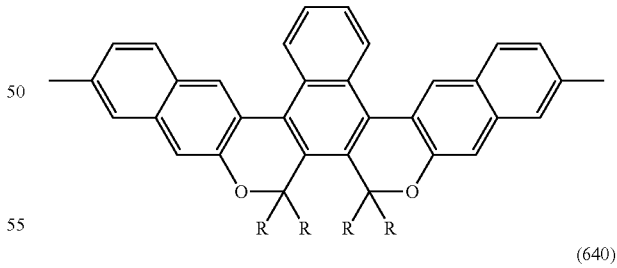
(639)
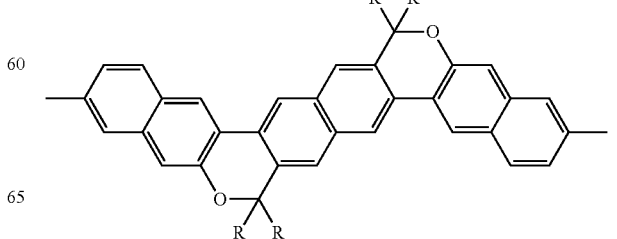
(640)

(641)
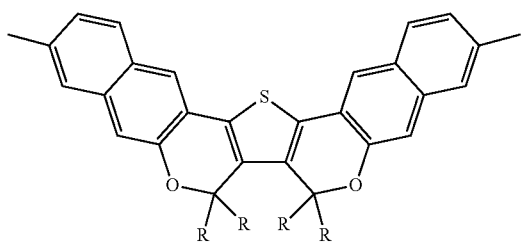

(642)
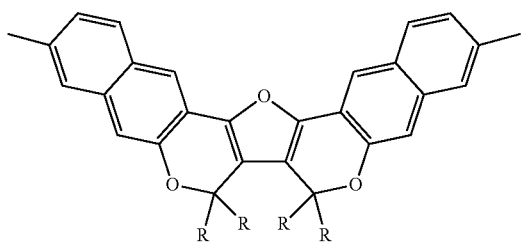

(643)
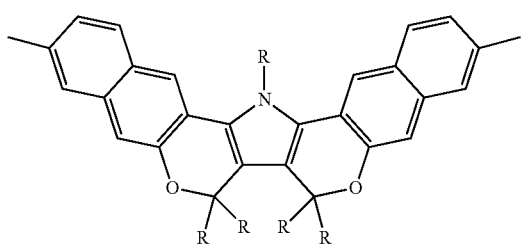

(644)
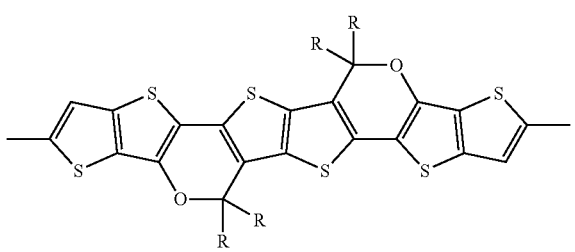

(645)
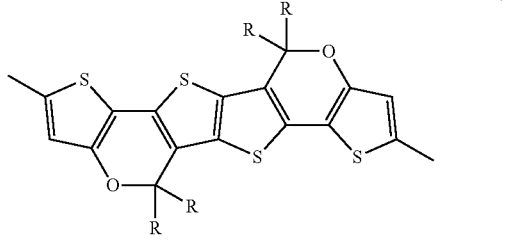

(646)
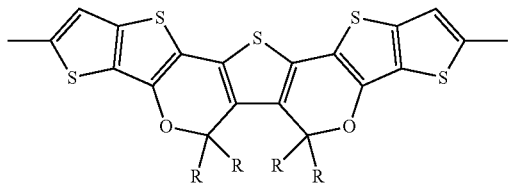

(wherein R represents the same meaning as described above.)

Among constituent units represented by the formulae (501) to (646), preferable from the standpoint of easiness of synthesis of monomers used as raw materials of the polymer compound of the present invention are constituent units represented by the formula (501), the formula (502), the formula (517), the formula (518), the formula (529), the formula (530), the formula (533), the formula (534), the formula (537), the formula (538), the formula (553), the formula (572), the formula (574), the formula (575), the formula (590), the formula (591), the formula (602), the formula (603), the formula (606), the formula (607), the formula (610), the formula (611), the formula (626) and the formula (645), more preferable are constituent units represented by the formula (501), the formula (517), the formula (529), the formula (537), the formula (553), the formula (572), the formula (574), the formula (590), the formula (602), the formula (610), the formula (626) and the formula (645), further preferable are constituent units represented by the formula (501), the formula (517), the formula (529), the formula (537), the formula (553), the formula (590), the formula (602) and the formula (610), particularly preferable are constituent units represented by the formula (501) and the formula (529).

The constituent unit represented by the formula (1), (2), (3) or (4) is preferably a constituent unit represented by the formula (5), the formula (6), the formula (7) or the formula (8), more preferably a constituent unit represented by the formula (9), the formula (10), the formula (11) or the formula (12), from the standpoint of enhancing the photoelectric conversion efficiency of an organic photoelectric conversion device containing the polymer compound of the present invention.

(5)
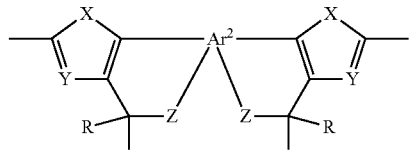

(6)
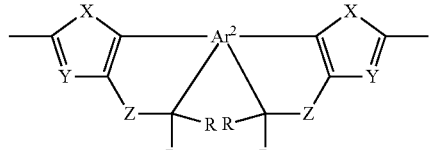

(7)
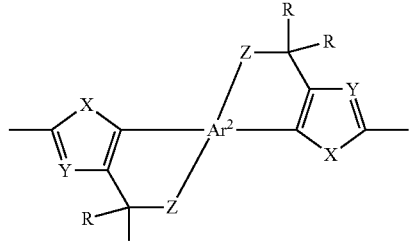

(8)
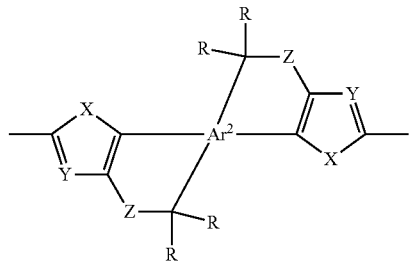

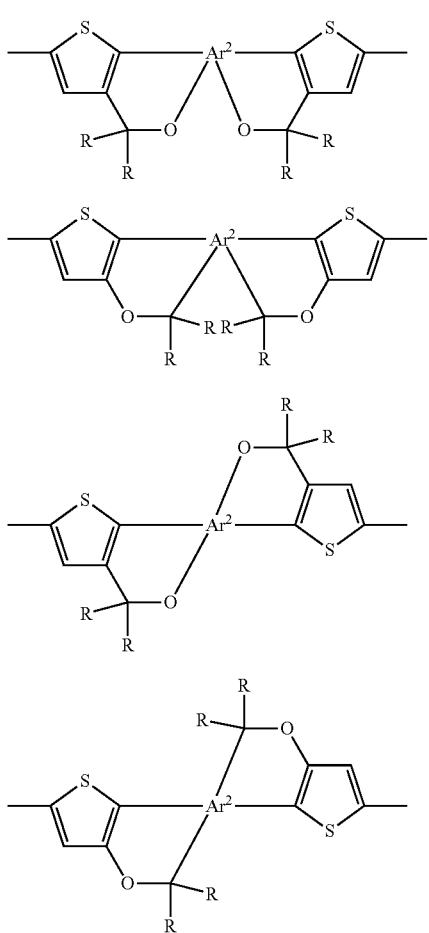

(9)
(10)
(11)
(12)

In the formulae (5) to (8), X represents a sulfur atom, an oxygen atom, a selenium atom, —NH— or —N(R)—. From the standpoint of enhancing the photoelectric conversion efficiency of an organic photoelectric conversion device containing the polymer compound of the present invention, a sulfur atom is preferable.

Y represents a nitrogen atom or =CH—. From the standpoint of enhancing the photoelectric conversion efficiency of an organic photoelectric conversion device containing the polymer compound of the present invention, =CH— is preferable.

It is preferable that the polymer compound of the present invention contains a constituent unit different from the constituent units represented by the formulae (1) to (4), in addition to the constituent units represented by the formulae (1) to (4). When the polymer compound of the present invention contains a constituent unit different from the constituent units represented by the formulae (1) to (4), it is preferable that the constituent unit represented by the formulae (1) to (4) and the constituent unit different from the constituent units represented by the formulae (1) to (4) form conjugation. Conjugation in the present invention means that unsaturated bonds are present sandwiching one single bond between them, thereby manifesting a mutual action. Here, the unsaturated bond denotes a double bond or a triple bond.

The constituent unit different from the constituent units represented by the formulae (1) to (4) includes arylene groups or di-valent heterocyclic groups different from the constituent units represented by the formulae (1) to (4).

The arylene group is an atomic group obtained by removing two hydrogen atoms on an aromatic ring from an optionally substituted aromatic hydrocarbon, and the arylene group has a number of carbon atoms of usually 6 to 60, preferably 6 to 20. The substituent includes, for example, a halogen atom and a mono-valent group. The definition and specific examples of the mono-valent group are the same as the definition and specific examples of the mono-valent group represented by R.

As the constituent unit different from the constituent units represented by the formulae (1) to (4), constituent units represented by the formulae (Cy-1) to (Cy-5) are preferable from the standpoint of enhancing the photoelectric conversion efficiency of an organic film solar battery containing the polymer compound of the present invention.

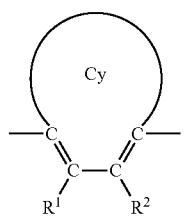

(Cy-1)

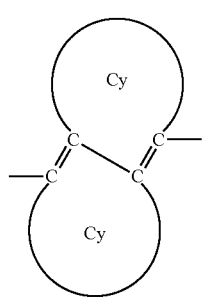

(Cy-2)

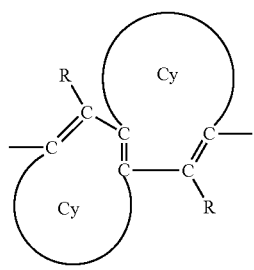

(Cy-3)

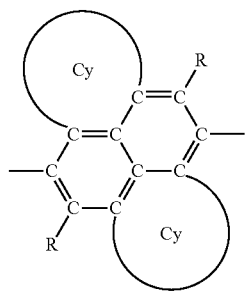

(Cy-4)

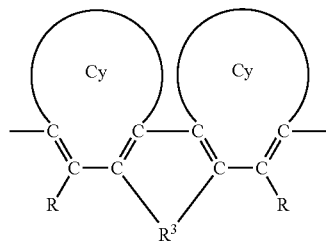
(Cy-5)

(in the formulae (Cy-1) to (Cy-5), R represents the same meaning as described above. $R^1$ and $R^2$ represent each independently a hydrogen atom, a halogen atom or a mono-valent group. $R^1$ and $R^2$ may be connected to form a cyclic structure. Rings Cy are the same or mutually different and represent an optionally substituted aromatic ring. $R^3$ represents a di-valent group.)

The definition and specific examples of the mono-valent group represented by $R^1$ and $R^2$ are the same as the definition and specific examples of the mono-valent group represented by R.

$R^1$ and $R^2$ may be connected to form a cyclic structure. Specific examples of the cyclic structure include structures represented by the formulae (D-1) to (D-5).

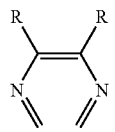
(D-1)

(D-2)

(D-3)

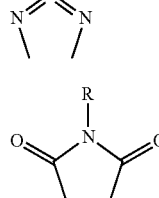
(D-4)

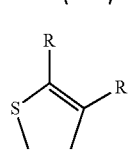
(D-5)

(in the formulae (D-1) to (D-5), R represents the same meaning as described above.)

The aromatic ring represented by the ring Cy may be a single ring or a condensed ring. The aromatic single ring includes, for example, a benzene ring, a pyrrole ring, a furan ring, a thiophene ring, an oxazole ring, a thiazole ring, a thiadiazole ring, a pyrazole ring, a pyridine ring, a pyrazine ring, an imidazole ring, a triazole ring, an isooxazole ring, an isothiazole ring, a pyrimidine ring, a pyridazine ring and a triazine ring.

The aromatic condensed ring includes aromatic rings obtained by condensing any ring with the above-described single ring. The ring to be condensed with the single ring includes, for example, a furan ring, a thiophene ring, a pyrrole ring, a pyrroline ring, a pyrrolidine ring, an oxazole ring, an isooxazole ring, a thiazole ring, an isothiazole ring, a thiadiazole ring, an imidazole ring, an imidazoline ring, an imidazolidine ring, a pyrazole ring, a pyrazoline ring, a pyrazolidine ring, a furazan ring, a triazole ring, a thiadiazole ring, an oxadiazole ring, a tetrazole ring, a pyran ring, a pyridine ring, a piperidine ring, a thiopyran ring, a ridazine ring, a pyrimidine ring, a pyrazine ring, a piperazine ring, a morpholine ring, a triazine ring, a benzofuran ring, an isobenzofuran ring, a benzothiophene ring, an indole ring, an isoindole ring, an indolizine ring, an indoline ring, an isoindoline ring, a chromene ring, a chromane ring, an isochromane ring, a benzopyran ring, a quinoline ring, an isoquinoline ring, a quinolizine ring, a benzoimidazole ring, a benzothiazole ring, an indazole ring, a naphthyridine ring, a quinoxaline ring, a quinazoline ring, a quinazolidine ring, a cinnoline ring, a phthalazine ring, a purine ring, a pteridine ring, a carbazole ring, a xanthene ring, a phenanthridine ring, an acridine ring, a β-carboline ring, a perimidine ring, a phenanthroline ring, a thianthrene ring, a phenoxathiin ring, a phenoxazine ring, a phenothiazine ring and a phenazine ring.

In the ring Cy, the substituent optionally carried on the aromatic ring includes, for example, a halogen atom and a mono-valent group. The definition and specific examples of the mono-valent group are the same as the definition and specific examples of the mono-valent group represented by R.

Specific examples of the of the di-valent group represented by $R^3$ include groups represented by the formulae (b-1) to (b-5).

(b-1)

(b-2)

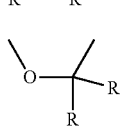
(b-3)

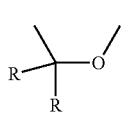
(b-4)

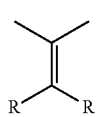
(b-5)

(in the formulae (b-1) to (b-5), R represents the same meaning as described above.)

The constituent units represented by the formulae (Cy-1) to (Cy-5) include, for example, constituent units represented by the formulae (C-1) to (C-29).

(C-1) 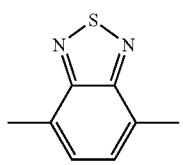
(C-2) 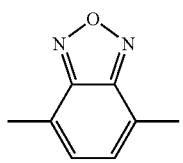
(C-3) 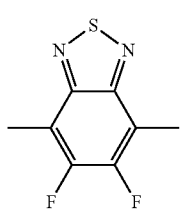
(C-4) 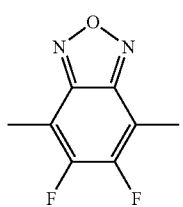
(C-5) 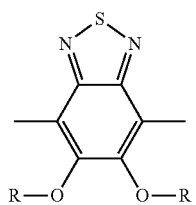
(C-6) 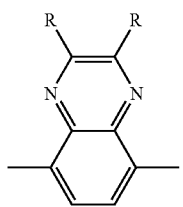
(C-7) 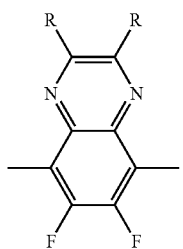
(C-8) 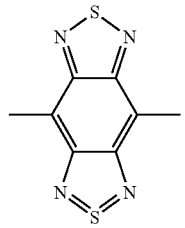
(C-9) 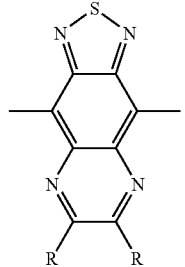
(C-10) 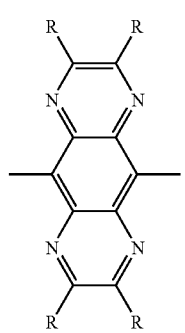
(C-11) 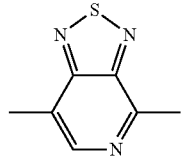
(C-12) 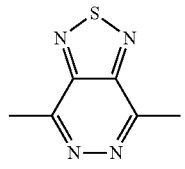
(C-13) 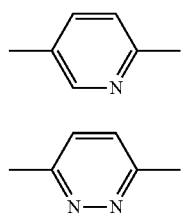
(C-14) 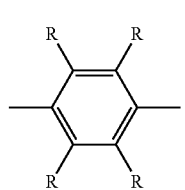
(C-15) 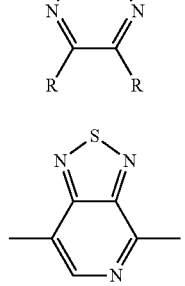

(C-16) 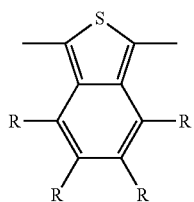
(C-17) 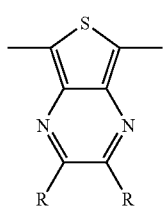
(C-18) 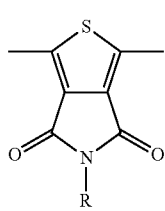
(C-19) 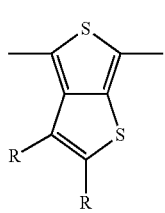
(C-20) 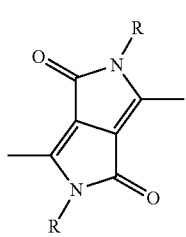
(C-21) 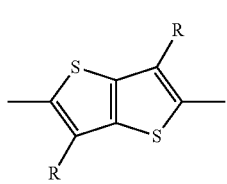
(C-22) 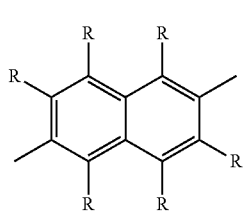
(C-23) 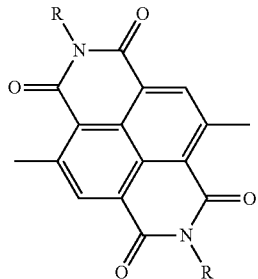
(C-24) 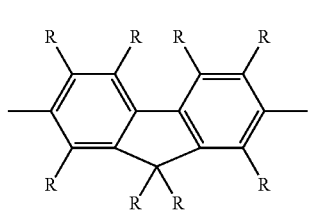
(C-25) 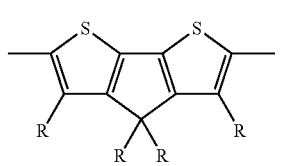
(C-26) 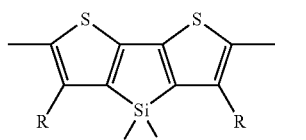
(C-27) 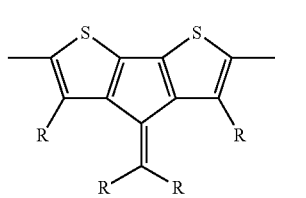
(C-28) 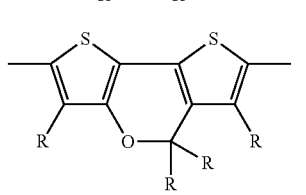
(C-29) 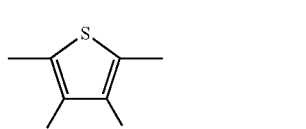
(in the formulae (C-1) to (C-29), R represents the same meaning as described above.)
The constituent unit represented by the formula (C-15) includes preferably a constituent unit represented by the formula (C-30) and a constituent unit represented by the formula (C-31).

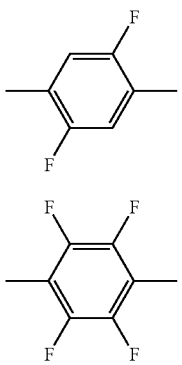

(C-30)

(C-31)

The polymer compound in the present invention denotes a compound having a weight-average molecular weight of 1000 or more. It is preferable that the weight-average molecular weight of the polymer compound of the present invention is 3000 to 10000000. When the weight-average molecular weight is smaller than 3000, a deficiency may be generated on a film formed in fabricating a device, and when larger than 10000000, solubility in a solvent and coatability in fabricating a device may lower. The weight-average molecular weight of the polymer compound is further preferably 4000 to 5000000, particularly preferably 5000 to 1000000.

The weight-average molecular weight in the present invention denotes a polystyrene-equivalent weight-average molecular weight calculated using a standard sample of polystyrene, by gel permeation chromatography (GPC). It is advantageous that at least one constituent unit represented by the formula (1), (2), (3) or (4) is contained in the polymer compound of the present invention. It is preferable that two or more constituent units on average are contained in one polymer chain, and it is further preferable that three or more constituent units on average are contained in one polymer chain.

When the polymer compound of the present invention is used in a device, it is desirable that the solubility of the polymer compound in a solvent is high since then fabrication of the device is easy. Specifically, the polymer compound of the present invention has preferably solubility by which a solution containing the polymer compound in an amount of 0.01 wt % or more can be prepared, more preferably solubility by which a solution containing the polymer compound in an amount of 0.1 wt % or more can be prepared, further preferably solubility by which a solution containing the polymer compound in an amount of 0.2 wt % or more can be prepared.

Though the method of producing the polymer compound of the present invention is not particularly restricted, the Suzuki coupling reaction and the Stille coupling reaction are preferably used from the standpoint of easiness of synthesis of the polymer compound.

The method of using the Suzuki coupling reaction includes, for example, a production method having a step of reacting at least one compound represented by the formula (100):

$$Q^{100}\text{-}E^1\text{-}Q^{200} \quad (100)$$

(wherein $E^1$ represents a constituent unit represented by the formulae (Cy-1) to (Cy-5). $Q^{100}$ and $Q^{200}$ are the same or mutually different and represent a dihydroxyboryl group (—B(OH)$_2$) or a borate residue.)
and at least one compound represented by the formula (200):

$$T^1\text{-}E^2\text{-}T^2 \quad (200)$$

(wherein $E^2$ represents a constituent unit represented by the formulae (1) to (4). $T^1$ and $T^2$ are the same or mutually different and represent a halogen atom.)

in the presence of a palladium catalyst and a base. $E^1$ represents preferably a constituent unit represented by the formulae (C-1) to (C-29).

When a compound represented by the formula (100) and a compound represented by the formula (200) are reacted, it is preferable that the total number of moles of at least one compound represented by the formula (200) used in the reaction is excess over the total number of moles of at least one compound represented by the formula (100). When the total number of moles of at least one compound represented by the formula (200) used in the reaction is 1 mol, the total number of moles of at least one compound represented by the formula (100) is preferably 0.6 to 0.99 mol, further preferably 0.7 to 0.95 mol.

The borate residue means a group obtained by removing a hydroxyl group from a boric acid diester, and specific examples thereof include groups represented by the following formulae.

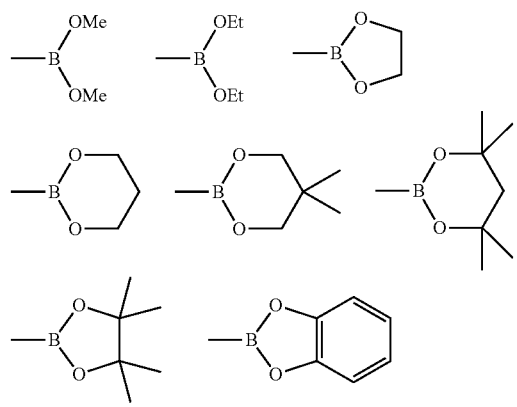

(wherein Me represents a methyl group and Et represents an ethyl group.)

The halogen atom represented by $T^1$ and $T^2$ in the formula (200) is a fluorine atom, a chlorine atom, a bromine atom or an iodine atom, and from the standpoint of easiness of synthesis of the polymer compound, a bromine atom and an iodine atom are preferable, a bromine atom is further preferable.

The method of conducting the Suzuki coupling reaction includes, specifically, a method of reacting in the presence of a base using a palladium catalyst as the catalyst in any solvent.

The palladium catalyst used in the Suzuki coupling reaction includes, for example, Pd(0) catalysts and Pd(II) catalysts, specifically palladium[tetrakis(triphenylphosphine)], palladium acetates, dichlorobis(triphenylphosphine)palladium, palladium acetate, tris(dibenzylideneacetone)dipalladium and bis(dibenzylideneacetone)palladium, and from the standpoint of easiness of the reaction (polymerization) operation and the reaction (polymerization) speed, preferable are dichlorobis(triphenylphosphine) palladium, palladium acetate and tris(dibenzylideneacetone)dipalladium.

The addition amount of the palladium catalyst is not particularly restricted, and amounts effective as the catalyst are permissible, however, the amount with respect to 1 mol of a compound represented by the formula (100) is usually 0.0001 mol to 0.5 mol, preferably 0.0003 mol to 0.1 mol.

When palladium acetates are used as the palladium catalyst to be used in the Suzuki coupling reaction, phosphorus compounds such as triphenylphosphine, tri(o-tolyl)phosphine, tri(o-methoxyphenyl)phosphine and the like can be added as a ligand. In this case, the addition amount of a ligand is usually 0.5 mol to 100 mol, preferably 0.9 mol to 20 mol, further preferably 1 mol to 10 mol with respect to 1 mol of the palladium catalyst.

The base to be used in the Suzuki coupling reaction includes inorganic bases, organic bases, inorganic salts and the like. The inorganic base includes, for example, potassium carbonate, sodium carbonate, barium hydroxide and potassium phosphate. The organic base includes, for example, triethylamine and tributylamine. The inorganic salt includes, for example, cesium fluoride.

The addition amount of the base is usually 0.5 mol to 100 mol, preferably 0.9 mol to 20 mol, further preferably 1 mol to 10 mol with respect to 1 mol of a compound represented by the formula (100).

The Suzuki coupling reaction is usually carried out in a solvent. As the solvent, exemplified are N,N-dimethylformamide, toluene, dimethoxyethane, tetrahydrofuran and methylene chloride. From the standpoint of solubility of the polymer compound used in the present invention, toluene and tetrahydrofuran are preferable. When a base is added, it may be permissible that an aqueous solution containing a base is added to a reaction solution, and the reaction is performed in a two-phase system composed of an aqueous phase and an organic phased. When an inorganic salt is used as the base, it is usual that an aqueous solution containing a base is added to a reaction solution and the reaction is performed, from the standpoint of solubility of the inorganic salt.

In the case of reacting in a two-phase system, a phase transfer catalyst such as quaternary ammonium salts and the like may be added, if required.

The temperature for conducting the Suzuki coupling reaction is usually 40 to 160° C., depending on the above-described solvent. The temperature is preferably 60 to 120° C., from the standpoint of increasing the molecular weight of the polymer compound. It may also be permissible that the temperature is raised up close to the boiling point of a solvent and reflux is performed. Though the time when the intended degree of polymerization is attained is defined as the end point, the reaction time is usually 0.1 hour to 200 hours. The reaction times around 0.5 hours to 30 hours are efficient and preferable.

The Suzuki coupling reaction is conducted in a reaction system not deactivating a palladium catalyst, under an inert atmosphere such as an argon gas, a nitrogen gas and the like. It is conducted, for example, in a system sufficiently deaerated with an argon gas, a nitrogen gas and the like. Specifically, an atmosphere in a polymerization vessel (reaction system) is deaerated by sufficiently purging with a nitrogen gas, then, a compound represented by the formula (100), a compound represented by the formula (200) and a palladium catalyst, for example, dichlorobis(triphenylphosphine)palladium(II) are charged into this polymerization vessel, further, an atmosphere in the polymerization vessel is deaerated by sufficiently purging with a nitrogen gas, then, a solvent deaerated by previously bubbling with a nitrogen gas, for example, toluene, is added, then, a base deaerated by previously bubbling with a nitrogen gas, for example, a sodium carbonate aqueous solution is dropped into this solution, then, the solution is heated and the temperature is raised, for example, up to the reflux temperature, and polymerization is carried out at this temperature for 8 hours while keeping an inert atmosphere.

The method of using the Stille coupling reaction includes, for example, a production method having a step of reacting at least one compound represented by the formula (300):

$$Q^{300}\text{-}E^3\text{-}Q^{400} \qquad (300)$$

(wherein $E^3$ represents a constituent unit represented by the formulae (Cy-1) to (Cy-5). $Q^{300}$ and $Q^{400}$ are the same or mutually different and represent a substituted stannyl group.) and a at least one compound represented by the formula (200) described above in the presence of a palladium catalyst. $E^3$ represents preferably a constituent unit represented by the formulae (C-1) to (C-29).

The substituted stannyl group includes a group represented by $-SnR^{100}{}_3$, and the like. Here, $R^{100}$ represents a mono-valent organic group. The mono-valent organic group includes, for example, an alkyl group and an aryl group.

The alkyl group includes linear alkyl groups such as a methyl group, an ethyl group, a propyl group, an isopropyl group, a butyl group, an isobutyl group, a sec-butyl group, a tert-butyl group, a pentyl group, an isopentyl group, a 2-methylbutyl group, a 1-methylbutyl group, a hexyl group, an isohexyl group, a 3-methylpentyl group, a 2-methylpentyl group, a 1-methylpentyl group, a heptyl group, an octyl group, an isooctyl group, a 2-ethylhexyl group, a nonyl group, a decyl group, an undecyl group, a dodecyl group, a tetradecyl group, a hexadecyl group, an octadecyl group, an eicosyl group and the like, and cycloalkyl groups such as a cyclopentyl group, a cyclohexyl group, an adamantyl group and the like. The aryl group includes a phenyl group, a naphthyl group and the like. The substituted stannyl group includes preferably $-SnMe_3$, $-SnEt_3$, $-SnBu_3$ and $SnPh_3$, more preferably $-SnMe_3$, $-SnEt_3$ and $SnBu_3$. In the above-described preferable examples, Me represents a methyl group, Et represents an ethyl group, Bu represents a butyl group and Ph represents a phenyl group.

Specific examples thereof include a method of reacting in any solvent in the presence of, for example, a palladium catalyst as the catalyst.

The palladium catalyst used in the Stille coupling reaction includes, for example, Pd(0) catalysts and Pd(II) catalysts. Specifically, palladium[tetrakis(triphenylphosphine)], palladium acetates, dichlorobis(triphenylphosphine)palladium, palladium acetate, tris(dibenzylideneacetone)dipalladium and bis(dibenzylideneacetone)palladium are mentioned, and from the standpoint of easiness of the reaction (polymerization) operation and the reaction (polymerization) speed, preferable are palladium[tetrakis(triphenylphosphine)] and tris(dibenzylideneacetone)dipalladium.

The addition amount of the palladium catalyst used in the Stille coupling reaction is not particularly restricted, and amounts effective as the catalyst are permissible, however, the amount with respect to 1 mol of a compound represented by the formula (100) is usually 0.0001 mol to 0.5 mol, preferably 0.0003 mol to 0.2 mol.

In the Stille coupling reaction, a ligand and a co-catalyst can also be used, if necessary. The ligand includes, for example, phosphorus compounds such as triphenylphosphine, tri(o-tolyl)phosphine, tri(o-methoxyphenyl)phosphine, tris(2-furyl)phosphine and the like, and arsenic compounds such as triphenylarsine, triphenoxyarsine and the like. The co-catalyst includes copper iodide, copper bromide, copper chloride, copper(I) 2-thenoate and the like.

In the case of use of a ligand or a co-catalyst, the addition amount of a ligand or a co-catalyst is usually 0.5 mol to 100 mol, preferably 0.9 mol to 20 mol, further preferably 1 mol to 10 mol with respect to 1 mol of a palladium catalyst.

The Stille coupling reaction is usually conducted in a solvent. The solvent includes N,N-dimethylformamide, N,N-dimethylacetamide, toluene, dimethoxyethane, tetrahydrofuran and the like. From the standpoint of solubility of the polymer compound used in the present invention, toluene and tetrahydrofuran are preferable.

The temperature for conducting the Stille coupling reaction is usually 50 to 160° C., depending on the solvent described above, however, from the standpoint of increasing the molecular weight of the polymer compound, it is preferably 60 to 120° C. It may also be permissible that the temperature is raised up close to the boiling point of a solvent and reflux is performed.

Though the time when the intended degree of polymerization is attained is defined as the end point, the time for effecting the above-described reaction (reaction time) is usually 0.1 hour to 200 hours. The reaction times around 1 hour to 30 hours are efficient and preferable.

The Stille coupling reaction is conducted in a reaction system not deactivating a Pd catalyst, under an inert atmosphere such as an argon gas, a nitrogen gas and the like. It is conducted, for example, in a system sufficiently deaerated with an argon gas, a nitrogen gas and the like. Specifically, an atmosphere in a polymerization vessel (reaction system) is deaerated by sufficiently purging with a nitrogen gas, then, a compound represented by the formula (300), a compound represented by the formula (200) and a palladium catalyst are charged into this polymerization vessel, further, an atmosphere in the polymerization vessel is deaerated by sufficiently purging with a nitrogen gas, then, a solvent deaerated by previously bubbling with a nitrogen gas, for example, toluene, is added, then, if necessary, a ligand and a co-catalyst are added, and thereafter, the solution is heated and the temperature is raised, for example, up to the reflux temperature, and polymerization is carried out at this temperature for 8 hours while keeping an inert atmosphere.

The polystyrene-equivalent number-average molecular weight of the polymer compound is preferably $1 \times 10^3$ to $1 \times 10^8$. When the polystyrene-equivalent number-average molecular weight is $1 \times 10^3$ or more, a tough film is obtained easily. While, when $10^8$ or lower, solubility is high and fabrication of a film is easy.

If a polymerization active group remains intact at the end of the polymer compound of the present invention, there is a possibility of lowering of the life and the property of a device obtained when the compound is used for fabrication of the device, therefore, it may be protected with a stable group. Those having a conjugated bond consecutive to the conjugated structure of the main chain are preferable, and for example, structures having a linkage to an aryl group or a heterocyclic group via a vinylene group may also be used.

The polymer compound of the present invention having a constituent unit represented by the formula (1), (2), (3) or (4) can be synthesized by using, for example, a compound represented by the formula (13) or a compound represented by the formula (14,) as one of raw materials.

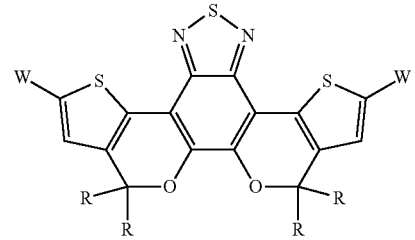

(13)

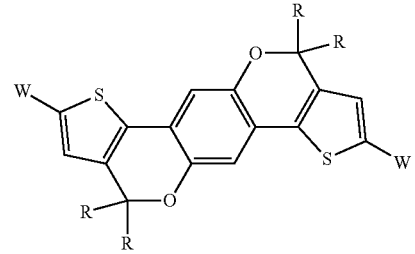

(14)

In the formula (13) and the formula (14), R represents the same meaning as described above. Four Rs may be the same or mutually different.

W represents a hydrogen atom, a halogen atom, a borate residue, a dihydroxyboryl group, a formyl group, a vinyl group or a substituted stannyl group. Two Ws may be the same or mutually different.

In the case of use of a compound represented by the formula (13) in which W represents a hydrogen atom, a polymer compound having a constituent unit represented by the formula (I) can be produced by oxidative polymerization. In oxidative polymerization, a catalyst is usually used. As the catalyst, known catalysts can be used. Use is made of, for example, a metal halide, and a mixture of a metal halide and an amine complex (metal halide/amine complex). As the metal halide, mono-valent, di-valent or tri-valent halides of metals such as copper, iron, vanadium, chromium and the like can be used.

The amine used for producing an amine complex includes, for example, pyridine, lutidine, 2-methylimidazole and N,N,N',N'-tetramethylethylenediamine. A metal halide/amine complex can be produced by mixing a metal halide and an amine in a solvent in the presence of oxygen, and the molar ratio of mixing a metal halide and an amine is, for example, metal halide/amine=1/0.1 to 1/200, preferably 1/0.3 to 1/100.

Iron chloride can also be used as a catalyst (Polym. Prep. Japan, Vol. 48, 309 (1999)). Further, the molecular weight of a polymer compound can be increased by using a copper/amine catalyst system (J. Org. Chem., 64, 2264 (1999), J. Polym. Sci. Part A, Polym. Chem., 37, 3702 (1999)).

The solvent in oxidative polymerization can be used without specific limitation providing it is a solvent with which a catalyst is not poisoned. The solvent includes, for example, hydrocarbon solvents, ether solvents and alcohol solvents. Here, the hydrocarbon solvent includes, for example, toluene, benzene, xylene, trimethylbenzene, tetramethylbenzene, naphthalene and tetralin. The ether solvent includes, for example, diethyl ether, diisopropyl ether, tetrahydrofuran, 1,4-dioxane, diphenyl ether and tert-butyl methyl ether. The alcohol solvent includes, for example, methanol, ethanol, isopropanol and 2-methoxyethanol.

The reaction temperature in oxidative polymerization is usually −100° C. to 100° C., preferably −50 to 50° C.

When the polymer compound of the present invention is a copolymer, the method of producing a copolymer includes a method of mixing two or more monomers and polymerizing them, a method of polymerizing one monomer, then, adding the second monomer, and the like. By using these methods or combining these methods, a block copolymer, a random copolymer, an alternate copolymer, a multi-block copolymer, a graft copolymer and the like can be produced.

From the standpoint of easiness of functional group transformation, it is preferable that Ws in the formula (13) and the formula (14) are the same or mutually different and represent a halogen atom, a borate residue, a dihydroxyboryl group and a substituted stannyl group.

When W in a compound represented by the formula (13) is a hydrogen atom, known methods can be used as a method for transforming W in a compound represented by the formula (13) into a bromine atom, and there is, for example, a method in which a compound represented by the formula (13) in which W represents a hydrogen atom is brought into contact with bromine or N-bromosuccinimide (NBS) and bromination thereof is effected. Bromination conditions can be arbitrarily set, and for example, a method of reacting with NBS in a solvent is desirable since the bromination ratio is high and selectivity of the position of introduction of a bromine atom is high in this method. The solvent used in this procedure includes N,N-dimethylformamide, chloroform, methylene chloride, carbon tetrachloride and the like. The reaction time is usually about 1 minute to 10 hours, and the reaction temperature is usually about −50° C. to 50° C. The amount of bromine to be used is preferably about 1 mol to 5 mol with respect to 1 mol of a compound represented by the formula (13) in which W represents a hydrogen atom. After the reaction, usual post treatments can be carried out such as, for example, adding water to stop the reaction, then, extracting the product with an organic solvent, distilling off the solvent, and the like, to obtain a compound represented by the formula (13) in which W represents a bromine atom. Isolation and purification of the product can be carried out by methods such as chromatographic fractionation, recrystallization and the like.

It is preferable for the polymer compound of the present invention that the light absorption terminal wavelength is a long wavelength. The light absorption terminal wavelength can be measured by the following method.

For measurement, use is made of a spectrophotometer functioning in a region of the wavelength of ultraviolet, visible and near-infrared (for example, ultraviolet visible near-infrared spectrophotometer JASCO-V670, manufactured by JASCO Corporation). Since the measurable wavelength range is from 200 to 1500 nm in the case of use of JASCO-V670, measurement is performed in this wavelength range. First, the absorption spectrum of a substrate used for measurement is measured. As the substrate, use is made of a quartz substrate, a glass substrate and the like. Then, on the substrate, a film containing a polymer compound is formed from a solution containing the polymer compound or a molten material containing the polymer compound. In film formation from a solution, drying is performed after the film formation. Thereafter, the absorption spectrum of a laminate of the film and the substrate is measured. The difference between the absorption spectrum of a laminate of the film and the substrate and the absorption spectrum of the substrate is regarded as the absorption spectrum of the film.

In the absorption spectrum of the film, the ordinate axis represents the absorbance of a polymer compound and the abscissa axis represents wavelength. It is desirable to regulate the thickness of a film so that the absorbance of the largest absorption peak is about 0.5 to 2. The absorbance of an absorption peak of the longest wavelength among absorption peaks is regarded as 100%, and an intersection point of a straight line parallel to the abscissa axis (wavelength axis) containing the 50% absorbance thereof and the absorption peak, situated at the longer side than the peak wavelength of the absorption peak, is defined as a first point. An intersection point of a straight line parallel to the wavelength axis containing the 25% absorbance thereof and the absorption peak, situated at the longer side than the peak wavelength of the absorption peak, is defined as a second point. An intersection point of the baseline and a straight line connecting the first point and the second point is defined as the light absorption terminal wavelength. With respect to the baseline, the absorbance of an absorption peak of the longest wavelength is regarded as 100%, and the wavelength of an intersection point of a straight line parallel to the wavelength axis containing the 10% absorbance thereof and the absorption peak, situated at the longer side than the peak wavelength of the absorption peak, is regarded as the basis, and a straight line connecting a third point on the absorption spectrum having wavelength longer by 100 nm than the basis wavelength and a fourth point on the absorption spectrum having wavelength longer by 150 nm than the basis wavelength is defined as the base line.

Since the polymer compound of the present invention can manifest high electron and/or hole transportability, when an organic film containing the polymer compound is used in a device, electrons and holes injected from an electrode or charges generated by light absorption can be transported. By utilizing such properties, the polymer compound can be suitably used in various electronic devices such as a photoelectric conversion device, an organic film transistor, an organic electroluminescent device and the like. These devices will be illustrated individually below.

A photoelectric conversion device containing the polymer compound of the present invention has at least one active layer containing the polymer compound of the present invention between a pair of electrodes at least one of which is transparent or semi-transparent.

A preferable embodiment of the photoelectric conversion device containing the polymer compound of the present invention has a pair of electrodes at least one of which is transparent or semi-transparent, and an active layer formed of an organic composition composed of a p-type organic semiconductor and an n-type organic semiconductor. The polymer compound of the present invention is preferably used as a p-type organic semiconductor.

The photoelectric conversion device produced by using the polymer compound of the present invention is usually formed on a substrate. This substrate may advantageously be one which does not chemically change in forming an electrode and in forming a layer of an organic material. The material of the substrate includes, for example, glass, plastic, polymer film and silicon. In the case of an opaque substrate, it is preferable that the opposite electrode, namely, an electrode which is more remote from the substrate is transparent or semi-transparent.

Another embodiment of the photoelectric conversion device containing the polymer compound of the present invention is a photoelectric conversion device containing a first active layer containing the polymer compound of the present invention, and a second active layer containing an electron accepting compound such as fullerene derivatives and the like adjacent to the first active layer, between a pair of electrodes at least one of which is transparent or semi-transparent.

The transparent or semi-transparent electrode material includes electrically conductive metal oxide films, semi-transparent metal films and the like. Specifically, use is made of electrically conductive materials composed of indium oxide, zinc oxide, tin oxide, and a composite thereof: indium•tin•oxide (ITO), indium•zinc•oxide and the like; NESA, gold, platinum, silver and copper, and preferable are ITO, indium•zinc•oxide and tin oxide. The electrode fabrication method includes a vacuum vapor deposition method, a sputtering method, an ion plating method, a plating method and the like.

As the electrode material, transparent electrically conductive films of organic materials such as polyaniline and derivatives thereof, polythiophene and derivatives thereof and the like may be used.

One electrode may not be transparent, and as the material of this electrode, metals, electrically conductive polymers and the like can be used. Specific examples of the electrode material include metals such as lithium, sodium, potassium, rubidium, cesium, magnesium, calcium, strontium, barium, aluminum, scandium, vanadium, zinc, yttrium, indium, cerium, samarium, europium, terbium, ytterbium and the like, and alloys composed of two or more of them and alloys composed of at least one of the above-described metals and at least one metal selected from the group consisting of gold, silver, platinum, copper, manganese, titanium, cobalt, nickel, tungsten and tin; graphite, graphite intercalation compounds, polyaniline and derivatives thereof, polythiophene and derivatives thereof. The alloy includes a magnesium-silver alloy, a magnesium-indium alloy, a magnesium-aluminum alloy, an indium-silver alloy, a lithium-aluminum alloy, a lithium-magnesium alloy, a lithium-indium alloy, a calcium-aluminum alloy and the like.

As the means for improving photoelectric conversion efficiency, an additional intermediate layer other than the active layer may be used. The material used as the intermediate layer includes halides of alkali metals and alkaline earth metals such as lithium fluoride and the like; oxides such as titanium oxide and the like; PEDOT (poly-3,4-ethylenedioxythiophene) and the like.

The active layer may contain the polymer compound of the present invention singly or may contain two or more of the polymer compounds of the present invention in combination. For enhancing hole transportability of the active layer, a compound other than the polymer compound of the present invention may be mixed in the active layer, as an electron donating compound and/or an electron accepting compound. The electron donating compound and the electron accepting compound are relatively determined based on the energy level of these compounds.

The electron donating compound includes, for example, pyrazoline derivatives, arylamine derivatives, stilbene derivatives, triphenyldiamine derivatives, oligothiophene and derivatives thereof, polyvinylcarbazole and derivatives thereof, polysilane and derivatives thereof, polysiloxane derivatives having an aromatic amine residue in the main chain or side chain, polyaniline and derivatives thereof, polythiophene and derivatives thereof, polypyrrole and derivatives thereof, polyphenylenevinylene and derivatives thereof, polythienylenevinylene and derivatives thereof, in addition to the polymer compound of the present invention.

The electron accepting compound includes, for example, carbon materials, metal oxides such as titanium oxide and the like, oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, metal complexes of 8-hydroxyquinoline and derivatives thereof, polyquinoline and derivatives thereof, polyquinoxaline and derivatives thereof, polyfluorene and derivatives thereof, phenanthroline derivatives such as 2,9-dimethyl-4,7-diphenyl-1,10-phenanthroline (basocuproine) and the like, fullerene and fullerene derivatives, in addition to the polymer compound of the present invention, and preferable are titanium oxide, carbon nano tubes, fullerene and fullerene derivatives, particularly preferable are fullerene and fullerene derivative.

The fullerene and fullerene derivatives include $C_{60}$, $C_{70}$, $C_{76}$, $C_{78}$, $C_{84}$ and derivatives thereof. The fullerene derivative means a compound obtained by at least partially modifying fullerene.

The fullerene derivative includes, for example, a compound represented by the formula (15), a compound represented the formula (16), a compound represented the formula (17) and a compound represented the formula (18).

(15)

(16)

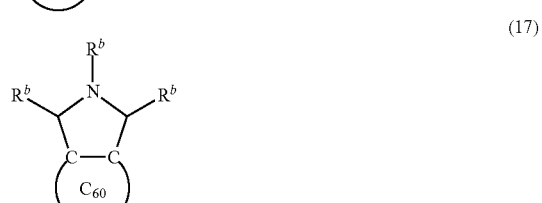

(17)

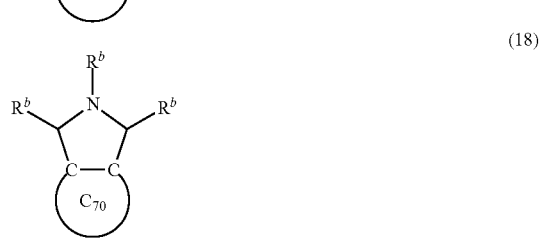

(18)

(in the formulae (15) to (18), $R^a$ represents an optionally substituted alkyl group, an aryl group, an aromatic heterocyclic group or a group having an ester structure. A plurality of $R^a$s may be the same or mutually different. $R^b$ represents an optionally substituted alkyl group or an aryl group. A plurality of $R^b$s may be the same or mutually different.)

The definition and specific examples of the optionally substituted alkyl group and aryl group represented by $R^a$ and $R^b$ are the same as the definition and specific examples of the optionally substituted alkyl group and aryl group represented by R.

The aromatic heterocyclic group represented by $R^a$ includes, for example, a thienyl group, a pyrrolyl group, a furyl group, a pyridyl group, a quinolyl group and an isoquinolyl group.

The group having an ester structure represented by $R^a$ includes, for example, a group represented by the formula (19).

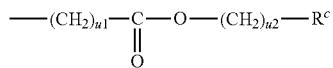
(19)

(wherein u1 represents an integer of 1 to 6, u2 represents an integer of 0 to 6, and $R^c$ represents an optionally substituted alkyl group, an aryl group or an aromatic heterocyclic group.)

The definition and specific examples of the optionally substituted alkyl group, aryl group and aromatic heterocyclic group represented by $R^c$ are the same as the definition and specific examples of the optionally substituted alkyl group, aryl group and aromatic heterocyclic group represented by $R^a$.

Specific examples of the $C_{60}$ fullerene derivatives include the following compounds.

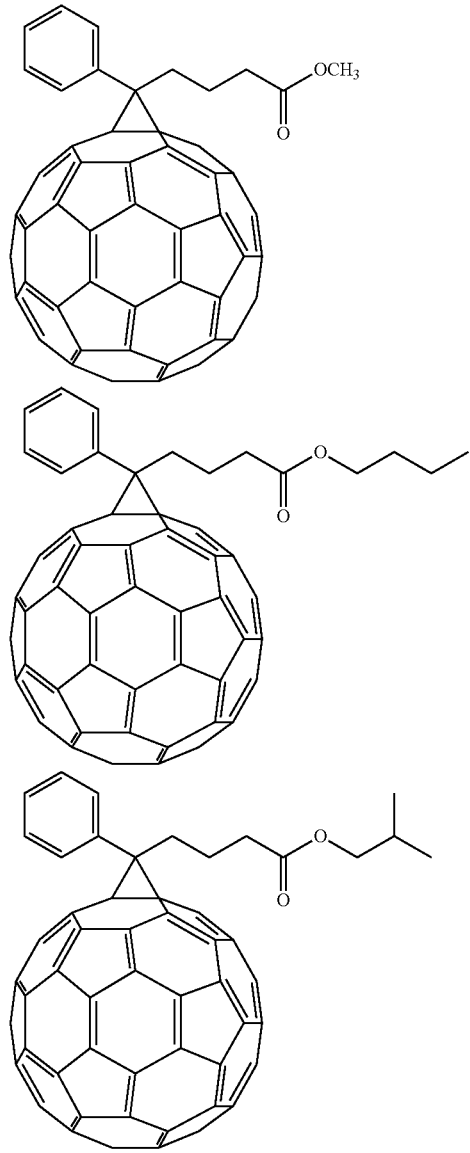

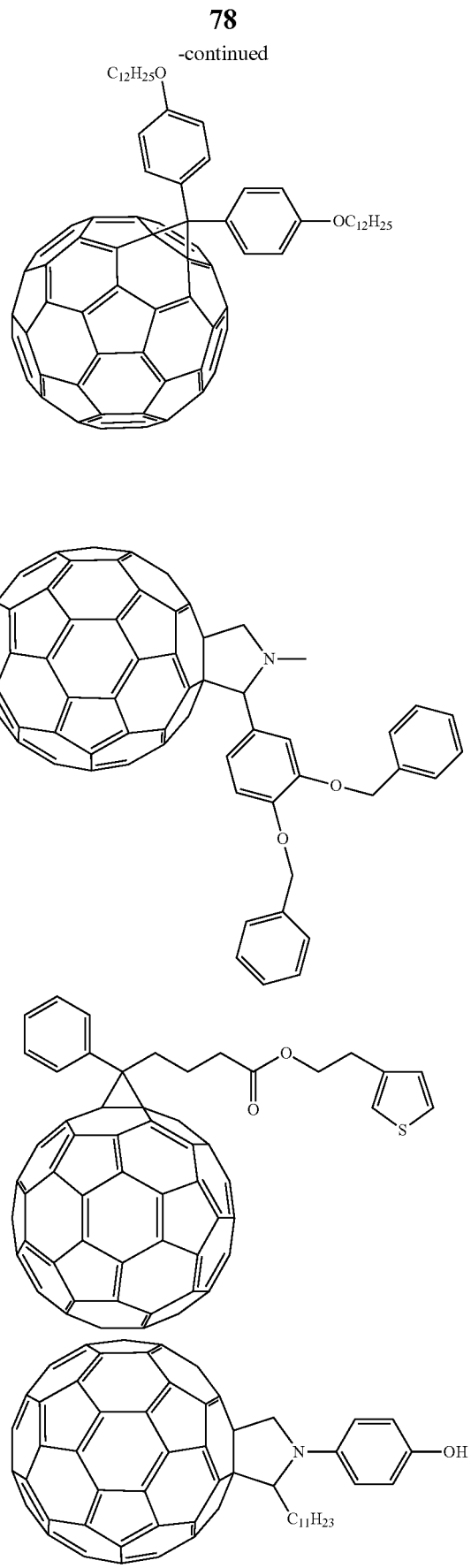

Specific examples of the C$_{70}$ fullerene derivatives include the following compounds.

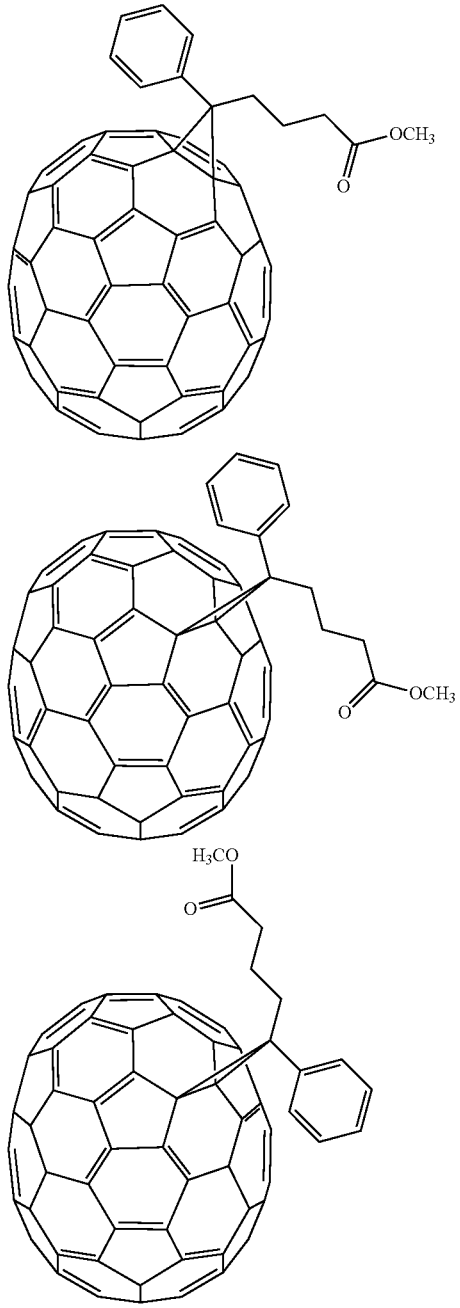

Examples of the fullerene derivatives include [6,6]-phenyl-C61 butyric acid methyl ester (C60PCBM, [6,6]-Phenyl C61 butyric acid methyl ester), [6,6]-phenyl-C71 butyric acid methyl ester (C70PCBM, [6,6]-Phenyl C71 butyric acid methyl ester), [6,6]-phenyl-C85 butyric acid methyl ester (C84PCBM, [6,6]-Phenyl C85 butyric acid methyl ester) and [6,6]-thienyl-C61 butyric acid methyl ester ([6,6]-Thienyl C61 butyric acid methyl ester).

When the active layer contains the polymer compound of the present invention and a fullerene derivative, the amount of the fullerene derivative is preferably 10 to 1000 parts by weight, more preferably 20 to 500 parts by weight, with respect to 100 parts by weight of the polymer compound of the present invention.

The thickness of the active layer is usually preferably 1 nm to 100 µm, more preferably 2 nm to 1000 nm, further preferably 5 nm to 500 nm, more preferably 20 nm to 200 nm.

The active layer may be produced by any method and the production method thereof includes, for example, methods of film formation from a solution containing a polymer compound and methods of film formation by vacuum vapor deposition.

A preferable method of producing a photoelectric conversion device is a production method of a device having a first electrode and a second electrode and an active layer between the first electrode and the second electrode, comprising a step of coating a solution (ink) containing the polymer compound of the present invention and a solvent by a coating method to form the active layer on the first electrode and a step of forming the second electrode on the active layer.

The solvent used for film formation from a solution may advantageously be one which dissolves the polymer compound of the present invention. The solvent includes, for example, unsaturated hydrocarbon solvents such as toluene, xylene, mesitylene, tetralin, decalin, bicyclohexyl, butylbenzene, sec-butylbenzene, tert-butylbenzene and the like, halogenated saturated hydrocarbon solvents such as carbon tetrachloride, chloroform, dichloromethane, dichloroethane, chlorobutane, bromobutane, chloropentane, bromopentane, chlorohexane, bromohexane, chlorocyclohexane, bromocyclohexane and the like, halogenated unsaturated hydrocarbon solvents such as chlorobenzene, dichlorobenzene, trichlorobenzene and the like, and ether solvents such as tetrahydrofuran, tetrahydropyran and the like. The polymer compound of the present invention can be usually dissolved in an amount of 0.1% by weight in the above-described solvent.

In the case of film formation using a solution, coating methods can be used such as a slit coat method, a knife coat method, a spin coat method, a casting method, a micro gravure coat method, a gravure coat method, a bar coat method, a roll coat method, a wire bar coat method, a dip coat method, a spray coat method, a screen printing method, a gravure printing method, a flexo printing method, an offset printing method, an inkjet coat method, a dispenser printing method, a nozzle coat method, a capillary coat method and the like, and preferable are a slit coat method, a capillary coat method, a gravure coat method, a micro gravure coat method, a bar coat method, a knife coat method, a nozzle coat method, an inkjet coat method and a spin coat method.

From the standpoint of film formability, the surface tension of a solvent at 25° C. is preferably larger than 15 mN/m, more preferably larger than 15 mN/m and smaller than 100 mN/m, further preferably larger than 25 mN/m and smaller than 60 mN/m.

The polymer compound of the present invention can be used also in an organic film transistor. The organic film transistor includes those having a source electrode and a drain electrode, an organic semiconductor layer (active layer) acting as a current pathway between these electrodes, and a gate electrode controlling the amount of current passing through this current pathway, wherein the organic semiconductor layer is constituted of the above-described organic film. Such an organic film transistor includes electric field effect types, electrostatic induction types and the like.

It is preferable that the electric field effect type organic film transistor has a source electrode and a drain electrode, an organic semiconductor layer (active layer) acting as a current pathway between them, a gate electrode controlling the amount of current passing through this current pathway, and an insulation layer disposed between the organic semiconductor layer and the gate electrode. Particularly, it is preferable that the source electrode and the drain electrode are disposed in contact with the organic semiconductor layer (active layer), and further, the gate electrode is disposed sandwiching the insulation layer in contact with the organic semiconductor layer. In the electric field effect type organic film transistor, the organic semiconductor layer is constituted of an organic film containing the polymer compound of the present invention.

It is preferable that the electrostatic induction type organic film transistor has a source electrode and a drain electrode, an organic semiconductor layer (active layer) acting as a current pathway between them, and a gate electrode controlling the amount of current passing through this current pathway, and this gate electrode is provided in an organic semiconductor layer. Particularly, it is preferable that the source electrode, the drain electrode and the gate electrode provided in the organic semiconductor layer are disposed in contact with the organic semiconductor layer. Here, the structure of the gate electrode may be a structure in which a current pathway flowing from the source electrode to the drain electrode is formed and the amount of current flowing in the current pathway can be controlled by voltage applied to the gate electrode, and for example, a comb-shaped electrode is mentioned. Also in the electrostatic induction type organic film transistor, the organic semiconductor layer is constituted of an organic film containing the polymer compound of the present invention.

The polymer compound of the present invention can also be used in an organic electroluminescent device (organic EL device). The organic EL device has a light emitting layer between a pair of electrodes at least one of which is transparent or semi-transparent. The organic EL device may also contain a hole transporting layer and an electron transporting layer, in addition to the light emitting layer. The polymer compound of the present invention is contained in any of the light emitting layer, the hole transporting layer and the electron transporting layer. The light emitting layer may also contain a charge transporting material (meaning a genetic name of an electron transporting material and a hole transporting material), in addition to the polymer compound of the present invention. The organic EL device includes a device having an anode, a light emitting layer and a cathode; a device having an anode, a light emitting layer, an electron transporting layer and a cathode, further having an electron transporting layer containing an electron transporting material between the cathode and the light emitting layer in adjacent to the light emitting layer; a device having an anode, a hole transporting layer, a light emitting layer and a cathode, further having a hole transporting layer containing a hole transporting material between the anode and the light emitting layer in adjacent to the light emitting layer; a device having an anode, a hole transporting layer, a light emitting layer, an electron transporting layer and a cathode; and the like.

The photoelectric conversion device using the polymer compound of the present invention is irradiated with a light such as sunlight or the like through a transparent or semi-transparent electrode, thereby generating photovoltaic power between electrodes, thus, it can be operated as an organic film solar battery. A plurality of organic film solar batteries can also be integrated and used as an organic film solar battery module.

By irradiating with a light through a transparent or semi-transparent electrode under condition of application of voltage between electrodes or under condition of no application, photocurrent flows, thus, it can be operated as an organic optical sensor. A plurality of organic optical sensors can also be integrated and used as an organic image sensor.

The above-described organic film transistor can be used, for example, as a picture element driving device used for regulating picture element control, screen luminance uniformity and screen rewriting speed of an electrophoresis display, a liquid crystal display, an organic electroluminescent display and the like.

The organic film solar battery can have a module structure which is basically the same as that of a conventional solar battery module. A solar battery module has generally a structure in which a cell is constituted on a supporting substrate such as a metal, ceramic and the like, the upper side thereof is covered with a filling resin, protective glass and the like and a light is introduced from the opposite side of the supporting substrate, however, it is also possible to provide a structure in which a transparent material such as reinforced glass and the like is used for the supporting substrate, a cell is constituted thereon and a light is introduced from the supporting substrate side. Specifically, module structures called super straight type, sub straight type or potting type, substrate-integrated module structures used in amorphous silicon solar batteries, and the like, are known. For the organic film solar battery produced by using the polymer compound of the present invention, these module structures can be appropriately selected depending on the use object, the use place and environments.

A typical module of super straight type or sub straight type has a structure in which cells are disposed at regular interval between supporting substrates of which one side or both sides are transparent and on which a reflection preventing treatment has been performed, adjacent cells are mutually connected by a metal lead or flexible wiring and the like, a power collecting electrode is placed on an outer edge part and generated powder is harvested outside. Between the substrate and the cell, various kinds of plastic materials such as ethylene vinyl acetate (EVA) and the like may be used in the form of a film or filling resin depending on the object, for protection of the cell and for improvement in power collecting efficiency. In the case of use at places requiring no covering of the surface with a hard material such as a place receiving little impact from outside, it is possible that the surface protective layer is constituted of a transparent plastic film, or the above-described filling resin is hardened to impart a protective function, and one supporting substrate is omitted. The circumference of the supporting substrate is fixed in the form of sandwich by a metal frame for tight seal of the inside and for securement of rigidity of the module, and a space between the supporting substrate and the frame is sealed tightly with a sealant. If a flexible material is used as the cell itself, or as the supporting substrate, the filling material and the sealant, a solar battery can be constituted also on a curved surface. In the case of a solar battery using a flexible support such as a polymer film and the like, a battery body can be fabricated by forming cells sequentially while feeding a support in the form of a roll, cutting into a desired size, then, sealing a peripheral part with a flexible moisture-proof material. Also, a module structure called "SCAF" described in Solar Energy Materials and Solar Cells, 48, p 383-391 can be adopted. Further, a solar battery using a flexible support can also be adhered and fixed to curved glass and the like and used.

EXAMPLES

Examples will be shown below for illustrating the present invention further in detail, but the present invention is not limited to them.

(Measurement of NMR)

A compound was dissolved in deuterated chloroform, and NMR thereof was measured using an NMR apparatus (manufactured by Varian, INOVA300).

(Measurement of Number-Average Molecular Weight and Weight-Average Molecular Weight)

As the number-average molecular weight and the weight-average molecular weight, the polystyrene-equivalent number-average molecular weight and the polystyrene-equivalent weight-average molecular weight were measured by gel permeation chromatography (GPC) (manufactured by Shimadzu Corp., trade name: LC-10Avp). The polymer compound to be subjected to measurement was dissolved at a concentration of about 0.5% by weight in tetrahydrofuran, and 30 μL of the solution was injected into GPC. Tetrahydrofuran was used as the mobile phase of GPC, and allowed to flow at a flow rate of 0.6 mL/min. Two columns of TSKgel SuperHM-H (manufactured by Tosoh Corporation) and one column of TSKgel SuperH2000 (manufactured by Tosoh Corporation) were connected serially. As the detector, a differential refractive index detector (manufactured by Shimadzu Corp., trade name: RID-10A) was used.

Synthesis Example 1

Synthesis of Compound 2

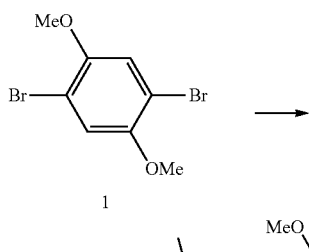

Into a four-necked flask were added 11.84 g (40.00 mmol) of a compound 1, 25.39 g (100.0 mmol) of bis(pinacolato)diboron, 9.814 g (100.0 mmol) of potassium acetate and 200 mL dioxane, and an argon gas was introduced into the resultant reaction solution at room temperature (25° C.) for 30 minutes, to bubble the solution. To the reaction solution were added 1.633 g (2.000 mmol) of diphenylphosphinoferrocene-palladium dichloride and 1.109 g (2.000 mmol) of diphenylphosphinoferrocene, then, the solution was heated under reflux for 20 hours. After heating under reflux, disappearance of raw materials was confirmed by liquid chromatography. The reaction solution was filtrated through Celite to separate insoluble components, then, the filtrate was dried to remove the solvent, thereby obtaining a brown solid. The resultant brown solid was dissolved in 200 mL of hot methanol and allowed to cause recrystallization, to obtain 6.11 g of a compound 2.

$^1$H-NMR (CDCl$_3$, δ(ppm)): 1.354 (s, 24H), 3.821 (s, 6H), 7.153 (s, 2H)

Synthesis Example 2

Synthesis of Compound 4

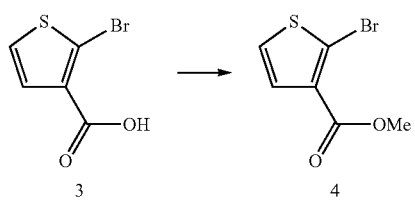 [SMILES: O=C(O)c1ccsc1Br ; COC(=O)c1ccsc1Br]

Into a four-necked flask were added 5.00 g (24.1 mmol) of a compound 3, 100 mL of methanol and 1 mL of concentrated sulfuric acid, and these were reacted under reflux condition for 10 hours. After the reaction, disappearance of raw materials was confirmed by liquid chromatography. Next, to the reaction solution were added water and chloroform, and the organic layer was extracted. After distilling off chloroform, the resultant coarse product was purified by silica gel column chromatography using hexane as a developing solvent, to obtain 5.08 g of a compound 4.

$^1$H-NMR (CDCl$_3$, δ(ppm)): 3.883 (s, 3H), 7.224 (d, 1H), 7.362 (d, 1H)

Synthesis Example 3

Synthesis of Compound 5

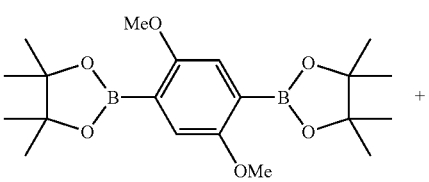

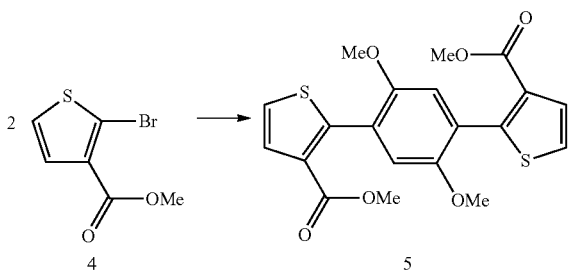

Into a four-necked flask were added 2.11 g (10.00 mmol) of the compound 4 and 100 mL of tetrahydrofuran, and an argon gas was introduced into the resultant reaction solution at room temperature (25° C.) for 30 minutes, to bubble the solution. Thereafter, to the reaction solution were added 45.8 mg (0.05 mmol) of tris(dibenzylideneacetone)palladium, 58.0 mg (0.20 mmol) of [tri(tertiary butyl)phosphonium]tetrafluoroborate and 15.0 g (30.0 mmol) of a 2 mol/L potassium phosphate aqueous solution. While stirring the reaction solution at 80° C., a solution prepared by dissolving 1.95 g of the compound 2 (5.00 mmol) in 20 mL of tetrahydrofuran was dropped over a period of 5 minutes. Two hours after, disappearance of raw materials was confirmed by liquid chromatography. Next, to the reaction solution were added water and chloroform, and the organic layer was extracted. After distilling off chloroform, the resultant coarse product was purified by column chromatography using chloroform as a developing solvent, to obtain 1.76 g of a compound 5.

$^1$H-NMR (CDCl$_3$, δ(ppm)): 3.738 (s, 12H), 6.932 (s, 2H), 7.301 (d, 2H), 7.501 (d, 2H)

Synthesis Example 4

Synthesis of Compound 6

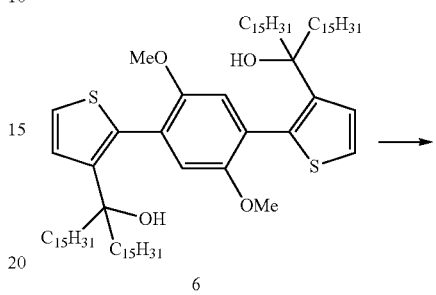

5

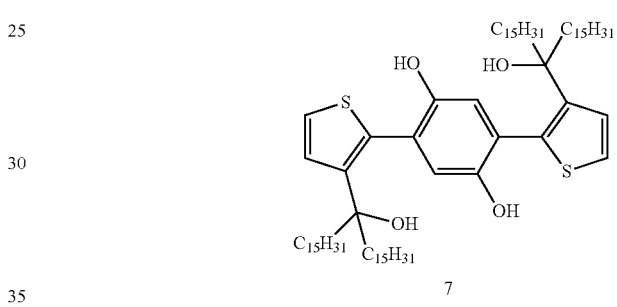

6

Into a four-necked flask were added 628 mg (1.50 mmol) of the compound 5 and 40 mL of tetrahydrofuran, and an argon gas was introduced into the resultant reaction solution at room temperature (25° C.) for 30 minutes, to bubble the solution. The reaction solution was cooled down to 0° C., and 24 mL of a tetrahydrofuran solution containing 0.5 mol/L pentadecylmagnesium bromide was added, and the mixture was stirred for 30 minutes. The reaction solution was heated up to 40° C., and stirred for 6 hours. Next, to the reaction solution were added water and chloroform, and the organic layer was extracted. After distilling off chloroform, the resultant coarse product was purified by column chromatography using chloroform as a developing solvent, to obtain a brown powder. The brown powder was washed with a mixed solution of methanol and ethanol prepared by mixing them so that the volume ratio of ethanol with respect to the volume of methanol was 1, to obtain 884 mg of a compound 6.

Synthesis Example 5

Synthesis of Compound 7

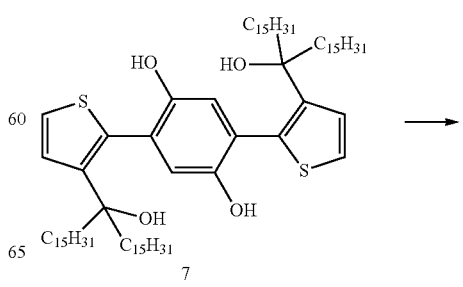

6

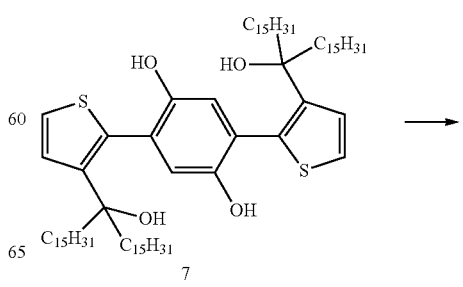

7

Into a four-necked flask were added 880 mg (0.731 mmol) of the compound 6 and 20 mL of methylene chloride, and an argon gas was introduced into the resultant reaction solution at room temperature (25° C.) for 30 minutes, to bubble the solution. To the reaction solution was added 2.92 mL of a methylene chloride solution containing 1 mol/L boron tribromide, and the mixture was stirred at room temperature for 3 hours. Next, to the reaction solution were added water and chloroform, and the organic layer was extracted. Next, chloroform was distilled off, to obtain 800 mg of a brown oil containing a compound 7.

Example 1

Synthesis of Compound 8

7

-continued

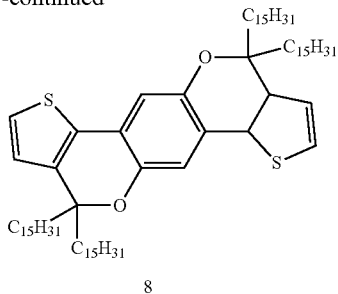

8

Into an egg-shaped flask were added 800 mg of the brown oil containing the compound 7 synthesized in Synthesis Example 5, 20 mL of toluene and 2 mg of p-toluenesulfonic acid, and the mixture was stirred at 60° C. for 5 hours. Next, to the reaction solution were added water and chloroform, and the organic layer was extracted. After distilling off chloroform, the resultant coarse product was purified by column chromatography using hexane as a developing solvent, to obtain 92.3 mg of a compound 8.

$^1$H-NMR (CDCl$_3$, δ(ppm)): 0.874 (t, 12H), 1.244 (m, 104H), 1.843 (m, 8H), 6.734 (d, 2H), 6.818 (s, 2H), 7.150 (d, 2H)

Example 2

Synthesis of Compound 9

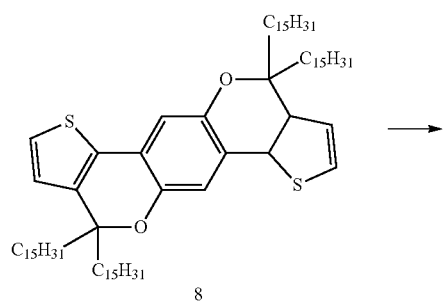

Into a four-necked flask were added 92.3 mg (0.081 mmol) of the compound 8 and 30 mL of tetrahydrofuran, and an argon gas was introduced into the resultant reaction solution at room temperature (25° C.) for 30 minutes, to bubble the solution. The reaction solution was cooled down to 0° C., then, 31.7 mg (0.178 mmol) of NBS was added, and the mixture was heated up to room temperature (25° C.). Five hours after, disappearance of raw materials was confirmed by liquid chromatography. Thereafter, to the reaction solution was added a sodium thiosulfate aqueous solution, further, hexane was added and the organic layer was extracted. Thereafter, the solvent was removed from a component fractionated by a column using hexane as a developing solvent and drying thereof was conducted, to obtain 94.1 mg of a compound 9.

$^1$H-NMR (CDCl$_3$, δ(ppm)): 0.876 (t, 12H), 1.223 (m, 52H), 1.248 (m, 52H), 1.789 (m, 8H), 6.647 (s, 1H), 6.695 (s, 1H)

Synthesis Example 6

Synthesis of Compound 11

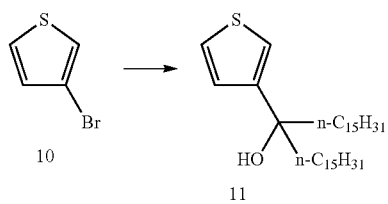

Into a four-necked flask were added 16.31 g (100.0 mmol) of a compound 10 and 326 mL of diethyl ether, and an argon gas was introduced into the resultant reaction solution at room temperature (25° C.) for 30 minutes, to bubble the solution. The reaction solution was cooled down to 78° C., then, 40.4 mL of a tetrahydrofuran solution containing 2.6 mol/L butyllithium (n-BuLi) was added, and the mixture was stirred for 1 hour. Subsequently, 47.3 g (105.0 mmol) of dipentadecyl ketone was added, and the mixture was heated up to room temperature, then, stirred for 2 hours. Next, to the reaction solution was added an acetic acid aqueous solution, further, hexane was added and the organic layer was extracted. Hot ethanol was added to a brown solid obtained after distilling off hexane and the intended material was extracted, thereby obtaining 49.2 g of a compound 11.

$^1$H-NMR (CDCl$_3$, δ(ppm)): 0.879 (t, 6H), 1.253 (m, 52H), 1.746 (m, 4H), 6.960 (d, 1H), 7.266 (d, 1H)

Synthesis Example 7

Synthesis of Compound 12

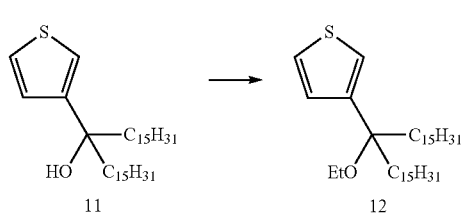

Into an egg-shaped flask were added 17.8 g (33.3 mmol) of the compound 11, 150 mL of ethanol and 2 mL of concentrated sulfuric acid, the mixture was stirred at 50° C. for 2 hours, and disappearance of raw materials was confirmed by liquid chromatography. Next, to the reaction solution were added water and chloroform, and the organic layer was extracted. After distilling off chloroform, the resultant coarse product was purified by column chromatography using hexane as a developing solvent, to obtain 13.8 g of a compound 12.

$^1$H-NMR (CDCl$_3$, δ(ppm)): 0.884 (t, 6H), 1.130 (t, 3H), 1.235 (m, 52H), 1.774 (m, 4H), 3.150 (q, 2H), 7.051 (m, 2H), 7.242 (d, 1H)

Synthesis Example 8

Synthesis of Compound 13

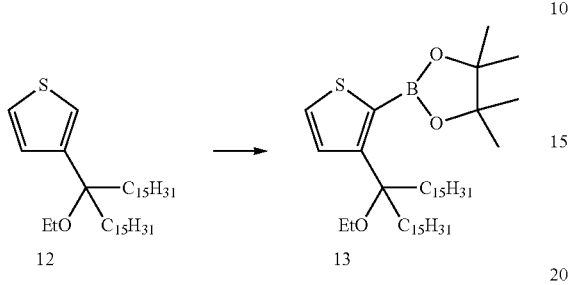

Into a four-necked flask were added 5.63 g (10.0 mmol) of the compound 12 and 100 mL of diethyl ether, argon was introduced into the resultant reaction solution at room temperature (25° C.) for 30 minutes, to bubble the solution. The reaction solution was cooled down to −50° C., then, 4.0 mL of a tetrahydrofuran solution containing 2.6 mol/L butyllithium (n-BuLi) was added, and the mixture was stirred for 1 hour. Subsequently, 1.95 g (10.50 mmol) of 2-isopropoxy-4,4,5,5-tetramethyl-1,3,2-dioxaborolane was added, and the mixture was heated up to room temperature, then, stirred for 2 hours. Next, to the reaction solution was added water, further, hexane was added and the organic layer was extracted. A brown oil obtained after distilling off hexane was washed using hot methanol, to obtain 6.48 g of a compound 13.

$^1$H-NMR (CDCl$_3$, δ(ppm)): 0.879 (t, 6H), 1.204 (t, 3H), 1.252 (m, 52H), 1.335 (s, 12H), 1.989 (m, 4H), 3.224 (q, 2H), 7.264 (d, 1H), 7.422 (d, 1H)

Synthesis Example 9

Synthesis of Compound 15

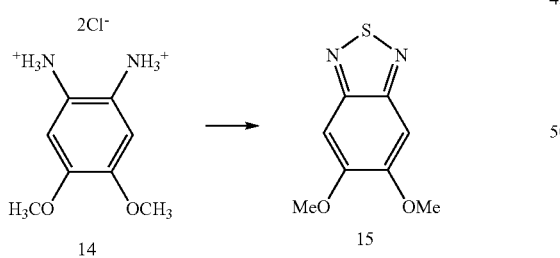

Into a four-necked flask were added 5.00 g (20.74 mmol) of a compound 14, 150 mL of triethylamine and 500 mL of methylene chloride, and an argon gas was introduced into the resultant reaction solution at 40° C. for 30 minutes, to bubble the solution. To the reaction solution was added 5.00 g (42.03 mmol) of thionyl chloride, then, the solution was heated under reflux for 1 hour. After heating under reflux, disappearance of raw materials was confirmed by liquid chromatography. Next, the solvent in the reaction solution was distilled off to obtain a solid to which water was added, and the mixture was stirred for 30 minutes and washed, and water was distilled off to obtain a coarse crystal. The coarse crystal was recrystallized using methanol, to obtain 3.30 g of a compound 15.

$^1$H-NMR (CDCl$_3$, δ(ppm)): 4.024 (s, 6H), 7.202 (s, 2H)

Synthesis Example 10

Synthesis of Compound 16

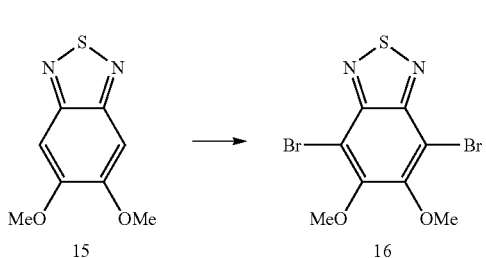 [SMILES: COc1cc2nsnc2cc1OC ; COc1c(OC)c(Br)c2nsnc2c1Br]

Into a four-necked flask were added 3.30 g (16.82 mmol) of the compound 15, 20 mL of acetic acid and 100 mL of chloroform, and an argon gas was introduced into the resultant reaction solution at room temperature (25° C.) for 30 minutes, to bubble the solution. Subsequently, to the reaction solution was added 3.5 mL (67.97 mmol) of bromine, and the solution was reacted at room temperature for 24 hours. After the reaction, disappearance of raw materials was confirmed by liquid chromatography. Thereafter, to the reaction solution was added a sodium thiosulfate aqueous solution, and an extraction operation using chloroform was conducted, to obtain a coarse crystal. Column chromatography was performed using a mixed solution prepared by mixing hexane and chloroform so that the volume ratio of chloroform with respect to the volume of hexane was 1 as a developing solvent, to obtain a coarse crystal. Thereafter, recrystallization using methanol was performed, to obtain 4.44 g of a compound 16.

$^1$H-NMR (CDCl$_3$, δ(ppm)): 4.051 (s, 6H)

Synthesis Example 11

Synthesis of Compound 17

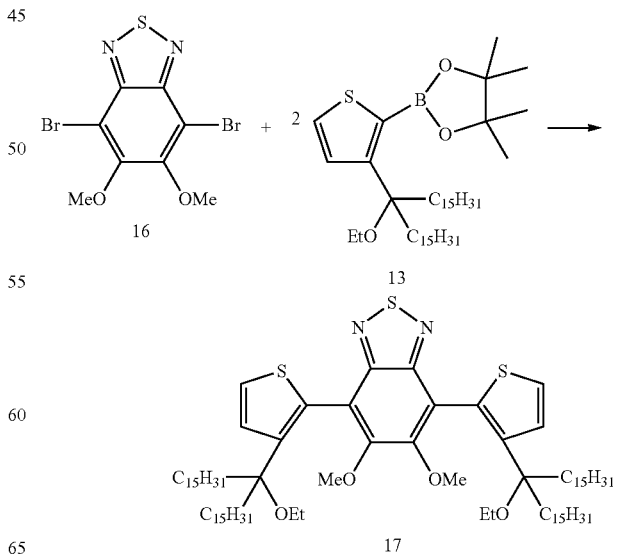

Into a four-necked flask were added 354 mg (1.00 mmol) of the compound 16 and 10 mL of tetrahydrofuran, and an argon gas was introduced into the resultant reaction solution at room temperature (25° C.) for 30 minutes, to bubble the solution. Thereafter, to the reaction solution were added 36.6 mg (0.04 mmol) of tris(dibenzylideneacetone)palladium, 46.4 mg (0.16 mmol) of [tri(tertiary butyl)phosphonium]tetrafluoroborate and 2.5 g of a 2 mol/L potassium phosphate aqueous solution. While stirring the reaction solution at 80° C., a solution prepared by dissolving 1.38 g of the compound 13 (2.00 mmol) in 5 mL of tetrahydrofuran was added, and the mixture was stirred. Two hours after, disappearance of raw materials was confirmed by liquid chromatography. Next, to the reaction solution were added water and hexane, and the organic layer was extracted. Hexane was distilled off, then, the resultant coarse product was purified by column chromatography using a mixed solvent prepared by mixing hexane and chloroform so that the volume ratio of hexane with respect to the volume of chloroform was 4 as a developing solvent, to obtain 687 mg of a compound 17.

$^1$H-NMR (CDCl$_3$, δ(ppm)): 0.731 (t, 6H), 0.884 (t, 12H), 1.250 (m, 96H), 1.750 (m, 8H), 3.120 (m, 8H), 3.843 (s, 6H), 7.154 (d, 2H), 7.386 (d, 2H)

Synthesis Example 12

Synthesis of compound 18

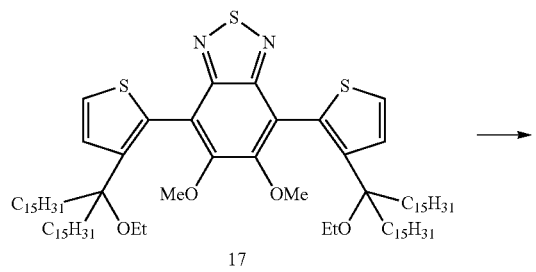

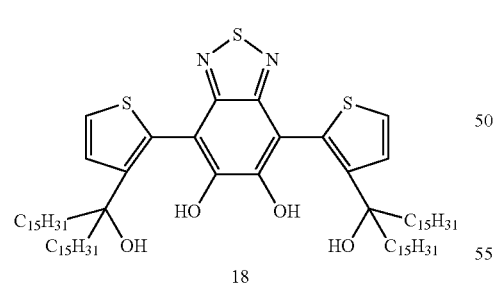

Into a four-necked flask were added 279 mg (0.211 mmol) of the compound 17 and 40 mL of methylene chloride, and an argon gas was introduced into the resultant reaction solution at room temperature (25° C.) for 30 minutes, to bubble the solution. Into the reaction solution was added 1.27 mL (1.27 mmol) of a methylene chloride solution containing 1 mol/L boron tribromide, and the mixture was stirred at room temperature for 2 hours. Thereafter, to the reaction solution were added an acetic acid aqueous solution and chloroform, and the organic layer was extracted. Chloroform in the organic layer was distilled off, to obtain 300 mg of a brown oil containing a compound 18.

Example 3

Synthesis of Compound 19

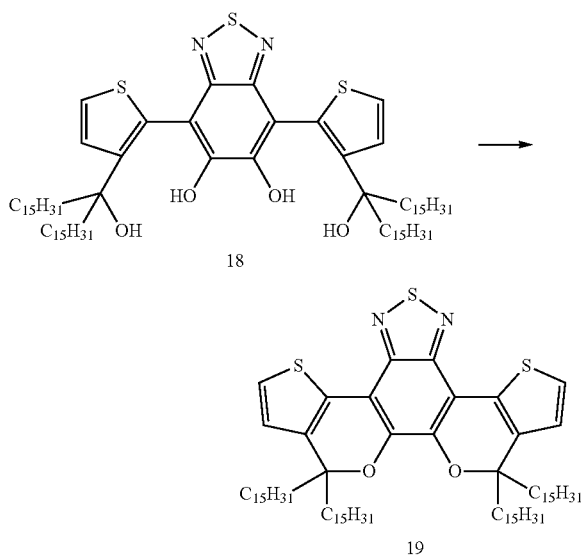

Into an egg-shaped flask were added 300 mg of the brown oil containing the compound 18 synthesized on Synthesis Example 12, 10 mL of toluene and 1 mg of p-toluenesulfonic acid, and these were stirred at 60° C. for 10 hours. Next, to the reaction solution were added water and chloroform, and the organic layer was extracted. After distilling off chloroform, the resultant coarse product was purified by column chromatography using hexane as a developing solvent, to obtain 52.1 mg of a compound 19.

$^1$H-NMR (CDCl$_3$, δ(ppm)): 0.872 (t, 12H), 1.208 (m, 48H), 1.241 (m, 48H), 1.414 (m, 8H), 1.973 (m, 8H), 6.826 (d, 2H), 7.375 (d, 2H)

Example 4

Synthesis of Compound 20

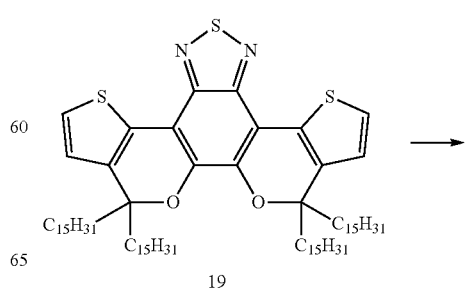

-continued

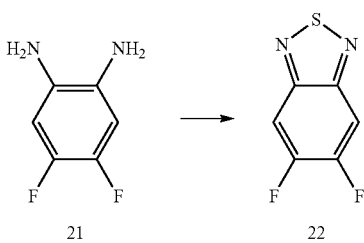 [SMILES: Nc1cc(F)c(F)cc1N ; Fc1cc2nsnc2cc1F]

20

Into a four-necked flask were added 52.1 mg (0.043 mmol) of the compound 19 and 20 mL of tetrahydrofuran, and an argon gas was introduced into the resultant reaction solution at room temperature (25° C.) for 30 minutes, to bubble the solution. The reaction solution was cooled down to 0° C., then, 16.8 mg (0.095 mmol) of NBS was added, and the mixture was heated up to room temperature (25° C.). Three hours after, disappearance of raw materials was confirmed by liquid chromatography. Thereafter, to the reaction solution was added a sodium thiosulfate aqueous solution, further, hexane was added and the organic layer was extracted. Thereafter, the organic layer was separated by a column using hexane as a developing solvent, and the component obtained by separation was dried to remove the solvent, thereby obtaining 57.8 mg of a compound 20.

$^1$H-NMR (CDCl$_3$, δ(ppm)): 0.872 (t, 12H), 1.213 (m, 48H), 1.241 (m, 48H), 1.417 (m, 8H), 1.955 (m, 8H), 6.775 (s, 2H)

Synthesis Example 13

Synthesis of Compound 22

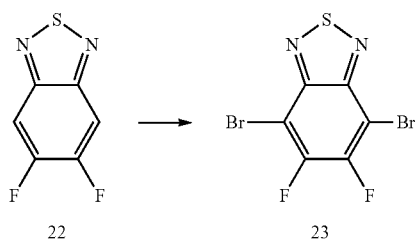 [SMILES: Fc1cc2nsnc2cc1F ; Fc1c(F)c(Br)c2nsnc2c1Br]

Into a 500 ml flask were charged 10.2 g (70.8 mmol) of 4,5-difluoro-1,2-diaminobenzene (compound 21) (manufactured by Tokyo Chemical Industry Co., Ltd.) and 150 mL of pyridine, to obtain a uniform solution. The flask was cooled down to 0° C., and 16.0 g (134 mmol) of thionyl chloride was dropped into the flask. After dropping, the flask was warmed at 25° C., and the reaction was conducted for 6 hours. Thereafter, to the reaction solution was added 250 ml of water, further, chloroform was added and the organic layer containing the reaction product was extracted. The organic layer as a chloroform solution was dried over sodium sulfate, condensed by an evaporator, and the deposited solid was purified by recrystallization. Methanol was used as the solvent for recrystallization. After purification, 10.5 g (61.0 mmol) of a compound 22 was obtained.

$^1$H-NMR (CDCl$_3$, δ(ppm)): 7.75 (s, 2H)
$^{19}$F-NMR (CDCl$_3$, δ(ppm)): −128.3 (s, 2F)

Synthesis Example 14

Synthesis of Compound 23

Into a 100 mL flask were charged 2.00 g (11.6 mmol) of the compound 22 and 0.20 g (3.58 mmol) of an iron powder, and the flask was heated at 90° C. Into this flask, 31 g (194 mmol) of bromine was dropped over a period of 1 hour. After dropping, the reaction solution was stirred at 90° C. for 38 hours. Thereafter, the flask was cooled down to room temperature (25° C.), and 100 mL of chloroform was added for dilution. The resultant solution was poured into 300 mL of a 5 wt % sodium sulfite aqueous solution, and the mixture was stirred for 1 hour. The organic layer of the resultant mixed solution was fractionated, and the aqueous layer was extracted with chloroform three times. The resultant extraction solution was mixed with the organic layer, and the mixed solution was dried over sodium sulfate, and the solvent was distilled off by an evaporator to perform condensation. The resultant yellow solid was dissolved in 90 mL of methanol heated at 55° C., thereafter, the solution was cooled down to 25° C. The deposited crystal was isolated by filtration, thereafter, dried at room temperature (25° C.) under reduced pressure, to obtain 1.50 g of a compound 23.

$^{19}$F-NMR (CDCl$_3$, δ(ppm)): −118.9 (s, 2F)

Synthesis Example 15

Synthesis of Compound 24

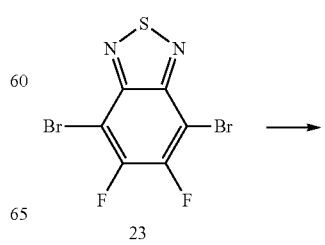

-continued

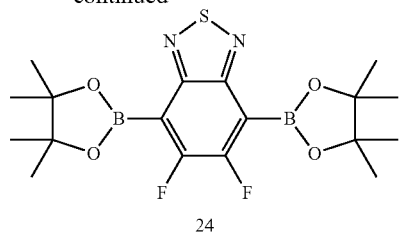

24

Into a four-necked flask were added 12.30 g (37.28 mmol) of the compound 23, 23.67 g (93.20 mmol) of bis(pinacolato)diboron, 9.15 g (93.20 mmol) of potassium acetate and 500 mL of dioxane, and an argon gas was introduced into the resultant reaction solution at room temperature (25° C.) for 30 minutes, to bubble the solution. To the reaction solution were added 1.52 g (1.86 mmol) of diphenylphosphinoferrocene-palladium dichloride and 1.03 mg (1.86 mmol) of diphenylphosphinoferrocene, then, the solution was heated under reflux for 60 hours. After reflux, disappearance of raw materials was confirmed by liquid chromatography. The reaction solution was filtrated through Celite to separate insoluble components, then, the filtrate was dried to remove the solvent, thereby obtaining a brown solid. To the resultant brown solid was added 200 mL of hot hexane and the mixture was filtrated, and the filtrate was dried to remove the solvent, thereby obtaining a coarse crystal. Subsequently, the coarse crystal was recrystallized by hexane. Recrystallization was conducted twice, to obtain 3.12 g of a compound 24.

$^1$H-NMR (CDCl$_3$, δ(ppm)): 1.45 (s, 24H)
$^{19}$F-NMR (CDCl$_3$, δ(ppm)): −117 (s, 2F)

Example 5

Synthesis of Polymer A

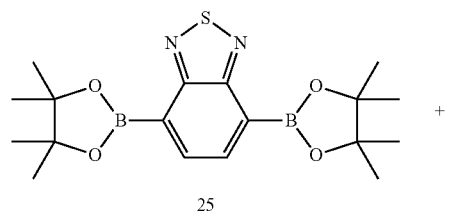

25

+

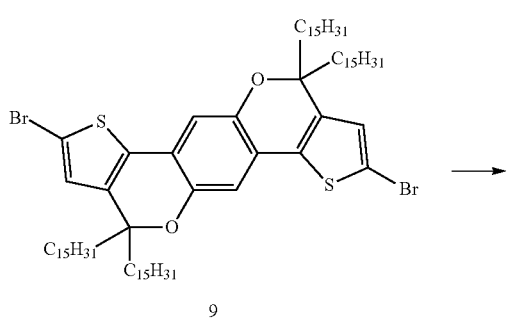

9

-continued

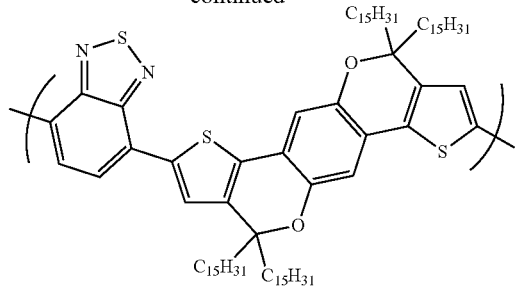

Polymer A

Into a four-necked flask were added 45.4 mg (0.035 mmol) of the compound 9 and 5 mL of tetrahydrofuran, and an argon gas was introduced into the resultant reaction solution at room temperature (25° C.) for 30 minutes, to bubble the solution. Thereafter, to the reaction solution were added 0.64 mg (0.0007 mmol) of tris(dibenzylideneacetone)palladium, 0.81 mg (0.0028 mmol) of [tri(tertiary butyl)phosphonium]tetrafluoroborate and 0.2 g (0.4 mmol) of a 2 mol/L potassium phosphate aqueous solution. While stirring the reaction solution at a temperature of an oil bath of 80° C., a solution prepared by dissolving 13.6 mg of a compound 25 (0.035 mmol) in 2 mL of tetrahydrofuran was dropped over a period of 10 minutes, and the mixture was stirred for 30 minutes. Thereafter, to the reaction solution was added 3.5 mg (0.029 mmol) of phenylboric acid, further, the mixture was stirred for 1 hour, then, the reaction was stopped. The reaction was conducted under an argon atmosphere.

Thereafter, to the reaction solution were added 1.0 g of sodium diethyldithiocarbamate and 9.0 mL of pure water, and the mixture was stirred for 3 hours while refluxing. The aqueous layer in the reaction solution was removed, then, the organic layer was washed with 10 ml of water twice, with 10 mL of a 3 wt % acetic acid aqueous solution twice, further with 10 mL of water twice, and poured into methanol to cause deposition of a polymer. The polymer was filtrated, then, dried, and the resultant polymer was dissolved in toluene. The toluene solution was allowed to pass through an alumina/silica gel column, and the resultant solution was poured into methanol to cause deposition of a polymer. The polymer was filtrated, then, dried, to obtain 25 mg of a polymer A.

The polymer A had a polystyrene-equivalent weight-average molecular weight (Mw) of 96000 and a polystyrene-equivalent number-average molecular weight (Mn) of 32000, both measured by GPC. The polymer A had an absorption end wavelength of 780 nm.

Example 6

Synthesis of Polymer B

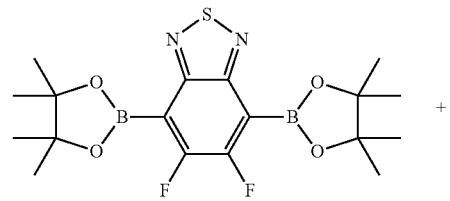

24

+

-continued

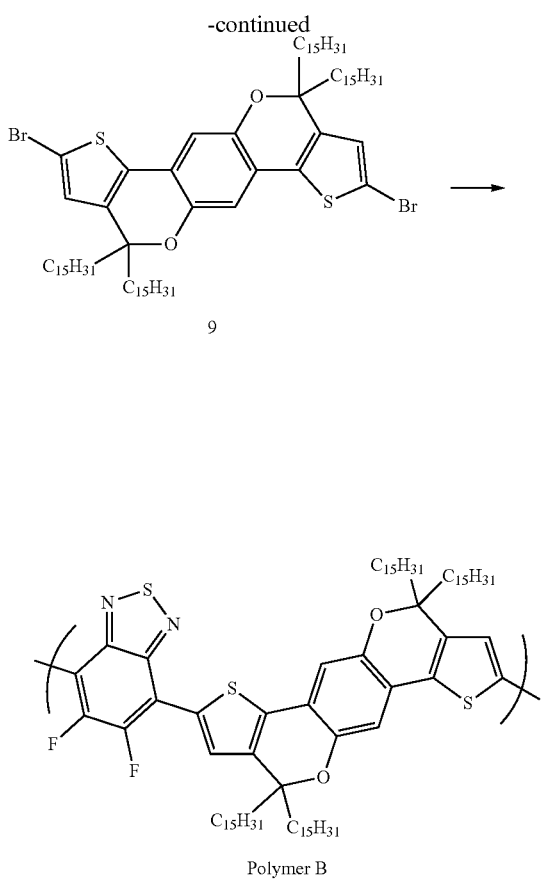

Polymer B

Into a four-necked flask were added 48.7 mg (0.038 mmol) of the compound 9 and 5.3 mL of methylene chloride, and an argon gas was introduced into the resultant reaction solution at room temperature (25° C.) for 30 minutes, to bubble the solution. Thereafter, to the reaction solution were added 1.37 mg (0.0015 mmol) of tris(dibenzylideneacetone)palladium, 1.74 mg (0.006 mmol) of [tri(tertiary butyl)phosphonium] tetrafluoroborate and 0.2 g (0.4 mmol) of a 2 mol/L potassium phosphate aqueous solution. While stirring the reaction solution at a temperature of an oil bath of 40° C., a solution prepared by dissolving 15.9 mg of the compound 24 (0.038 mmol) in 2.3 mL of methylene chloride was dropped over a period of 10 minutes, and the mixture was stirred for 30 minutes. Thereafter, to the reaction solution was added 3.8 mg (0.031 mmol) of phenylboric acid, further, the mixture was stirred for 1 hour, then, the reaction was stopped. The reaction was conducted under an argon atmosphere.

Thereafter, to the reaction solution were added 1.0 g of sodium diethyldithiocarbamate and 9.0 mL of pure water, and the mixture was stirred for 3 hours while refluxing. The aqueous layer in the reaction solution was removed, then, the organic layer was washed with 10 ml of water twice, with 10 mL of a 3 wt % acetic acid aqueous solution twice, further with 10 mL of water twice, and poured into methanol to cause deposition of a polymer. The polymer was filtrated, then, dried, and the resultant polymer was dissolved in toluene. The toluene solution was allowed to pass through an alumina/silica gel column, and the resultant solution was poured into methanol to cause deposition of a polymer. The polymer was filtrated, then, dried, to obtain 13 mg of a polymer B.

The polymer B had a polystyrene-equivalent weight-average molecular weight (Mw) of 35000 and a polystyrene-equivalent number-average molecular weight (Mn) of 16000, both measured by GPC. The polymer B had an absorption end wavelength of 770 nm.

Example 7

Synthesis of Polymer C

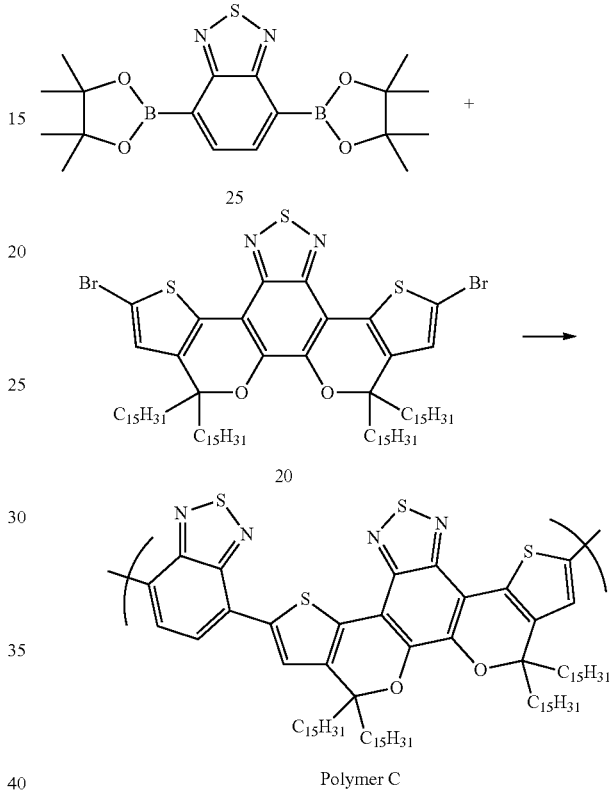

Polymer C

Into a four-necked flask were added 57.6 mg (0.043 mmol) of the compound 20 and 3 mL of tetrahydrofuran, and an argon gas was introduced into the resultant reaction solution at room temperature (25° C.) for 30 minutes, to bubble the solution. Thereafter, to the reaction solution were added 1.95 mg (0.0021 mmol) of tris(dibenzylideneacetone) palladium, 2.47 mg (0.0085 mmol) of [tri(tertiary butyl)phosphonium] tetrafluoroborate and 0.2 g (0.4 mmol) of a 2 mol/L potassium phosphate aqueous solution. While stirring the reaction solution at a temperature of an oil bath of 80° C., a solution prepared by dissolving 16.5 mg of a compound 25 (manufactured by Aldrich) (0.043 mmol) in 2 mL of tetrahydrofuran was dropped over a period of 10 minutes, and the mixture was stirred for 30 minutes. Thereafter, to the reaction solution was added 4.3 mg (0.029 mmol) of phenylboric acid, further, the mixture was stirred for 1 hour, then, the reaction was stopped. The reaction was conducted under an argon atmosphere.

Thereafter, to the reaction solution were added 1.0 g of sodium diethyldithiocarbamate and 9.0 mL of pure water, and the mixture was stirred for 3 hours while refluxing. The aqueous layer in the reaction solution was removed, then, the organic layer was washed with 10 ml of water twice, with 10 mL of a 3 wt % acetic acid aqueous solution twice, further with 10 mL of water twice, and poured into methanol to cause deposition of a polymer. The polymer was filtrated, then, dried, and the resultant polymer was dissolved in toluene. The toluene solution was allowed to pass through an alumina/silica gel column, and the resultant solution was poured into methanol to cause deposition of a polymer. The polymer was filtrated, then, dried, to obtain 37 mg of a polymer C.

The polymer C had a polystyrene-equivalent weight-average molecular weight (Mw) of 167000 and a polystyrene-equivalent number-average molecular weight (Mn) of 51000, both measured by GPC. The polymer C had an absorption end wavelength of 820 nm.

Example 8

Synthesis of Polymer D

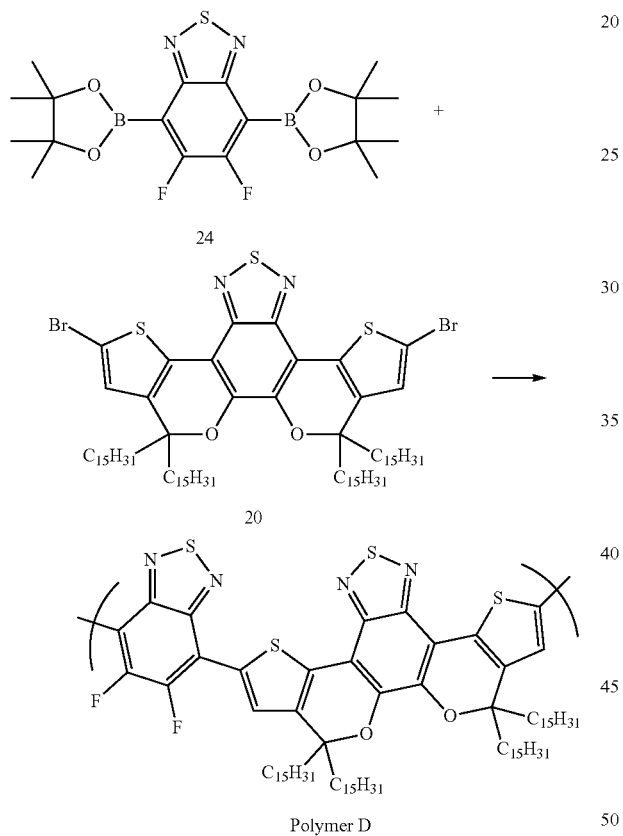

Into a four-necked flask were added 54.2 mg (0.040 mmol) of the compound 20 and 2.8 mL of methylene chloride, and an argon gas was introduced into the resultant reaction solution at room temperature (25° C.) for 30 minutes, to bubble the solution. Thereafter, to the reaction solution were added 1.83 mg (0.002 mmol) of tris(dibenzylideneacetone)palladium, 2.32 mg (0.008 mmol) of [tri(tertiary butyl)phosphonium] tetrafluoroborate and 0.2 g (0.4 mmol) of a 2 mol/L potassium phosphate aqueous solution. While stirring the reaction solution at a temperature of an oil bath of 40° C., a solution prepared by dissolving 17.0 mg of the compound 24 (0.040 mmol) in 1.2 mL of methylene chloride was dropped over a period of 10 minutes, and the mixture was stirred for 30 minutes. Thereafter, to the reaction solution was added 4.0 mg (0.033 mmol) of phenylboric acid, further, the mixture was stirred for 1 hour, then, the reaction was stopped. The reaction was conducted under an argon atmosphere.

Thereafter, to the reaction solution were added 1.0 g of sodium diethyldithiocarbamate and 9.0 mL of pure water, and the mixture was stirred for 3 hours while refluxing. The aqueous layer in the reaction solution was removed, then, the organic layer was washed with 10 ml of water twice, with 10 mL of a 3 wt % acetic acid aqueous solution twice, further with 10 mL of water twice, and poured into methanol to cause deposition of a polymer. The polymer was filtrated, then, dried, and the resultant polymer was dissolved in toluene. The toluene solution was allowed to pass through an alumina/silica gel column, and the resultant solution was poured into methanol to cause deposition of a polymer. The polymer was filtrated, then, dried, to obtain 20 mg of a polymer D.

The polymer D had a polystyrene-equivalent weight-average molecular weight (Mw) of 42000 and a polystyrene-equivalent number-average molecular weight (Mn) of 20000, both measured by GPC. The polymer D had an absorption end wavelength of 800 nm.

Synthesis Example 16

Synthesis of Compound 27

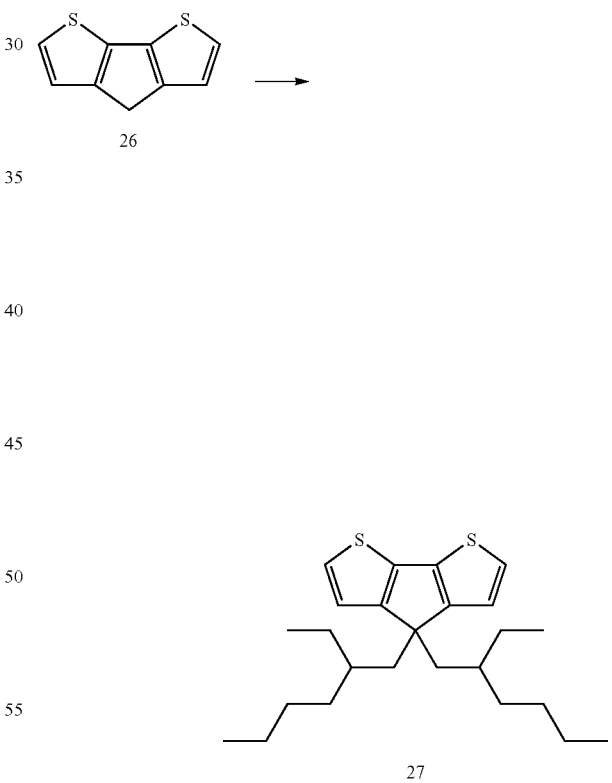

Into a 200 mL flask containing an argon-purged atmosphere were charged 1.78 g (10.0 mmol) of the compound 26, 5.83 g (25.0 mmol) of 2-ethylhexyl bromide, 41.5 mg (0.25 mmol) of potassium iodide and 1.68 g (30.0 mmol) of potassium hydroxide, and these were dissolved in 35 mL of dimethyl sulfoxide, and the mixture was stirred at room temperature (25° C.) for 24 hours. After the reaction, 100 mL of water was added, the product was extracted with hexane, and purified by a silica gel column using hexane as a developing solvent, to obtain 2.61 g of a compound 27.

Synthesis Example 17

Synthesis of Compound 28

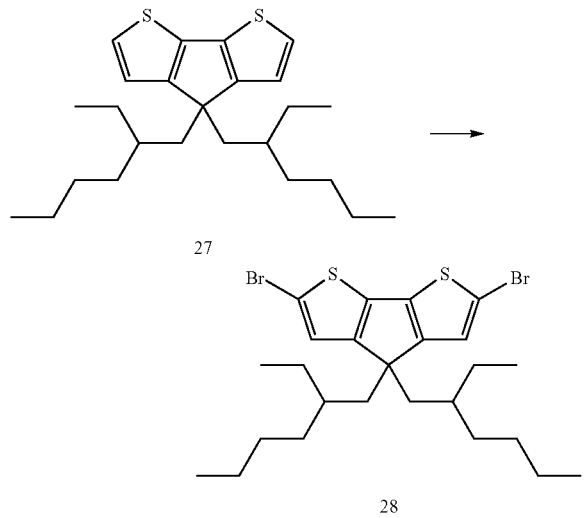

27

28

Into a 200 mL flask containing an argon-purged atmosphere were added 1.31 g (3.25 mmol) of the compound 27 and 25 mL of N,N-dimethylformamide (DMF). Thereafter, the flask was cooled down to 0° C., 1.21 g of N-bromosuccinimide (NBS) was added, and the mixture was stirred for 12 hours. Into the reaction solution was added 100 mL of water to stop the reaction, and the product was extracted with an ether. The product was purified by a silica gel column using hexane as a developing solvent, to obtain 1.70 g of a compound 28.

Synthesis Example 18

Synthesis of Polymer E

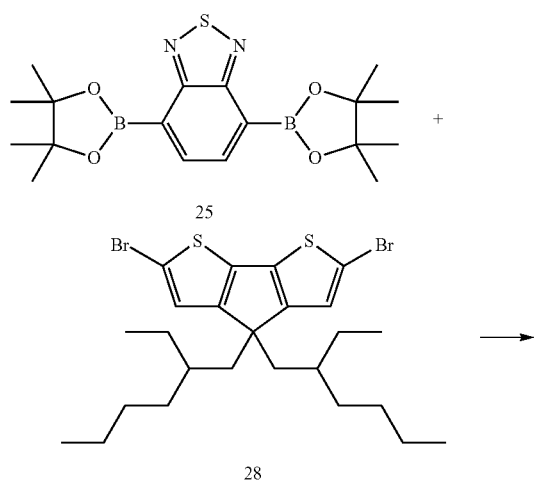

25

28

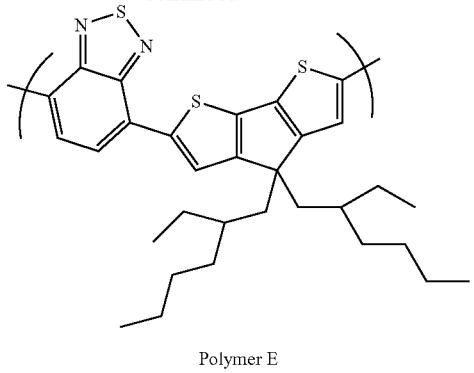

Polymer E

Into a 200 mL flask containing an argon-purged atmosphere were added 561 mg (1.00 mmol) of the compound 28, 388.1 mg (1.00 mmol) of the compound 25 (4,7-bis(4,4,5,5-tetramethyl-1,3,2-dioxaborolan-2-yl)-2,1,3-benzothiadiazole) (manufactured by Sigma Aldrich) and 202 mg of methyltrialkylammonium chloride (trade name: Aliquat336 (registered trademark), manufactured by Sigma Aldrich), and these were dissolved in 20 ml of toluene. An argon gas was introduced into the resultant toluene solution, to effect bubbling for 30 minutes. Thereafter, to the reaction solution were added 2.25 mg of palladium acetate, 12.3 mg of tris(2-methoxyphenyl)phosphine (Tris(2-methoxyphenyl)phosphine) and 6.5 mL of a 16.7 wt % sodium carbonate aqueous solution, and the mixture was stirred at 100° C. for 5 hours. Thereafter, to the reaction solution was added 50 mg of phenylboric acid, further, the mixture was reacted at 70° C. for 2 hours. Thereafter, to the reaction solution were added 2 g of sodium diethyldithiocarbamate and 20 mL of water, and the mixture was stirred for 2 hours under reflux. The aqueous layer in the reaction solution was removed, then, the organic layer was washed with 20 ml of water twice, with 20 mL of a 3 wt % acetic acid aqueous solution twice, further with 20 mL of water twice, and poured into methanol to cause deposition of a polymer. The polymer was filtrated, then, dried, and the resultant polymer was dissolved in 30 mL of o-dichlorobenzene. The o-dichlorobenzene solution was allowed to pass through an alumina/silica gel column, and the resultant solution was poured into methanol to cause deposition of a polymer. The polymer was filtrated, then, dried, to obtain 280 mg of a polymer E. The polymer E had a polystyrene-equivalent molecular weight (Mw) of 30000 and a polystyrene-equivalent molecular weight (Mn) of 14000, both measured by GPC.

Example 9

Fabrication of Organic Transistor

An n-type silicon substrate doped at high concentration having a thermally oxidized film having a thickness of 300 nm was ultrasonically washed in acetone for 10 minutes, then, irradiated with ozone and UV for 20 minutes. Thereafter, β-phenethyltrichlorosilane was collected by a syringe and dropped into toluene at a proportion of 5 drops of β-phenethyltrichlorosilane per 10 ml of toluene, to prepare a diluted toluene solution of β-phenethyltrichlorosilane. The toluene solution was spin-coated on the thermally oxidized film, thereby attaining silane treatment of the surface of the thermally oxidized film.

Next, the polymer A was dissolved in ortho-dichlorobenzene to prepare a solution having a concentration of the polymer A of 0.5% by weight, and the solution was filtrated through a membrane filter to prepare a coating solution. The coating solution was coated by a spin coat method on the above-described surface-treated substrate, to form a coated film of the polymer A. The thickness of the coated film was about 30 nm. Further, the coated film was thermally treated at 170° C. for 30 minutes in a nitrogen atmosphere, to form an organic semiconductor film of the polymer A.

Further, a source electrode and a drain electrode were fabricated on the organic semiconductor film by a vacuum vapor deposition method using a metal mask to produce an organic transistor, the electrode having a laminated structure of molybdenum trioxide and gold from the organic semiconductor film side.

Example 10

Evaluation of Organic Transistor

The electric properties of the organic transistor were measured using Semiconductor Parameter 4200 (manufactured by KEITHLEY). As a result, the change curve of the drain current (Id) against the drain voltage (Vd) was good, and when the negative gate voltage to be applied on the gate electrode was increased, also the negative drain current increased, that is, the organic transistor could be confirmed as a p-type organic transistor. The electric field effect mobility p of carrier in the organic transistor was calculated using the following equation (a) representing the drain current Id in the saturated region of the electric property of the organic transistor.

$$Id = (W/2L)\mu Ci(Vg-Vt)^2 \quad (a)$$

(wherein L represents the channel length of the organic transistor, W represents the channel width of the organic transistor, Ci represents the capacity per unit area of the gate insulation film, Vg represents the gate voltage, Vt represents the threshold voltage of the gate voltage.)

As a result, the electric field effect mobility of carrier (carrier mobility) was $7.5 \times 10^{-3}$ cm$^2$/Vs, and the on/off current ratio was $10^5$. The results are shown in Table 1.

Example 11

An organic transistor device was fabricated by the same manner as in Example 9 excepting that the polymer B was used instead of the polymer A, and the transistor characteristics were evaluated by the same manner as in Example 10. The carrier mobility was $7.0 \times 10^{-4}$ cm$^2$/Vs and the on/off current ratio was $10^4$. The results are shown in Table 1.

Example 12

An organic transistor device was fabricated by the same manner as in Example 9 excepting that the polymer C was used instead of the polymer A, and the transistor characteristics were evaluated by the same manner as in Example 10. The carrier mobility was $2.1 \times 10^{-3}$ cm$^2$/Vs and the on/off current ratio was $10^5$. The results are shown in Table 1.

Example 13

An organic transistor device was fabricated by the same manner as in Example 9 excepting that the polymer D was used instead of the polymer A, and the transistor characteristics were evaluated by the same manner as in Example 10. The carrier mobility was $5.0 \times 10^{-4}$ cm$^2$/Vs and the on/off current ratio was $10^4$. The results are shown in Table 1.

TABLE 1

Result of evaluation of organic transistor device

| | | Carrier mobility (cm$^2$/Vs) | On/off ratio |
| --- | --- | --- | --- |
| Example 10 | Polymer A | $7.5 \times 10^{-3}$ | $10^5$ |
| Example 11 | Polymer B | $7.0 \times 10^{-4}$ | $10^4$ |
| Example 12 | Polymer C | $2.1 \times 10^{-3}$ | $10^5$ |
| Example 13 | Polymer D | $5.0 \times 10^{-4}$ | $10^4$ |

Example 14

Fabrication and Evaluation of Ink and Organic Film Solar Battery

A glass substrate carrying thereon an ITO film having a thickness of 150 nm formed by a sputtering method was treated with ozone and UV, thereby attaining surface treatment. Next, the polymer A and fullerene C60PCBM (phenyl C61-butyric acid methyl ester, manufactured by Frontier Carbon Corporation) were dissolved in ortho-dichlorobenzene so that the ratio of the weight of C60PCBM to the weight of the polymer A was 3, to produce an ink. Based on the weight of the ink, the sum of the weight of the polymer A and the weight of C60PCBM was 2.0% by weight. The ink was coated on the glass substrate by spin coating, to fabricate an organic film containing the polymer A. The film thickness was about 100 nm. Thus fabricated organic film had an optical absorption end wavelength of 780 nm. Thereafter, lithium fluoride was vapor-deposited with a thickness of 2 nm on the organic film, then, Al was vapor-deposited with a thickness of 100 nm, by a vacuum vapor deposition machine, to produce an organic film solar battery. The shape of the resultant organic film solar battery was 2 mm×2 mm square. The resultant organic film solar battery was irradiated with constant light using Solar Simulator (manufactured by Bunkoukeiki Co., Ltd., trade name: OTENTO-SUNII: AM 1.5G filter, irradiance: 100 mW/cm$^2$), the generated current and voltage were measured, and the photoelectric conversion efficiency, the short-circuit current density, the open voltage and the fill factor were calculated. Jsc (short-circuit current density) was 2.64 mA/cm$^2$, Voc (open end voltage) was 0.81 V, ff (fill factor) was 0.55 and the photoelectric conversion efficiency ($\eta$) was 1.24%. The results are shown in Table 2.

Example 15

An ink and an organic film solar battery were fabricated and evaluated by the same manner as in Example 14 excepting that the polymer C was used instead of the polymer A. Jsc (short-circuit current density) was 2.65 mA/cm$^2$, Voc (open end voltage) was 0.79 V, ff (fill factor) was 0.59 and the photoelectric conversion efficiency ($\eta$) was 1.22%. The results are shown in Table 2.

Example 16

An ink and an organic film solar battery were fabricated and evaluated by the same manner as in Example 14 excepting that the polymer D was used instead of the polymer A. Jsc (short-circuit current density) was 2.67 mA/cm$^2$, Voc (open end voltage) was 0.91 V, ff (fill factor) was 0.64 and the photoelectric conversion efficiency (η) was 1.57%. The results are shown in Table 2.

Comparative Example 1

An ink and an organic film solar battery were fabricated and evaluated by the same manner as in Example 14 excepting that the polymer E was used instead of the polymer A. Jsc (short-circuit current density) was 4.61 mA/cm$^2$, Voc (open end voltage) was 0.60 V, ff (fill factor) was 0.33 and the photoelectric conversion efficiency (η) was 0.91%. The results are shown in Table 2.

TABLE 2

Result of evaluation of photoelectric conversion device

| | | Short-circuit current density (mA/cm$^2$) | Open end voltage (V) | Fill factor | Photoelectric conversion efficiency (%) |
|---|---|---|---|---|---|
| Example 14 | Polymer A | 2.64 | 0.81 | 0.55 | 1.24 |
| Example 15 | Polymer C | 2.65 | 0.79 | 0.59 | 1.22 |
| Example 16 | Polymer D | 2.67 | 0.91 | 0.64 | 1.57 |
| Comparative Example 1 | Polymer E | 4.61 | 0.60 | 0.33 | 0.91 |

INDUSTRIAL APPLICABILITY

The organic film solar battery having an organic layer containing the polymer compound of the present invention is useful because of large open end voltage.

The invention claimed is:

1. A polymer compound comprising a constituent unit represented by the formula (1), the formula (2), the formula (3) or the formula (4):

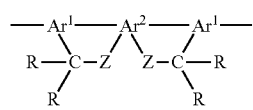

(1)

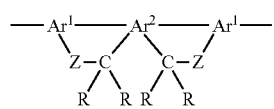

(2)

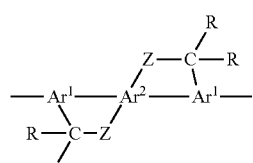

(3)

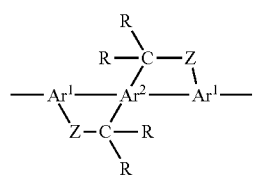

(4)

wherein in the formulae (1) to (4), Ar$^1$ represents a tri-valent aromatic carbocyclic group or a tri-valent aromatic heterocyclic group, Ar$^2$ represents a tetra-valent aromatic carbocyclic group or a tetra-valent aromatic heterocyclic group, Z represents —O—, —S—, —C(=O)—, —S(=O)—, —Si(R)$_2$—, —B(R)—, —P(R)— or —P(=O)(R)—, R represents a hydrogen atom, a halogen atom or a mono-valent group, the Ar$^1$s may each be the same or mutually different, the Zs may each be the same or mutually different, and a plurality of Rs may be the same or mutually different.

2. The polymer compound according to claim 1, wherein the constituent unit represented by the formula (1), the formula (2), the formula (3) or the formula (4) is a constituent unit represented by the formula (5), the formula (6), the formula (7) or the formula (8):

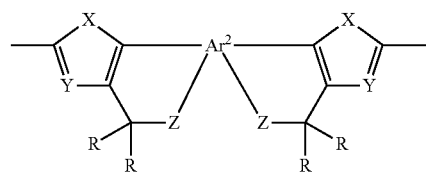

(5)

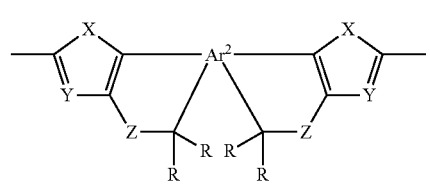

(6)

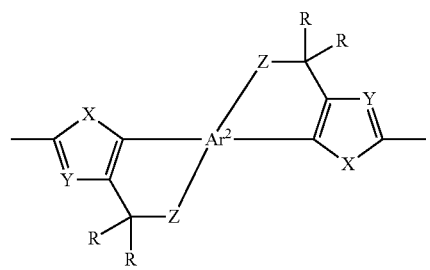

(7)

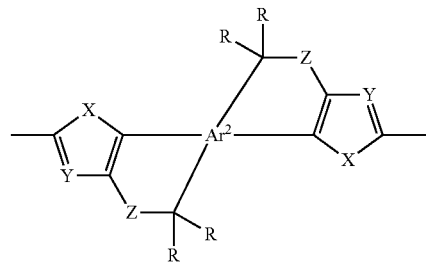

(8)

wherein in the formulae (5) to (8), X represents a sulfur atom, an oxygen atom, a selenium atom, —NH— or —N(R)—, Ar$^2$, Z and R represent the same meaning as described above, Y represents a nitrogen atom or =CH—, the Xs may each be the same or mutually different, the Ys may each be the same or mutually different.

3. The polymer compound according to claim 1, wherein the constituent unit represented by the formula (1), the formula (2), the formula (3) or the formula (4) is a constituent unit represented by the formula (9), the formula (10), the formula (11) or the formula (12):

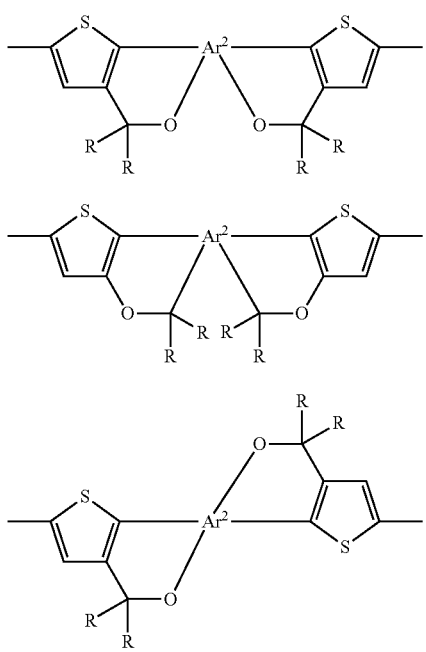

(9)
(10)
(11)

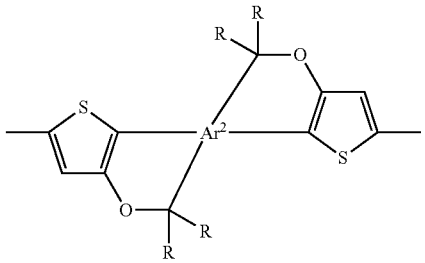

(12)

wherein in the formulae (9) to (12), $Ar^2$ and R represent the same meaning as described above.

4. The polymer compound according to claim 1, having a polystyrene-equivalent number-average molecular weight of 3000 or more.

5. A film comprising the polymer compound according to claim 1.

6. A composition comprising the polymer compound according to claim 1 and an electron accepting compound.

7. The composition according to claim 6, wherein the electron accepting compound is a fullerene derivative.

8. A film comprising the composition according to claim 6.

9. An electronic device using the film according to claim 5.

* * * * *